(12) United States Patent
Jacobsen et al.

(10) Patent No.: US 9,227,995 B2
(45) Date of Patent: Jan. 5, 2016

(54) PEPTIDES

(75) Inventors: Øyvind Jacobsen, Blindern (NO); Pål Rongved, Blindern (NO); Jo Klaveness, Blindern (NO)

(73) Assignees: Øyvind Jacobsen, Holmestrand (NO); DRUG DISCOVERY LABORATORY AS, Oslo (NO)

( * ) Notice: Subject to any disclaimer, the term of this patent is extended or adjusted under 35 U.S.C. 154(b) by 257 days.

(21) Appl. No.: 13/064,881

(22) Filed: Apr. 22, 2011

(65) Prior Publication Data

US 2011/0263479 A1  Oct. 27, 2011

Related U.S. Application Data

(60) Provisional application No. 61/282,929, filed on Apr. 23, 2010.

(51) Int. Cl.
| | | |
|---|---|---|
| *A61K 38/03* | (2006.01) | |
| *C07K 4/00* | (2006.01) | |
| *C07K 1/107* | (2006.01) | |
| *C07K 5/117* | (2006.01) | |
| *C07K 7/06* | (2006.01) | |
| *A61K 38/00* | (2006.01) | |

(52) U.S. Cl.
CPC ............ *C07K 5/1024* (2013.01); *C07K 1/107* (2013.01); *C07K 1/1072* (2013.01); *C07K 1/1075* (2013.01); *C07K 4/00* (2013.01); *C07K 7/06* (2013.01); *A61K 38/00* (2013.01); *A61K 38/03* (2013.01)

(58) Field of Classification Search
USPC ........................................................ 514/1.1
See application file for complete search history.

(56) References Cited

U.S. PATENT DOCUMENTS

2008/0262200 A1* 10/2008 Nash ............................ 530/331

FOREIGN PATENT DOCUMENTS

| WO | WO 2010/033617 A2 | 3/2010 |
|---|---|---|
| WO | WO 2010/068684 | 6/2010 |

OTHER PUBLICATIONS

Jacobsen et al, "Stapling of a $3_{10}$-Helix with Click Chemistry", J. Org. Chem. 2011, 76, 1228-1238.
Holub et al, "Fit to be Tied: Conformation-Directed Macrocyclization of Peptoid Foldamers", Organic Letters 2007, vol. 9, No. 17, 3275-3278.
Goddard-Borger et al, "An Efficient, Inexpensive, and Shelf-Stable Diazotransfer Reagent: Imidazole-1-sulfonyl Azide Hydrochloride", Organic Letters 2007, vol. 9, No. 19, 3797-3800.
Boal et al, "Facile and E-Selective Intramolecular Ring-Closing Metathesis Reactions . . . ", J. Am. Chem. Soc. 2007, 129, 6986-6987.
Schafmeister et al, "An All-Hydrocarbon Cross-Linking System . . . ", J. Am. Chem. Soc. 2000, 122, 5891-5892.
Blackwell et al, "Highly Efficient Synthesis of Covalently Cross-Linked . . . ", Angew. Chem. Int. Ed. 1988, 37, No. 23, 3281-3284, 1998.
Jacobsen, "Approaches to Conformational Stabilization of Peptide $3_{10}$ helices and AQP4 Inhibitor Design", Power Point Presentation given in Jan. 2010 in Norway.
Jacobsen et al, "Synthesis of cyclic peptide analogues . . . ", Org. Biomol. Chem, Apr. 21, 2009 7(8); 1599-611.
Jacobsen et al, "Approaches to conformational stabilization . . . ", Abstract, Jan. 2010.

* cited by examiner

*Primary Examiner* — Marcela M Cordero Garcia
*Assistant Examiner* — Catherine Mader
(74) *Attorney, Agent, or Firm* — Nixon & Vanderhye PC

(57) ABSTRACT

A peptide which can adopt a $3_{10}$-helical conformation in which the side chains of two amino acid residues in the peptide backbone are linked by a group comprising an aromatic 5-membered ring.

22 Claims, 5 Drawing Sheets

PEPTIDES

This application claims priority of U.S. provisional application Ser. No. 61/282,929 filed Apr. 23, 2010, the entire content of which is hereby incorporated by reference in this application

FIELD OF INVENTION

This invention relates to conformational stabilisation of peptides and in particular to the generation of $3_{10}$-helices which are bridged to provide conformational stability.

BACKGROUND OF INVENTION

The $3_{10}$-helix is defined by intramolecular H-bonds between amino acid residues placed at positions i and i+3, and is an important structural motif in peptides and proteins. It plays important roles in many different biological recognition processes. It is the biologically active conformation of many pharmacologically interesting peptides/peptidomimetics. In addition, many protein segments mediating physiologically or pathophysiologically important interactions between biomolecules (e.g. two proteins or a peptide with a protein) adopt a $3_{10}$-helical conformation.

Two examples are the interactions between aquaporin-4 (AQP4) and aquaporin-4 and between AQP4 and the antibody NMO-IgG, the latter being important in the pathophysiology of the multiple sclerosis like disease neuromyelitis optica (NMO).

The concept of introducing conformational constraints in peptides which stabilize their biologically active secondary structure has attracted a lot of interest as a way to improve the pharmacological properties of peptides. In particular, this concept has been applied to α-helical peptides and protein segments. Examples include peptides with intramolecular H-bond surrogates[1] and so-called stapled peptides, the latter deriving helix stabilization from side chain-to-side chain hydrophobic interactions,[2] salt bridges,[3] disulfide bridges,[4] lactams[5] and metathesis derived hydrocarbon bridges.[6-8] Significantly, hydrocarbon stapling of α-helical peptides has resulted in a number of compounds with clinical potential, e.g. against cancer.[9] Recently, hydrocarbon stapling has also been successfully applied to $3_{14}$-helical β-peptides,[10] extending its range of applicability beyond α-peptides.

The $3_{10}$-helix, which is defined by intramolecular i→i+3 H-bonds, is an important structural element in proteins, peptide antibiotics known as peptaibols,[11] and many biological recognition processes, as well as a postulated intermediate structure in protein folding.[12]

Over the last decade the predominant water channel in the mammalian brain, aquaporin-4 (AQP4), has emerged as an important target for treatment of brain edema after stroke or trauma.[13-16] The present inventors considered the development of selective inhibitors of AQP4 based on side chain-to-side chain cyclised $3_{10}$-helical analogues of the Pro138-Gly144 segment of human AQP4,[17] which has been postulated to mediate adhesive interactions between two AQP4 tetramers.[18-20]

Examples of i→i+3 and i→i+4 side chain-to-side chain crosslinking in $3_{10}$-helical peptides by Glu-Lys lactam formation,[21] ferrocenedicarboxylic acid Lys diamides,[22] photoinduced 1,3-dipolar cycloaddition,[23] metathesis derived hydrocarbon bridges,[17,24,25] and a p-phenylenediacetic acid bridge[26] between two α,α-disubstituted 4-aminopiperidine-4-carboxylic acid (Api) residues have been reported. However, only two studies[25,26] have provided atomic resolution detail of the effect of cyclization on helix regularity, i.e. on backbone dihedral angles and H-bond lengths, and very little[23] is known on how cyclization/stapling affects the thermal stability of the $3_{10}$-helix.

In the first X-ray crystallographic study[25] of the effect of side chain-to-side chain cyclization in a $3_{10}$-helical peptide it was observed that the backbone is distorted by an i→i+3 metathesis derived olefinic bridge, resulting in the breakage of one intramolecular H-bond, thus disrupting the $3_{10}$-helix. The p-phenylenediacetic acid bridge on the other hand appears to afford a highly regular Api/Aib based $3_{10}$-helix.[26] However, α,α-disubstituted amino acids like Aib and N-acylated Api are generally hydrophobic and have a tendency to distort the dihedral angles of neighbouring monosubstituted, proteinogenic residues away from ideality.[21,25,27] Hence, alternative methodology for side chain-to-side chain crosslinking of monosubstituted residues, which are expected to be better tolerated in the context of a helical peptide primarily consisting of the proteinogenic amino acids, which does not significantly distort the regularity of the $3_{10}$-helix, is highly desirable. If, at the same time, the crosslinking provides thermal stabilization of the $3_{10}$-helix and results in a more hydrophilic bridge, thus increasing the aqueous solubility of the stapled peptide, such a methodology could potentially have broad utility to the study and modulation of biologically important recognition processes involving $3_{10}$-helical peptides and protein segments.

There has been an explosion of interest in click chemistry[28] in recent years, exemplified by the highly popular copper(I)-catalyzed azide-alkyne cycloaddition (CuAAC) reaction.[29-32] This reaction has been successfully applied to i→i+4 side chain-to-side chain cyclization in an α-helical peptide[33,34] and i→i+3 cyclization in peptoids (peptides composed of N-substituted glycines).[35] The high functional group tolerance of the CuAAC reaction, the very large dipole moment (~5D)[36] and the relatively high resistance to metabolic degradation[37,38] of the 1,2,3-triazole moiety make $3_{10}$-helical peptides with a side chain-to-side chain triazole bridge highly interesting objects of study.

The present inventors have installed an i→→i+3 constraint by side chain-to-side chain CuAAC between two monosubstituted residues in the context of a $3_{10}$-helical Aib rich peptide and examined in detail the effect of cyclization on helix regularity and on helix stability. To allow a direct comparison with the results for the i→i+3 hydrocarbon bridge, two octapeptides 21 (Scheme 1) and 23 (Scheme 2) with the reactive/crosslinked residues in the same Aib rich context as the olefinic peptides of Boal et al[25] were chosen as synthetic targets.

The inventors provide the first X-ray structural investigation of a (α- or $3_{10}$-) helical peptide after stapling by CuAAC or with a triazole derived conformational constraint, the first systematic thermodynamic and computational analysis of any stapled $3_{10}$-helical peptide and the first 2D IR structural investigation of a helical peptide with a conformational constraint installed. Surprisingly perhaps, given the widespread interest in the CuAAC reaction, this study will also afford what appears to be the first crystal structure of a difunctional azide-alkyne compound.

SUMMARY OF INVENTION

Viewed from one aspect the invention provides a peptide which can adopt a $3_{10}$-helical conformation in which the side chains of two amino acid residues in the peptide backbone are linked by a group comprising an aromatic 5-membered ring. In particular, the peptide is in substantially $3_{10}$-helical conformation.

Viewed from another aspect the invention provides a pharmaceutical composition comprising a peptide as hereinbefore defined.

Viewed from another aspect the invention provides a method for treating an AQP4 related condition comprising administering to a patient in need thereof an effective amount of a peptide as hereinbefore defined.

Viewed from another aspect the invention provides a method for stabilising a short peptide of between 4 and 15 units, e.g. 5 to 12 units, in a conformationally rigid $3_{10}$-helical conformation by cyclising the side chains of two separate amino acid residues using a linker comprising an aromatic 5-membered ring, especially a triazole group.

DETAILED DESCRIPTION OF INVENTION

Figure 1:
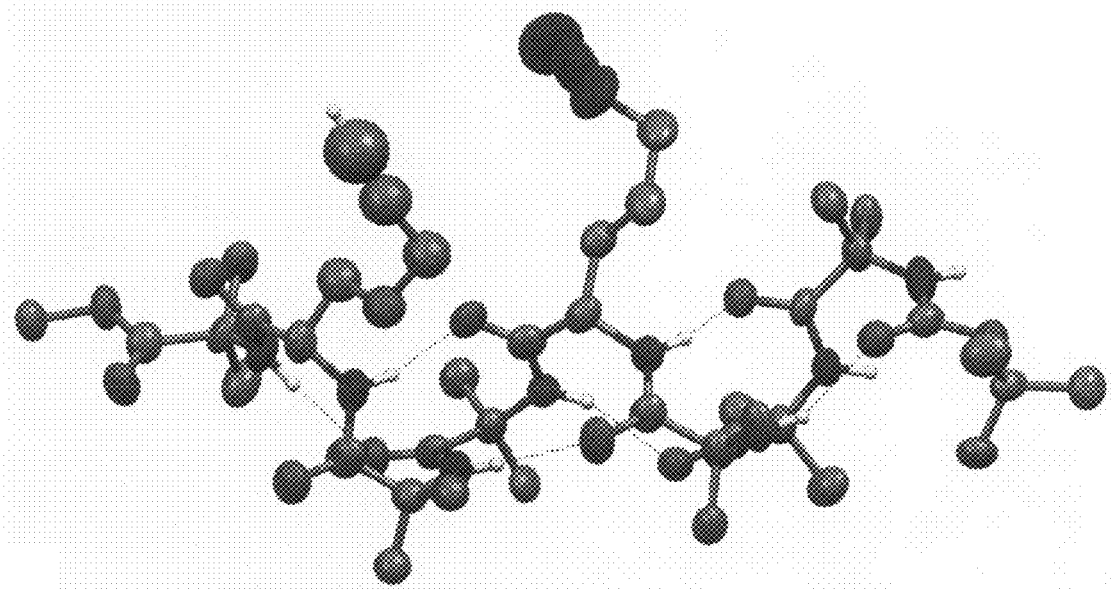
FIG. 1. is a thermal ellipsoid plot of the X-ray crystal structure of the acyclic peptide 21 at the 50% probability level with intramolecular H-bonds indicated. Apolar hydrogens have been omitted for clarity. The major backbone conformation at Aib6 is shown.

This invention relates to the stabilisation of short peptides, which generally are unstructured in solution, in a $3_{10}$-helix conformation by "stapling", i.e. by the introduction of a linker bridging the side chains of two amino acid residues in the chain (with formation of a large macrocyclic ring). This technique can used to create high affinity ligands for many important peptide, protein, nucleic acid and other biomolecule targets, with applications in drug discovery and development, diagnostics (peptides conjugated to a PET active isotope, MRI etc.) and chemical biology. The treatment of brain edema, stroke, neuromyelitis optica and other AQP4 related diseases is envisaged.

The term peptide therefore refers to a short polymer of amino acids linked by peptide bonds. Those amino acids can be essential amino acids or non essential amino acids or indeed not natural.

The present inventors seek to prepare short peptides, e.g. having 4 to 15 residues, in which an internal cross-link is formed between side chains of amino acid residues, with the cross-link comprising an aromatic 5-membered ring, e.g. a triazole group. This assists the unstructured peptide to adopt a $3_{10}$-helical conformation. The term "triazole" designates a 1,2,3-triazole or a 1,2,4-triazole.

This increases the affinity of a peptide for its target, given that the peptide's biologically most active conformation is a $3_{10}$-helix.

An added advantage of the disclosed methodology over existing methodologies is the large dipole moment of the triazole moiety, which confers much improved aqueous solubility to the peptide, without introducing any charged/ionizable groups. Introducing charged/ionizable groups could negatively influence the bioavailability of the peptide by preventing uptake from the GI tract or from blood into the CNS.

A further potential advantage is improved protease stability. Proteases recognize peptide substrates in a β-strand conformation (Tyndall, J. D. A.; Nall, T.; Fairlie, D. P., *Chem. Rev.* 2005, 105, 973-999). A side chain-to-side chain staple forcing the peptide to adopt a $3_{10}$-helical conformation will prevent binding of the peptide to a protease active site. As a result, the peptide will not be proteolytically degraded as quickly as a non-stapled peptide.

Viewed from one aspect the invention provides a peptide which can adopt a $3_{10}$-helical conformation in which the side chains of two amino acid residues in the peptide backbone are linked by a group comprising an aromatic 5-membered ring, in particular a triazole group. The use of a triazole group is a preferred aspect of the invention. However, due to the very close similarities between different aromatic 5-membered rings with respect to size, shape (all are planar or close to planar) and electronic properties other aromatic 5-membered rings which could be used in place of a triazole group include cyclopentadiene, pyrrole, furan, thiophene, selenophene, tellurophene, phosphole, arsole, stibole, bismole, silole, germole, stannole, plumbole, borole, pyrazole, imidazole, isoxazole, oxazole, isothiazole, thiazole, 1,2-selenazole, 1,3-selenazole, 1,2-dioxoles, 1,2-oxathiole, 1,3-dioxole, 1,3-oxathiole, 1,2-dithiole, 1,3-dithiole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2-oxa/thia-3-azole, 1,3-oxa/thia-2-azole, 1,2-oxa/thia-4-azole, 1,4-oxa/thia-2-azole, tetrazole, oxatriazole, 1,2,3,4-thiatriazole, 1,2,3,5-thiatriazole and others described in sources such as Comprehensive Heterocyclic Chemistry II, Eds. A. R. Katritzky, C. W. Rees, E. F. V. Scriven, Vol. 2, 3 and 4.

It is believed that planar, aromatic 5-membered rings preserve the close-to-ideal $3_{10}$-helical conformation better than non-aromatic heterocycles. This is especially the case in the context of the side chain-to-side chain bridge of 23 and similar side chain-to-side chain bridges.

In particular, the invention provides a peptide in which a link is formed between the side chains of two amino acids placed at positions i and i+3, e.g. positions 1 and 4 or 2 and 5 or 3 and 6 etc., to each other, i.e. the first bridging amino acid could be placed at position "1" and the second bridging amino acid at position "4" in the peptide chain. There can obviously be other non-bridged residues present on either side of the looped residues.

In particular, the invention provides a peptide in which a serine residue is bonded to the side chain of an amino acid residue 3 amino acid residues away (by definition, two neighbouring amino acids are one amino acid residue away from each other) by a linker comprising an aromatic 5-membered ring, e.g. a triazole.

It is also preferred if the invention provides a peptide in which an ornithine residue or norvaline residue is bonded to the side chain of an amino acid residue 3 amino acid residues away by a linker comprising an aromatic 5-membered ring, e.g. a triazole.

It is also preferred if the invention provides a peptide in which an ornithine residue or norvaline residue is bonded to the side chain of a serine amino acid residue 3 amino acid residues away by a linker comprising an aromatic 5-membered ring, e.g. a triazole.

The triazole group which may form part of the macrocycle is preferably bonded through the 1- and 4-positions of the triazole ring. Thus, one bond is formed to the first nitrogen atom and the second bond is formed through a carbon atom.

In a highly preferred embodiment, the "staple" should not distort the conformation of the $3_{10}$-helix. The use of a five membered aromatic staple provides a $3_{10}$-helical state of the peptide which is more ideal than is the case with the non-stapled precursor. Also, a staple should thermodynamically stabilize the bioactive $3_{10}$-helical conformation relative to undesired conformations. It is not obvious that a given i→i+3 staple thermodynamically stabilizes (enthalpically and/or entropically) the peptide in a $3_{10}$-helical conformation or that it does not distort the $3_{10}$-helical state of the peptide. If the staple is not carefully designed, e.g. like the staple of 23, an i→i+3 side chain-to-side chain staple could in fact stabilize an α-helical or a $P_{11}$-helical state instead of the desired $3_{10}$-helical state, as these secondary structures also have a helical pitch of 3-4 residues.

The number of atoms forming the macrocycle (between amino acids residues) is preferably 15 to 22, more preferably 18-20, especially 19. This figure is calculated by counting around the shortest route around the triazole ring and then every atom in the whole macrocyclic loop backbone.

The atoms which form the linker (i.e. those not in the backbone of the peptide) are those of the aromatic five membered ring as well as further C or heteratoms which link the backbone. It is preferred if there are 3 atoms from the peptide backbone to the aromatic five membered ring from both backbone binding points. Those atoms can be C or heteroatoms, especially O.

It is preferred if the link is made from a serine amino acid and hence one of the linking groups is —$CH_2$—O—$CH_2$—. The other link is preferably made via an ornithine/norvaline residue. The link which forms from backbone to aromatic five membered ring is preferably n-propylene.

In particular, the invention relates to the use of alkyne/azide cycloaddition to form the linker. This reaction can be catalysed using Cu(I) ions.

It is further preferred therefore if one of the side chains of the amino acid residues which can be reacted to form the linker is functionalised to contain an alkyne group, e.g. —$CH_2C≡CH$. Preferably, the other side chain is functionalised to carry an azide group. Ideally the alkyne group is attached to a serine residue to form the complete side chain —$CH_2OCH_2C≡CH$. Preferably the azide residue is attached via the side chain —$CH_2CH_2CH_2N_3$. This can be achieved as described further below, e.g. starting from ornithine.

Copper (I) catalysed cycloaddition allows the formation of a macrocycle. The group bridging the peptide chain therefore preferably becomes

(I)

wherein $L_1$ is a $C_{2-5}$-alkyl chain optionally interrupted by at least one heteroatom, especially one O atom and $L_2$ is a $C_{2-5}$ alkyl chain optionally interrupted by at least one heteroatom, especially one O atom. Heteroatoms could be O, N or S.

It is preferred if only $L_2$ comprises a heteroatom and hence $L_2$ preferably represents the connection via a serine residue, i.e. $CH_2$—O—$CH_2$. It is preferred if both L1 and L2 are free of N atoms. It is preferred if the linker group between the backbone and the aromatic ring is free of carbonyl linkages.

$L_1$ preferably represent C3 alkylene.

It is preferred if the actual linking group from peptide backbone back to peptide backbone is 8 to 12 atoms in length, preferably 9 to 11 atoms, such as 10 atoms. This is based on counting atoms around the shortest route in the aromatic ring.

It is stressed that the linker preferably starts and ends at the central C atom of an amino acid in the backbone of the peptide. It is not preferred to bridge using a nitrogen atom from the peptide backbone.

Viewed from another aspect the invention provides a process for the formation of a $3_{10}$-helical peptide comprising reacting an azide functionalised side chain of an amino acid with an alkyne functionalised side chain of an amino acid positioned 3 residues away from each other in the presence of a Cu(I) catalyst so as to form a triazole group.

In particular, the process provides a linker of formula (I).

The compound of the invention may therefore contain a group of formula (II)

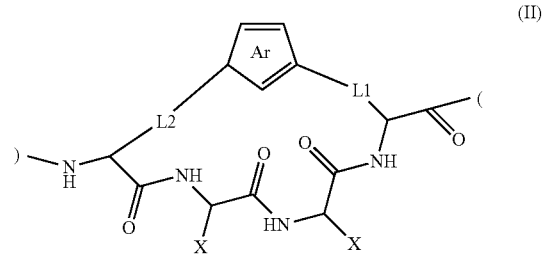

(II)

Where Ar is a aromatic 5-membered ring which may contain heteroatoms, X is a side chain on the amino acid and may represent two such side chain groups bonding at the same atom, and L1 and L2 are as hereinbefore defined. It will be appreciated that other groups may attach to the N and C termini of this structure, in particular amino acids to form amide bonds, an N or C terminus protecting group or simply an H or OH group. This structure emphasizes that the bond to the linker derives from a C atom, not an N atom.

The group X is preferably the side chain on a known amino acid such as valine, leucine, Aib, proline and so on. It may be the side chain of a essential or non essential amino acid.

The other amino acid residues making up the peptide chain and in particular those forming part of the macrocycle can be any amino acid residue, especially proteinogenic amino acid residues. The term residue is used to cover an amino acid unit within a peptide. If one or both of the other amino acid residues in the macrocycle is a non-proteinogenic amino acid, the use of Aib (aminoisobutyric acid) is especially preferred as this amino acid has been found to encourage formation of $3_{10}$-helices. The use of Aib in other parts of the peptide chain is also preferred. Other favoured amino acids include proline, valine and leucine. Non-essential or non-natural amino acids can also be employed.

The use of valine or the use of Aib in the backbone at position i+1 or i+2 (i.e. between the linking points of the macrocycle) is especially preferred, e.g. in the case of $3_{10}$-helical peptides with binding affinity for AQP4.

It is preferred if the peptide chain contains at least one non-glycine residue. In particular, the amino acids within the macrocycle are preferably not glycine. The use of non-glycine residues encourages the correct helix to form.

There can be up to 15 residues, e.g. 3 to 12 residues, such as 4 to 11 residues or 5 to 10 residues in the compounds of the invention. Shorter peptides of 3 to 10 residues are favoured.

Viewed from another aspect the invention provides a method for stabilising a short peptide of between 4 and 15 residues, e.g. 5 to 12 residues, in a conformationally rigid $3_{10}$-helical conformation by cyclising the side chains of two separate amino acid residues using a linker comprising an aromatic 5-membered ring, e.g. a triazole group.

The term conformationally rigid is used to designate the presence of a linker and hence the formation of a macrocycle making the enthalpy and/or entropy of unfolding for the process $$3_{10}\text{-helix} \rightarrow \text{unfolded peptide}$$

less negative (equivalent: more positive) and less positive (equivalent: more negative) respectively.

Hence the formation of a $3_{10}$-helix which is enthalpically and/or entropically stabilized with respect to unfolding compared to a comparable peptide without the linker.

Any peptide of the invention can be in salt form. It is preferred that the amino acid residues at the ends of the peptide chain are protected, e.g. using conventional N and C terminus protecting groups.

It is preferred if the amino acids are in their natural L chiral form. It is preferred if the compounds of the invention are crystalline. It is preferred if the solubility of the compounds of the invention is at least 1 mM in water.

Ideally, in the case of peptides with binding affinity to AQP4, the compounds of the invention can mimic the Pro138 to Gly 144 part of AQP4.

It is also preferred if the compounds of the invention retain their $3_{10}$-helical structure in non-aqueous solvents, in particular apolar solvents such as dichloromethane.

It is believed that the compounds of the invention are able to provide $3_{10}$-helices whose angles deviate less than 3° from a perfect helix. A perfect helix is here defined as a helix consisting of residues with dihedral angles equal to the average[52] dihedral angles observed in $3_{10}$-helical peptides.

The synthesis of the peptide compounds of the invention is exemplified in detail below.

The compounds of the invention can be converted into pharmaceutical compositions using conventional excipients and carriers. These may be formulated for administration via any convenient route such as orally, nasally, topically, intraperitoneally, intravenously, intramuscularly, subcutaneously and so on.

The amount administered will be effective. That will vary depending on the patient, the disease, and so on. The skilled man can determine the necessary amounts.

Formulation

The compounds of the invention are preferably formulated as pharmaceutically acceptable compositions. The phrase "pharmaceutically acceptable", as used in connection with compositions of the invention, refers to molecular entities and other ingredients of such compositions that are physiologically tolerable and do not typically produce untoward reactions when administered to a mammal (e.g. human). Preferably, as used herein, the term "pharmaceutically acceptable" means approved by a regulatory agency of the Federal or a state government or listed in the U.S. Pharmacopoeia or other generally recognized pharmacopoeia for use in mammals, and more particularly in humans.

The term "carrier" applied to pharmaceutical compositions of the invention refers to a diluent, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical carriers are described in "Remington's Pharmaceutical Sciences" by E. W. Martin, 18th Edition, incorporated by reference. Particularly preferred for the present invention are carriers suitable for immediate-release, i.e., release of most or all of the active ingredient over a short period of time, such as 60 minutes or less, and make rapid absorption of the drug possible.

The compounds of the invention are proposed for use in the treatment of certain conditions. By treating or treatment is meant at least one of:

(i). preventing or delaying the appearance of clinical symptoms of the disease developing in a mammal;

(ii). inhibiting the disease i.e. arresting, reducing or delaying the development of the disease or a relapse thereof or at least one clinical or subclinical symptom thereof, or (iii). relieving or attenuating one or more of the clinical or subclinical symptoms of the disease.

The benefit to a subject to be treated is either statistically significant or at least perceptible to the patient or to the physician. In general a skilled man can appreciate when "treatment" occurs.

The word "treatment" is also used herein to cover prophylactic treatment, i.e. treating subjects who are at risk of developing a disease in question.

The compounds of the invention can be used on any animal subject, in particular a mammal and more particularly to a human or an animal serving as a model for a disease (e.g. mouse, monkey, etc.).

An "effective amount" means the amount of a compound that, when administered to an animal for treating a state, disorder or condition, is sufficient to effect such treatment. The "effective amount" will vary depending on the compound, the disease and its severity and the age, weight, physical condition and responsiveness of the subject to be treated and will be ultimately at the discretion of the attendant doctor.

While it is possible that, for use in the methods of the invention, a compound of the invention may be administered as the bulk substance, it is preferable to present the active ingredient in a pharmaceutical formulation, for example, wherein the agent is in admixture with a pharmaceutically acceptable carrier selected with regard to the intended route of administration and standard pharmaceutical practice.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition. The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

It will be appreciated that pharmaceutical compositions for use in accordance with the present invention may be in the form of oral, parenteral, transdermal, inhalation, sublingual, topical, implant, nasal, or enterally administered (or other mucosally administered) suspensions, capsules or tablets, which may be formulated in conventional manner using one or more pharmaceutically acceptable carriers or excipients.

There may be different composition/formulation requirements depending on the different delivery systems. Likewise, if the composition comprises more than one active component, then those components may be administered by the same or different routes.

The pharmaceutical formulations of the present invention can be liquids that are suitable for oral, mucosal and/or parenteral administration, for example, drops, syrups, solutions, injectable solutions that are ready for use or are prepared by the dilution of a freeze-dried product but are preferably solid or semisolid as tablets, capsules, granules, powders, pellets, pessaries, suppositories, creams, salves, gels, ointments; or solutions, suspensions, emulsions, or other forms suitable for administration by the transdermal route or by inhalation.

The compounds of the invention can be administered for immediate-, delayed-, modified-, sustained-, pulsed- or controlled-release applications.

In one aspect, oral compositions are slow, delayed or positioned release (e.g., enteric especially colonic release) tablets or capsules. This release profile can be achieved without limitation by use of a coating resistant to conditions within the stomach but releasing the contents in the colon or other portion of the GI tract wherein a lesion or inflammation site has been identified or a delayed release can be achieved by a coating that is simply slow to disintegrate or the two (delayed and positioned release) profiles can be combined in a single formulation by choice of one or more appropriate coatings and other excipients. Such formulations constitute a further feature of the present invention.

Pharmaceutical compositions can be prepared by mixing a therapeutically effective amount of the active substance with a pharmaceutically acceptable carrier that can have different forms, depending on the way of administration.

Typically composition components include one or more of binders, fillers, lubricants, odorants, dyes, sweeteners, surfactants, preservatives, stabilizers and antioxidants.

The pharmaceutical compositions of the invention may contain from 0.01 to 99% weight—per volume of the active material. The therapeutic doses will generally be between about 10 and 2000 mg/day and preferably between about 30 and 1500 mg/day. Other ranges may be used, including, for example, 50-500 mg/day, 50-300 mg/day, 100-200 mg/day.

Administration may be once a day, twice a day, or more often, and may be decreased during a maintenance phase of the disease or disorder, e.g. once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art.

It is within the scope of the invention for a compound as described herein to be administered in combination with another pharmaceutical, e.g. another drug with known efficacy against the disease in question. The compounds of the invention may therefore be used in combination therapy.

The invention will now be further described with reference to the following non limiting examples:

Experimental Section

Peptide Synthesis

The building block $N^{\alpha}$-Boc-$\epsilon$-azido-L-norvaline[39] was synthesised in 63% yield from $N^{\alpha}$-Boc-L-ornithine using a recently developed shelf-stable and crystalline diazo transfer reagent, imidazole-1-sulfonyl azide hydrochloride.[40] N-Boc-O-propynyl-L-serine[41] was synthesised in 77% yield by a variation of Sugano's method for synthesis of N-Boc-O-benzyl-L-serine.[42] The octapeptide 21 was assembled by a segment condensation strategy using standard solution phase peptide coupling chemistry employing EDC/HOBt in DMF or $CH_2Cl_2$. The final steps involved deprotection of pentapeptide 18 with TFA/$CH_2Cl_2$ (1:1) and coupling of the resulting trifluoroacetate 19 with Boc-Aib-Aib-Aib-OH to afford the octapeptide 21 in 43% yield (Scheme 1).

Scheme 1. Final steps of synthesis of the acyclic peptide 21.

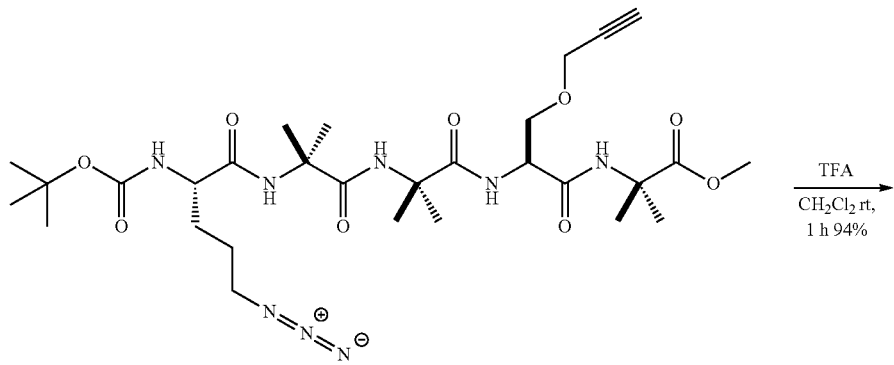

18

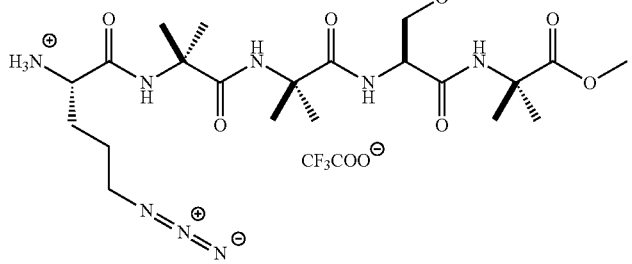

19

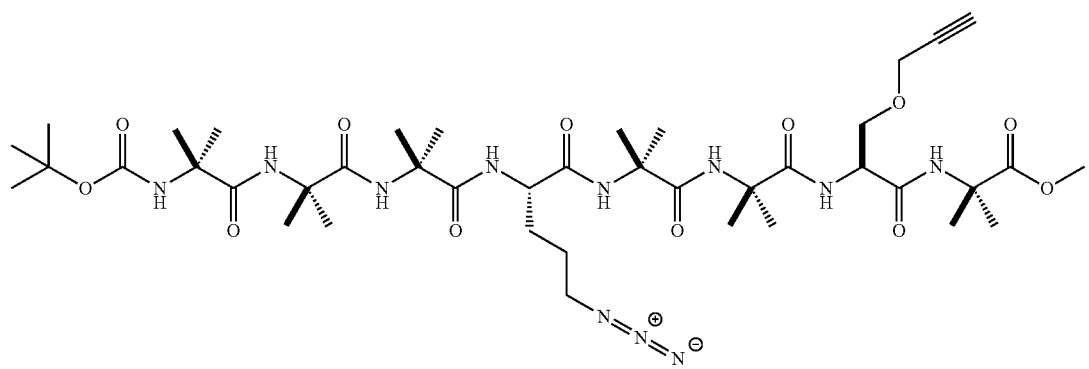

21

A recent investigation of Aib oligopeptides by 2D IR spectroscopy revealed that the onset of $3_{10}$-helical structure appears to occur already at the pentapeptide level in CDCl$_3$.[43] This, together with our previous success in cyclizing an olefinic pentapeptide by ring closing metathesis[17] in CH$_2$Cl$_2$ suggested that cyclization by CuAAC might be possible at the pentapeptide level in CH$_2$Cl$_2$. At high dilution (~0.15 mM) 18 was cyclized to 20 in 83% yield (Scheme 2) in the presence of 0.31 eq. of the organic-soluble copper(I) complex CuI·P(OEt)$_3$, which was synthesised according to a literature procedure.[44,45] Dimerization and cyclodimerization are competing processes and have resulted in relatively low yields of cyclic monomer in several instances of intramolecular CuAACs, even at high dilution.[32,46,47] The relatively high yield in this case suggests a high degree of substrate preorganization in CH$_2$Cl$_2$. Deprotection of 20 with TFA/CH$_2$Cl$_2$ (1:1), yielding the trifluoroacetate 22, followed by segment condensation with Boc-Aib-Aib-Aib-OH afforded octapeptide 23 in 73% yield over two steps (Scheme 2).

Scheme 2. Final steps of synthesis of the cyclic peptide 23.

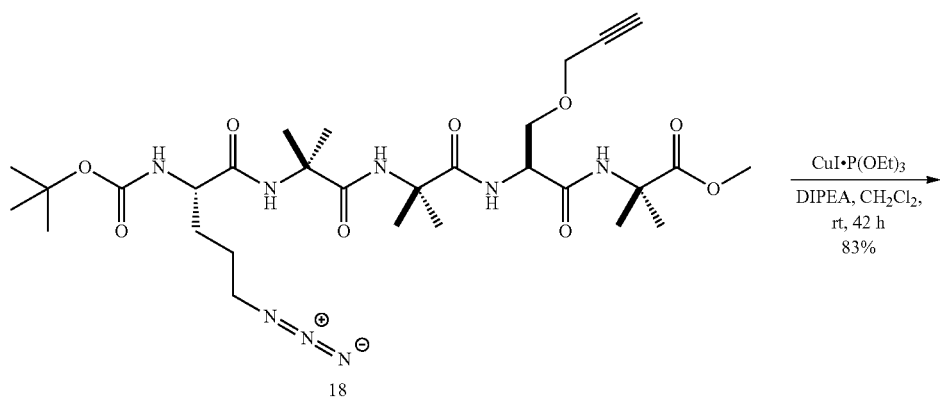

18

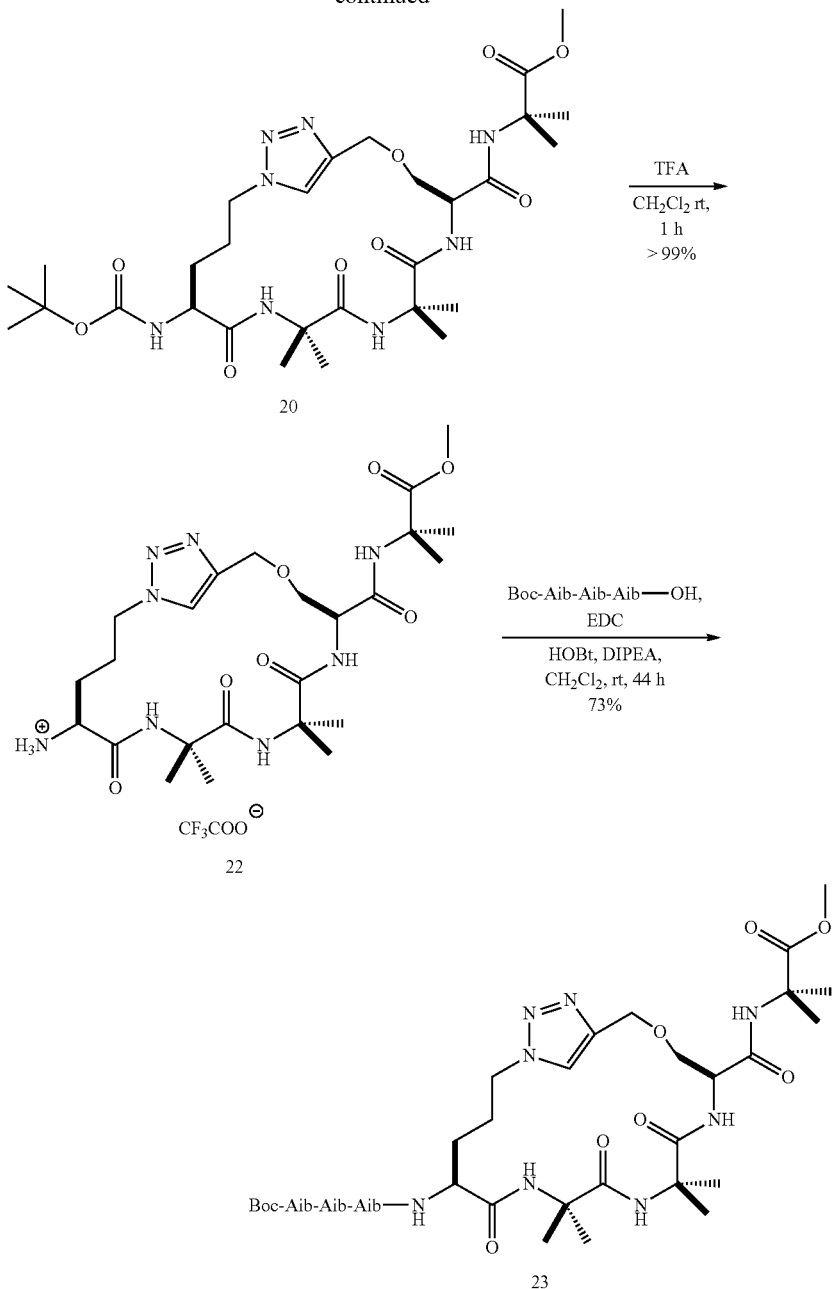

Crystallization and X-Ray Crystallography

The acyclic peptide 21 was crystallized by slow evaporation of an EtOAc solution and the cyclic peptide 23 by slow evaporation of a CH$_2$Cl$_2$/iPrOH (5:3) solution.

Single-crystal X-ray diffraction data were recorded at 110 K with Mo Kα radiation (λ=0.71073 Å) using a Bruker Apex II CCD diffractometer. Unit cell dimensions were determined in SAINT+ (Bruker, 2007) and the crystal structures solved and refined in SHELXTL (Bruker, 2008). Absorption was corrected for by multi-scan methods, SADABS (Bruker, 2007).

For 21 all peptide O-, N- and C-atoms were refined anisotropically, except in the alkyne moiety of residue 7 and the C$^\alpha$ and C$^\beta$ atoms of Aib6, for which there was disorder over two positions [occupancy of major conformation=0.588 (18), occupancy of minor conformation=0.412 (18)]. Unless otherwise stated, structural parameters for 21 in the following discussion will refer to the structure with the alkyne side chain in its major orientation and with Aib6 in its major conformation. H atoms were positioned with idealized geometry and fixed N—H distances (0.88 Å) and C—H distances (0.98-1.00 Å). U$_{iso}$ values were 1.2 U$_{eq}$ of the carrier atom or 1.5 U$_{eq}$ for amino and methyl groups. In the absence of significant anomalous scattering effects, 4370 Friedel pairs were merged.

In the case of 23 relatively large crystals were obtained, leading to collection of high quality diffraction data which allowed full anisotropic refinement of all heavy atoms (except C atoms in disordered solvent molecules), as well as refinement of positional parameters for the amide hydrogens. Other H atoms were positioned with idealized geometry and fixed C—H distances (0.98-1.00 Å). $U_{iso}$ values were 1.2 $U_{eq}$ of the carrier atom or 1.5 $U_{eq}$ for amino and methyl groups. In the absence of significant anomalous scattering effects, 5416 Friedel pairs were merged.

The crystal structures of 21 and 23 have been deposited at the Cambridge Crystallographic Data Centre (accession codes CCDC 770131 and CCDC 770132).

2D IR and NMR spectroscopy

FT IR and 2D IR Measurements

Linear IR spectra of the peptides 21 and 23 were recorded in $CH_2Cl_2$ solution using a purged FT IR spectrometer (Nicolet, 860) with a 4 $cm^{-1}$ resolution and averaged over 64 scans. The spectrum of neat $CH_2Cl_2$ (Acros, 99.9%) was also measured under the same condition and subtracted from the spectra of 21 and 23. The optical density of the amide-I band was ~0.2 at a 6 mM peptide concentration. The spectrum of a ~0.4 mM solution was also measured. The spectral line shape does not exhibit concentration dependence and thus peptide aggregation is not present in this concentration range.

All 2D IR spectra in this study were measured with our homebuilt setup described in detail previously.[43,48,49] Briefly, an optical parametric amplifier and a difference frequency generator converted 800-nm output pulses of a Ti:Sapphire amplifier to mid-IR pulses with 100-fs temporal duration, 150 $cm^{-1}$ spectral width, and a peak frequency of 1666 $cm^{-1}$. The IR pulse was split into three with wavevectors of $k_a$, $k_b$ and $k_c$ and focused onto the sample solution to induce a third-order nonlinear signal in the $-k_a+k_b+k_c$ phase-matching direction. The signal was combined with a local oscillator (LO) field and detected by spectral interferometry using a 64-element array detector with a spectral resolution of ~4 $cm^{-1}$. The time ordering of the three pulses were a-b-c and b-a-c for the rephasing (R) and nonrephasing (NR) sequences, respectively. In the measurements, the coherence time ($\tau$) was scanned from 0 to ~2.9 ps for R and to ~2.7 ps for NR with a 9-fs step, and the LO pulse preceding the signal field by 800 fs. The processing procedure for the interferometric signal has been described in Ref. 43. Polarization directions of the three IR pulses (a, b, and c for the $k_a$, $k_b$, and $k_c$ pulse) and the signal (d) are denoted as $\langle a, b, c, d \rangle$. The double-crossed polarization $\langle \pi/4, -\pi/4, Y, Z \rangle$ was employed to collect 2D IR cross-peak patterns by suppressing strong diagonal peaks. In this polarization configuration, the waiting time (T) was fixed at 0. In the measurements of 2D IR spectra under the perpendicular polarization $\langle Y, Y, Z, Z \rangle$, T was set to 300 fs to minimize the solvent nonresonant response. We also measured dispersed IR pump-probe spectra with a delay time of 300 fs, which were utilized as a reference to adjust the phase of 2D IR spectra. We conducted all of the 2D IR experiments at ambient temperature (20±1° C.).

Model Calculation of Linear and 2D IR Spectra

In the calculation of amide-I linear and 2D IR spectra, a vibrational exciton model was employed. Detailed explanations on how to construct the one- and two-exciton Hamiltonians, formulas to calculate linear and 2D IR spectra, and the orientational factors for $\langle Y, Y, Z, Z \rangle$ and $\langle \pi/4, -\pi/4, Y, Z \rangle$ have been described previously.[43,48,50] The backbone dihedral angles of the peptide were assumed to obey Gaussian distributions centered at the values determined by the X-ray diffraction analysis in this study. The standard deviation of the angles was set to 5°. The structure distribution gives rise to variations in the intramolecular C=O . . . H—N hydrogen bond geometry as well as fluctuations in the nearest-neighbor and transition dipole coupling strengths. Because the frequency of the amide-I mode depends on the strength of hydrogen bonding, the conformational fluctuations result in the inhomogeneities of the local amide-I mode frequencies. The frequency origins were set to 1693 $cm^{-1}$ for the five amide-I modes at the N-terminus, and 1685 $cm^{-1}$ for the last two modes at the C-terminus, which are exposed to solvent without forming intramolecular hydrogen bonds. These frequency values are higher than the $\omega_0$ values used in our previous work,[43] consistent with FT IR measurements of mono-substituted amides in which the amide-I mode exhibits a higher local mode frequency in $CH_2Cl_2$ than in $CHCl_3$.[51] Both of the ester and Boc urethane C=O groups were included in the model as well. We generated 10 000 different backbone conformations centered at each X-ray crystal structure and averaged the linear and 2D IR spectra calculated for each conformation. For 21, the spectra of the major and minor conformers were summed with their population weighting. The homogeneous linewidth of vibrational transitions was set to 9 $cm^{-1}$.

X-Ray Crystallography

Peptide 21 ($C_{41}H_{69}N_{11}O_{12}$, $M_w$=908.05) crystallized as colourless, plate shaped crystals in space group $P2_12_12_1$, with unit cell parameters a=16.239 (12), b=18.236 (14), c=18.655 (14), $\alpha$=90.00°, $\beta$=90.00°, $\gamma$=90.00° (orthorhombic crystal system) and Z=4. The X-ray structure was refined to a final R-factor of 0.068 for data obtained for a very small crystal (0.100 mm×0.010 mm×0.009 mm). The peptide forms a fully developed right handed $3_{10}$-helix with all possible intramolecular i→i+3 H-bonds present, including between the tert-butoxycarbonyl (Boc) group and the amide NH of Aib3 (FIG. 1).

Figure 2:
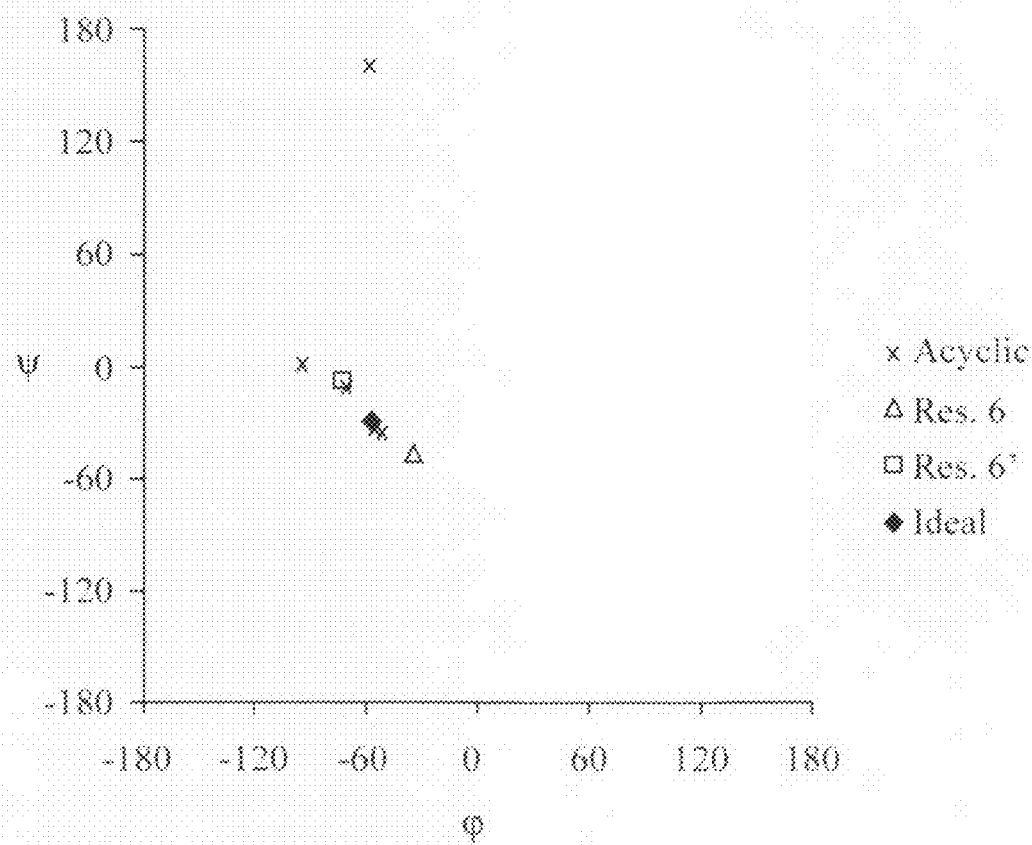
FIG. 2. is a Ramachandran plot of observed ($\phi$, $\psi$)-angles in the crystal structure of the acyclic octapeptide 21. Both conformations of Aib6 are indicated (Res. 6: major; Res. 6': minor).

With the exceptions of residues 4, 6, 7 and 8 the conformations of all remaining residues fall into the $3_{10}$-helical region of ($\phi$, $\psi$)-space, with mean absolute deviations from the ideal (i.e. average observed in peptides) $3_{10}$-helical angles of (−57°, 30°)[52] of 3.68° and 4.48° respectively (FIG. 2).

However, the dihedral angles of the two chiral, monosubstituted residues 4 and 7 deviate significantly from the ideal $3_{10}$-helical angles with [($|\Delta\phi|$, $|\Delta\psi|$)=(13.38°, 17.90°) and (36.55°, 30.96°)] respectively. Similarly large deviations from ideality, albeit slightly smaller for residue 4, were observed in the acyclic olefinic peptide of Boal et al.[25] Here residue 7 with ($\phi$, $\psi$)$_7$=(−93.55°, 0.96°) forms part of a type-I $\beta$=[53,54] together with residue 6 in its minor conformation (−72.56°, −7.39°). In contrast to the acyclic olefinic analog, where residue 8 is in the $\alpha_R$ conformation,[25] the C-terminal residue in 21 adopts a left-handed polyproline II ($P_{IIL}$) conformation with ($\phi$, $\psi$)=(−57.83°, 159.12°). This fits well, however, into the empirical pattern found in a recent survey of non-helical conformations of Aib residues in peptides. In a database of 143 crystal structures of Aib-containing helices with >3 residues with a C-terminal Aib 86.5% adopted the opposite helix sense than the rest of the molecule and 20.3% of these fell within the $P_{II}$ region.[55]

The intramolecular H-bond lengths ($d_{C=O \ldots HN}$) vary between 2.115 Å (Aib1→Aib4) and 2.341 Å (Aib3→Aib6), with mean 2.193 Å and standard deviation 0.088 Å. These values are very similar to the ones found for the acyclic olefinic analog (2.210 Å and 0.115 Å).[25] For both of these acyclic peptides the same pattern of H-bond length variations is observed. For both acyclic peptides, the longest H-bonds are between pairs of Aib residues on the N-terminal (3 and 6) and on the C-terminal (5 and 8) sides of the monosubstituted residues respectively.

The carbonyl group of Aib7 forms an intermolecular H-bond to the carbamate NH of the Boc group, but there is no intermolecular peptide-peptide H-bond to the carbonyl of the methyl ester as is often seen in structures of Aib rich peptides.[55]

Figure 3:
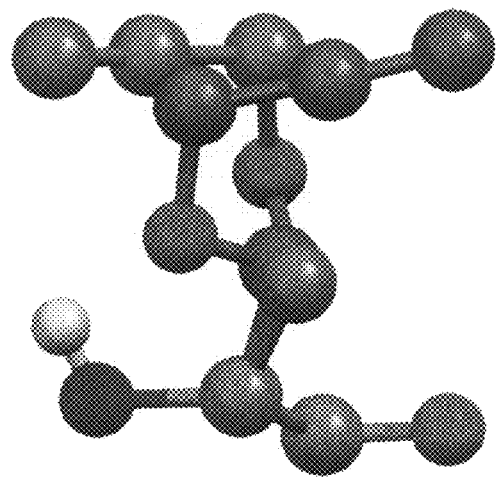
FIG. 3. shows the alkyne side chain in the acyclic peptide 21 have two different orientations in the crystal (brown: major; grey: minor). Hydrogens on the side chain atoms have been omitted for clarity.

A few features of the crystal structure of 21 unrelated to the main topic of this study merit mention. For the alkyne side chain there was some disorder, which was resolved as two different side chain orientations (FIG. 3) with occupation 0.57 (major) and 0.43 (minor).

Figure 4:
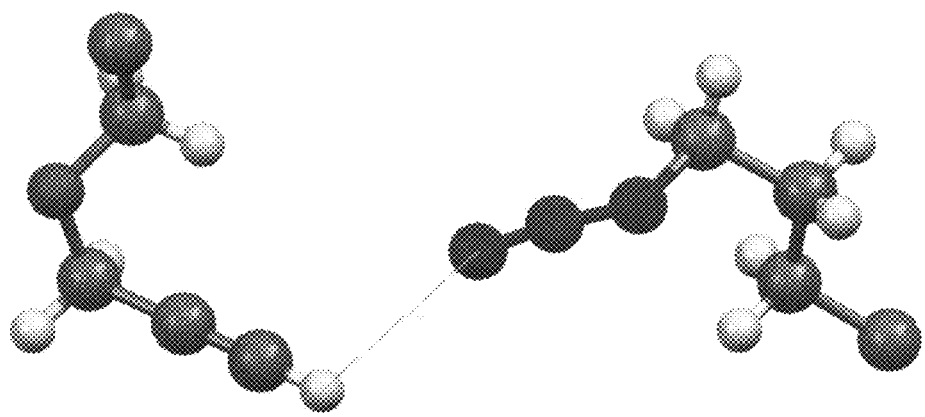
FIG. 4. shows a potentially new non-classical H-bond between an alkyne and an azido group. Only the side chains starting from $C^\alpha$ are shown.

A close contact was observed between the alkyne side chain in the minor orientation and the azido group of another molecule (FIG. 4).

Hydrogens on sp hybridized carbon atoms are well-known to be able to act as non-classical hydrogen bond donors.[56,57] The distance between the hydrogen atom and the terminal nitrogen atom of the azido group was found to be 2.78 Å, significantly longer than would be expected for a classical N—H...O=C H-bond, but similar to many observed short C—H...N contacts/H-bonds,[56] and very close to the sum of the van der Waals radii of nitrogen and hydrogen (2.75 Å). The φ angle (C—H...N) of 104.79° is very small, but not without precedence in the literature.[56] The ξ angle (H...N=N) of 139.28° is much closer to the ideal value of 120° than the φ angle is to ideality. To the best of our knowledge, this is the first time a potential non-classical H-bond between an alkyne and an azide has been observed, or for that sake could be observed, since the crystal structure of 21 appears to be the first crystal structure of a bifunctional alkyne/azide compound. However, more work is required to definitely establish the nature of this interaction.

The cyclic peptide 23 ($C_{41}H_{69}N_{11}O_{12}$, $M_w$=908.05) crystallized as colourless, plate shaped crystals in space group C2, with unit cell parameters a=36.417 (12), b=13.382 (5), c=11.873 (4), α=90.00°, β=102.360 (4)°, γ=90.00° (monoclinic crystal system) and Z=4. The X-ray structure was refined to a final R-factor of 0.039, which is unusually low for a molecule of this size.

Figure 5:
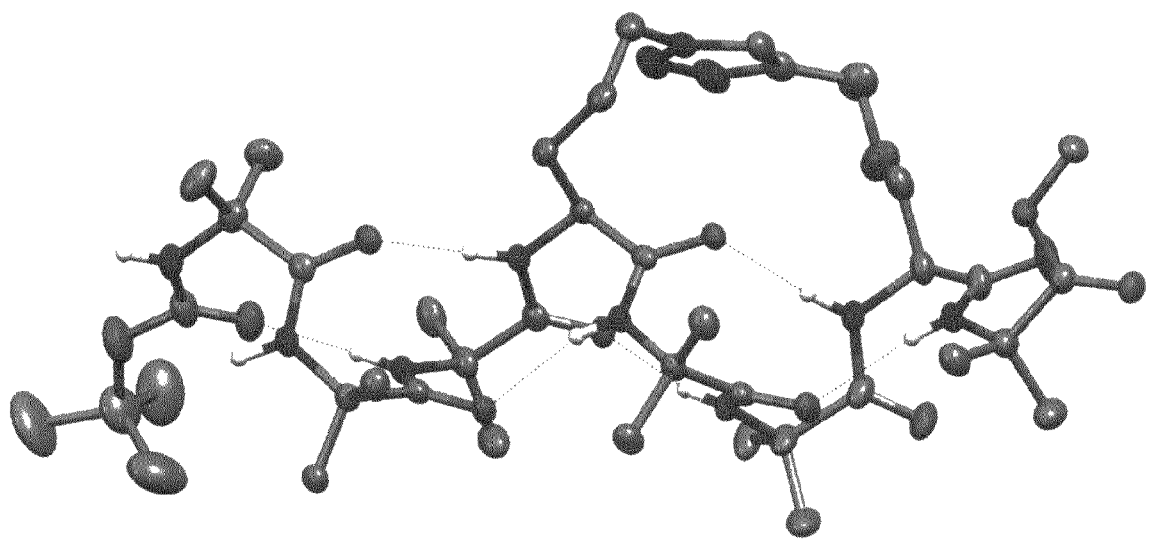
FIG. 5. is a thermal ellipsoid plot of the X-ray crystal structure of the cyclic peptide 23 at the 50% probability level with intramolecular H-bonds indicated. Apolar hydrogens have been omitted for clarity.

Like the acyclic peptide 21 the cyclic octapeptide 23 forms a fully developed right handed $3_{10}$-helix with all possible i→i+3 intramolecular H bonds present (FIG. 5).

Whereas significant deviations from an ideal $3_{10}$-helix with respect to individual dihedral angles were observed in the crystal structure of peptide 21, the structure of peptide 23 represents a strikingly ideal $3_{10}$-helix from residue 1-7. The average (φ,ψ)-angles are (−54.96°, −30.17°), deviating a mere 2.04° and 0.17° from ideality, making peptide 23 the most perfect crosslinked $3_{10}$-helix to date (Table 1).

TABLE 1

Mean (φ, Ψ)-angles with standard deviations for the crosslinked $3_{10}$-helical peptides for which crystallographic data have been reported. The dihedral angles for residue 8 have been omitted for all peptides.

| Compound | φ | σ$_φ$ | Ψ | σ$_ψ$ |
|---|---|---|---|---|
| Ideal $3_{10}$-helix | −57 | — | −30 | — |
| 21 (major) | −58.75 | 18.68 | −27.93 | 16.34 |
| 21 (minor) | −64.22 | 15.61 | −22.38 | 15.63 |
| 23 | −54.96 | 6.79 | −30.17 | 5.87 |
| Acyclic olefinic[25] | −62.32 | 15.23 | −24.29 | 10.27 |
| Cyclic olefinic[25] | −68.35 | 24.04 | −16.94 | 24.50 |
| Cyclic hydrogen.[25] | −59.99 | 14.94 | −27.52 | 15.59 |
| Acyclic Api[26] | −54.20 | 4.35 | −28.97 | 8.07 |
| Cyclic Api (mol.1)[26] | −55.52 | 2.61 | −26.77 | 6.11 |
| Cyclic Api (mol.2)[26] | −54.94 | 3.83 | −27.73 | 7.20 |

Figure 6:
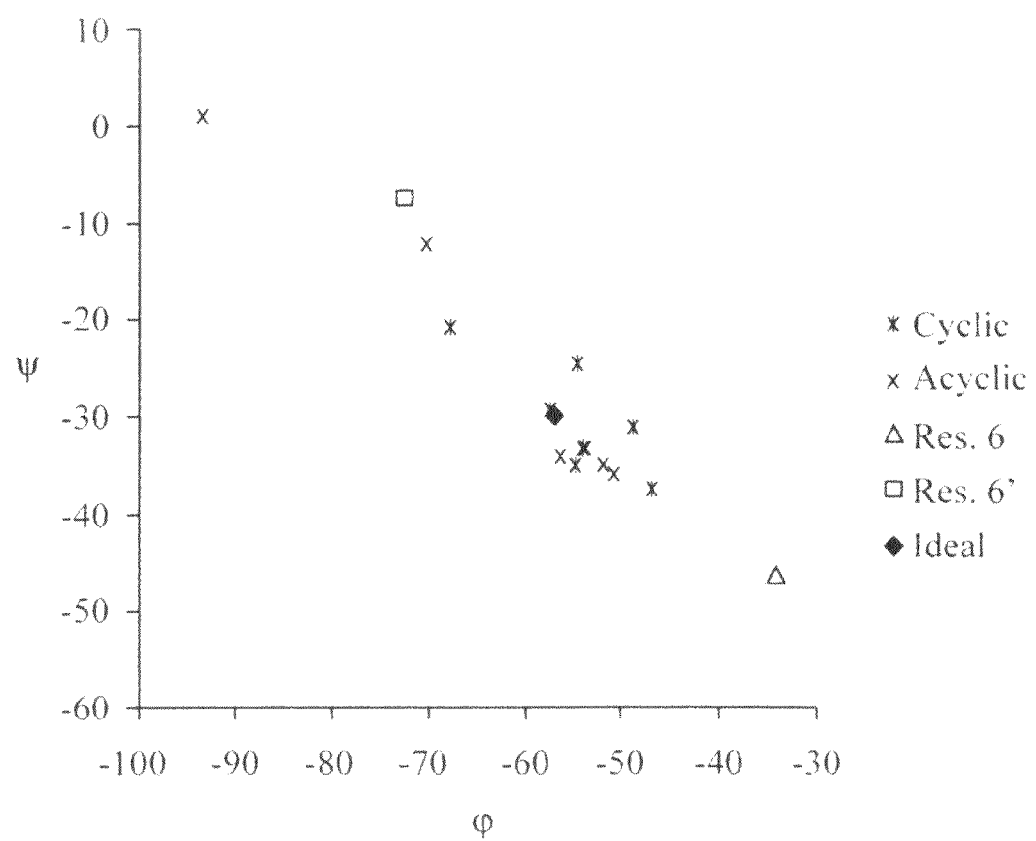
FIG. 6. is a partial Ramachandran plot for residue 1-7 of 21 and 23. Both positions of Aib6 in the crystal structure of 21 are indicated (Res. 6: major; Res. 6': minor).

Importantly, the triazole bridge appears to strongly enforce a $3_{10}$-helical conformation for residues 4, 6 and 7, effectively removing these as outliers in the Ramachandran plot (FIG. 6). The deviations from ideality for these residues in peptide 23 are (|Δφ|, |Δψ|)=(2.21°, 4.88°); (0.51°, 0.78°) and (10.93°, 9.25°), respectively, dramatically improved relative to 21. This is opposite to the trend observed in the structures of the cyclic olefinic peptide and its hydrogenated analog, where cyclization appeared to cause larger or unchanged deviations, with (φ, ψ)$_4$=(−96.57°, 19.84°) and (−66.64°, −22.33°) and (φ, ψ)$_7$=(−108.91°, 13.69°) and (−90.06°, 3.05°, respectively.[25]

The residues of the p-phenylene diacetic acid crosslinked Api/Aib peptide generally have close to ideal dihedral angles from residue 1 through to 7, but residue 4 (next to the first Api residue) has a slightly distorted ψ-angle (−22.69°) and the deviation from the ideal ψ-angle for residue 6 (−14.26°, |Δψ|=15.74°) is larger than any φ/ψ-deviation for 23.[26]

Figure 7:
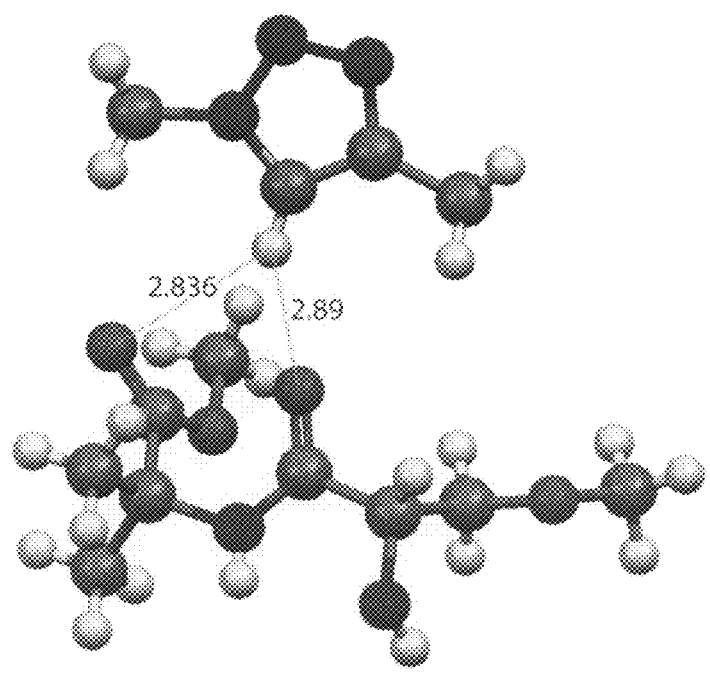
FIG. 7. shows the triazole proton of one molecule forms a bifurcated non-classical H-bond with residues 7 and 8 in another molecule. Only one of the two bifurcated H-bonds between two peptide molecules is shown. The remainder of the molecules has been omitted for clarity.

The C-terminal residue adopts an $α_L$ conformation, in other words the opposite helix sense as the rest of the molecule. This is statistically the most common conformation for a C-terminal Aib in Aib rich helices with >3 residues and is often due to head-to-tail intermolecular interactions with the Boc group in capped peptides or with solvent.[55] Interestingly, in the structure of 23 the dihedral angles of (46.80°, 49.93°) allow two peptide molecules to contact each other in a tail-to-tail fashion forming two bifurcated non-classical C—H...O=C H-bonds between the triazole hydrogen and the carbonyl groups of residues 7 and 8 (FIG. 7). This underlines a potential added advantage of a triazole in a helix stabilizing bridge, namely its ability to make useful contacts to peptides/proteins. The triazole is approximately coplanar with the bifurcated H-bond. Interestingly, all the Api peptides,[26] which also are highly $3_{10}$-helical at residue 7, have C-terminal residues with very similar conformation to peptide 23.

The overall similarity to an ideal $3_{10}$-helix is also reflected in significantly shorter intramolecular H-bonds compared to 21 and the hydrocarbon stapled analogs (Table 2). The data for 21 refer to the structure with the alkyne side chain in its major orientation and the backbone in its major conformation.

TABLE 2

Mean O...H distances with standard deviations for the intramolecular H-bonds in the crystal structures of 21 and 23. Positional parameters for amide H atoms were refined for 23 only. To facilitate comparison with 21, values are included for 23 after normalization of all N—H bonds to 0.880 Å (i.e. H atoms are moved along the covalent bond vectors so as to make the N—H distances equal to 0.880 Å, the fixed N—H distance used in the refinement of 21).

| Compound | O...H | σ | O...H* | σ* |
|---|---|---|---|---|
| 21 | 2.193 | 0.088 | 2.164 | 0.056 |
| 23 | 2.118 | 0.075 | 2.102 | 0.071 |
| 23 (scaled) | 2.087 | 0.084 | 2.058 | 0.051 |
| Acyclic olefinic[25] | 2.210 | 0.115 | | |
| Cyclic olefinic[25] | 2.384 | 0.760 | 2.075 | 0.357 |
| Cyclic hydrogen.[25] | 2.335 | 0.195 | 2.257 | 0.034 |

*The longest H-bond, i.e. between residue 4 and 7 for 23 and between 3 and 6 for 21 and the hydrocarbon stapled peptides, have been omitted.

As expected the longest H-bond observed in the structure of 23 is between residues 4 and 7 (2.232 Å, Δ=+0.103 Å), whose conformations change the most as they are pulled in towards more ideal $3_{30}$-helical dihedral angles. However, all the remaining 5 intramolecular H-bonds are shorter in 23 than in 21. The largest improvements are seen for Boc→Aib3 (Δ=−0.172 Å), Aib3→Aib6 (Δ=−0.193 Å) and Aib5→Aib8 (Δ=−0.184 Å). Interestingly, the Aib3→Aib6 H-bond is the one stretched the most in the cyclic hydrocarbon stapled peptides relative to their acyclic precursor (Δ=+0.386 Å and Δ=1.585 Å), and is in fact broken in the cyclic olefinic peptide ($d_{O...H}$=3.927 Å).[25]

NMR Spectroscopy

The 2D ROESY spectra of the octapeptides 21 and 23 in the polar aprotic solvent $CD_2Cl_2$ clearly demonstrated the presence of all possible NH(i)→NH(i+1) ROEs, and the only possible medium range $C^\alpha$H(i)→NH(i+2) and long range $C^\alpha$H(i)→NH(i+3) ROEs, which are indicative of $3_{10}$- or α-helical peptides.[58-60]

Measurement and Simulation of 2D IR Spectra in Polar Aprotic Solvent

Conventional linear IR response of the amide-I mode is widely used to obtain structural information of polypeptides.[61] Going beyond 1D, 2D IR spectroscopy measures nonlinear response of the mode, which has higher sensitivity to the underlying biomolecular structure.[62-64] In this study we measured FT IR and 2D IR spectra of 21 and 23 in $CH_2Cl_2$ to obtain insights into the conformation of these peptides in polar aprotic solvent. Also, the spectral profiles were simulated based on crystal structures established by the X-ray diffraction analysis. The top panels in FIGS. 8a and b show the measured FT IR spectra (black solid) of 21 and 23, respectively, in $CH_2Cl_2$ (~6 mM, a thickness of 180 μm). The spectra were normalized by the peak absorbance of the methyl ester C=O band at 1738 cm$^{-1}$ after subtracting the solvent spectrum. We assign the small band at 1701 cm$^{-1}$ to the urethane C=O of the N-terminus Boc group and the broad band at 1662 cm$^{-1}$ to the amide-I modes. The line shapes of the amide-I bands of the two peptides are slightly different, more rounded at the peak for 23 but pointy for 21. The full-width-half-maxima are 27.7 and 30.8 cm$^{-1}$, respectively. It is not straightforward, however, to infer from the linear spectra whether 21 and 23 in $CH_2Cl_2$ maintain the same $3_{10}$-helical conformation as observed in the crystal states, or if their structures have changed to other conformations, such as α-helix and $P_{II L}$.

Figure 8:
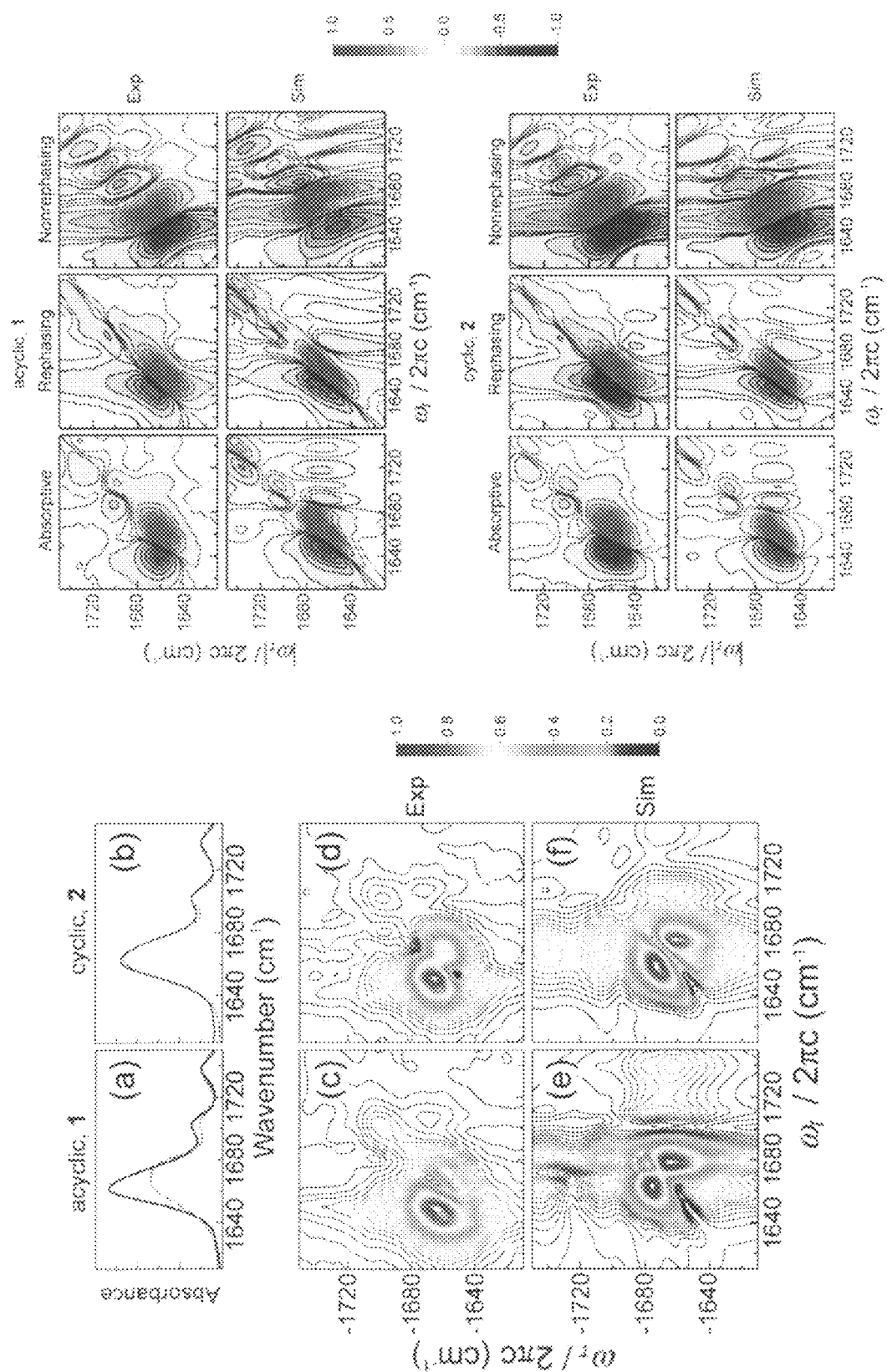
FIG. 8. (a, b) shows a measured (black solid) and simulated (red dashed) linear IR spectra for 21 and 23. (c, d) 2D IR cross-peak patterns in $CH_2Cl_2$ observed under the double-crossed polarization configuration. (e, f) Simulated cross-peak patterns based on the peptide backbone conformations of 21 and 23 in the crystal state. Shown on the right are the measured and simulated absorptive and the real parts of the rephasing and nonrephasing 2D IR spectra under the perpendicular polarization configuration.

The absorptive and the real parts of rephasing and nonrephasing 2D IR spectra of 21 and 23 measured under the ⟨Y, Y, Z, Z⟩ polarization configuration are shown on the right in FIG. 8. The three positive peaks along the diagonal line of the absorptive spectrum correspond to the 0-1 transitions, whereas the three negative peaks are the 1-2 transitions, which are anharmonically shifted from the 0-1 in the $\omega_t$ direction. For the rephasing and nonrephasing spectra, the nodal lines between the 0-1 and 1-2 transitions are parallel and perpendicular to the diagonal, respectively. These 2D IR spectra look almost indistinguishable between 21 and 23.

The amide-I 2D IR cross-peak pattern obtained under the double-crossed polarization can much more sensitively distinguish subtle structural differences, for example, between $3_{10}$- and α-helices.[48,49] In general, the experimental and simulated 2D profile exhibits a doublet pattern for the former and a multiple-peak pattern for the latter.[49,50] FIGS. 8c and d presents the absolute magnitude cross-peak patterns of 21 and 23, respectively. A doublet clearly shows up in the amide-I region. Weak cross-peaks between the amide-I and the urethane C=O modes are also observed. The doublet pattern of 21 is similar to that of 23 but some subtle differences can also be noticed. For 23, the line shape and relative intensity of the lower diagonal peak to the upper peak (0.68) are very close to those observed for other $3_{10}$-helical peptides with Aib and (αMe)Val residues.[48,49] For 21, the two peaks in the doublet are more elongated along the diagonal, merged into each other at a lower frequency, and their intensity ratio is 0.45. This result suggests that 21 and 23 are both $3_{10}$-helical in the solution but their structures are slightly different. It is conceivable that 21 may be more disordered than 23 because it lacks the side chain-to-side chain CuAAC constraint. Our previous theoretical study shows that the rephasing cross-peak pattern differs from a doublet with the appearance of extra features as the peptide conformation increasingly deviates from an ideal $3_{10}$-helix.[50] The absence of extra features suggests that the structural difference between 21 and 23 is small in $CH_2Cl_2$ despite the quite different dihedral angles of the residues 4, 6, and 7 observed in the crystal state.

To further address these points, we performed model calculations to examine how similar or different the 2D IR spectral patterns would be if the crystal structures are preserved in solution. FIGS. 8e and f presents the simulated 2D IR cross-peak pattern using an ensemble of peptide structures with the backbone dihedral angles in Gaussian distributions centered at the crystal structures of 21 and 23, respectively. The simulated 2D IR pattern of 23 shows a clear amide-I doublet along with some cross-peaks between the amide-I and the capping C=Os. The linear IR spectrum (FIG. 8b, red dashed) and 2D absorptive and the real parts of the rephasing and nonrephasing spectra (FIG. 8, bottom panels on the right) were also calculated using the same parameters, and the agreement with the experimental spectrum is quite good. On the contrary, the crystal structure of 21 gave rise to quite different linear and 2D IR spectra from those of 23. The calculated linear spectrum of the major backbone conformer consists of two overlapping, broad amide-I bands with the lower frequency band having a stronger peak intensity. The linear spectrum of the minor backbone conformer also exhibits two bands with an opposite trend in the peak intensity. The population weighted spectrum (FIG. 8a) shows hints of overlapping features. The cross-peak pattern in FIG. 8e exhibits a more spread doublet with additional shoulders than that characteristic of an ideal $3_{10}$-helix. Note that the simulated cross-peak pattern is still different from the ideal α-helix conformation [(ϕ, ψ)=(−63°, −42°)] we obtained previously.[48,49] Also, the calculated 2D absorptive spectrum of 21 is much more elongated along the diagonal than that of 23. The experimental and simulation results indicate that the different backbone conformations of 21 and 23 in the crystal state are no longer preserved in $CH_2Cl_2$.

In summary, the feasibility of side chain-to-side chain crosslinking by CuAAC in a $3_{10}$-helical Aib rich peptide has been demonstrated. An attractive feature of the cyclic product 23 is its significantly higher aqueous solubility (>1 mM) compared to 21. 2D IR and 2D ROESY experiments confirmed that the cyclic peptide 23 retained a $3_{10}$-helical structure in the apolar solvent $CD_2Cl_2$. The first X-ray crystallographic investigation of a helical peptide with a triazole derived crosslink has revealed that 23 is the most perfect crosslinked $3_{10}$-helical peptide so far studied in the crystal state, with mean (ϕ, ψ)-angles deviating less than 2° from ideality.

The closeness to ideality of the conformational angles in the solid state and the thermal stabilization of the $3_{10}$-helical state achieved strongly suggests that the CuAAC side chain-to-side chain crosslinking methodology may have significant utility applied to peptides and peptidomimetics of interest in chemical biology and biomedicine, in particular to synthetic analogs of the Pro138-Gly144 segment of human AQP4.[17]

REFERENCES (1) Vernall, A. J.; Cassidy, P.; Alewood, P. F. *Angew. Chem. Int. Ed.* 2009, 48 (31), 5675.

(2) Munoz, V.; Blanco, F. J.; Serrano, L. *Nat. Struct. Biol.* 1995, 2 (5), 380.

(3) Scholtz, J. M.; Qian, H.; Robbins, V. H.; Baldwin, R. L. *Biochemistry* 1993, 32 (37), 9668, and references therein.

(4) Jackson, D. Y.; King, D. S.; Chmielewski, J.; Singh, S.; Schultz, P. G. *J. Am. Chem. Soc.* 1991, 113, 9391.
(5) Phelan, J. C.; Skelton, N. J.; Braisted, A. C.; McDowell, R. S. *J. Am. Chem. Soc.* 1997, 119, 455, and references therein.
(6) Blackwell, H. E.; Grubbs, R. H. *Angew. Chem. Int. Ed.* 1998, 37 (23), 3281.
(7) Schafineister, C. E.; Po, J.; Verdine, G. L. *J. Am. Chem. Soc.* 2000, 122, 5891.
(8) Young-Woo, K.; Verdine, G. L. *Bioorg. Med. Chem. Lett.* 2009, 19 (9), 2533.
(9) Walensky, L. D.; Kung, A. L.; Escher, I.; Malia, T. J.; Barbuto, S.; Wright, R. D.; Wagner, G.; Verdine, G. L.; Korsmeyer, S. J. *Science* 2004, 305 (5689), 1466.
(10) Ebert, M.-O.; Gardiner, J.; Ballet, S.; Abell, A. D.; Seebach, D. *Helv. Chim. Acta* 2009, 92 (12), 2643.
(11) Toniolo, C.; Brückner, H. (eds.) *Peptaibiotics: Fungal Peptides Containing alpha-Dialkyl alpha-Amino Acids*, Wiley-VCH, 2009.
(12) Millhauser, G. L. *Biochemistry* 1995, 34 (12), 3873.
(13) Manley, G. T.; Fujimura, M.; Ma, T.; Noshita, N.; Fliz, F.; Bollen, A. W.; Chan, P.; Verkman, A. S, *Nat. Med. (N.Y.)* 2000, 6 (2), 159.
(14) Vajda, Z.; Pedersen, M.; Fuchtbauer, E.-M., Wertz, K.; Stodkilde-Jorgensen, H.; Sulyok, E.; Doczi, T.; Neely, J. D.; Agre, P.; Frokiaer, J.; Nielsen, S. *Proc. Nat. Acad. Sci. U.S.A.* 2002, 99 (20), 13131.
(15) Amiry-Moghaddam, M. R.; Otsuka, T.; Hurn, P. D.; Traystman, R. J.; Haug, F. M.; Stanley, S. C.; Adams, M. E.; Neely, J. D.; Agre, P.; Ottersen, O. P.; Bhardwaj, A. *Proc. Nat. Acad. Sci. U.S.A.* 2003, 100 (4), 2106.
(16) Amiry-Moghaddam, M.; Ottersen, O. P. *Nat. Rev. Neurosci.* 2003, 4 (12), 991.
(17) Jacobsen, Ø.; Klaveness, J.; Ottersen, O. P.; Amiry-Moghaddam, M. R.; Rongved, P. *Org. Biomol. Chem.* 2009, 7 (8), 1599.
(18) Tani, K.; Mitsuma, T.; Hiroaki, Y.; Kamegawa, A.; Nishikawa, K.; Tanimura, Y.; Fujiyoshi, Y. *J. Mol. Biol.* 2009, 389 (4), 694.
(19) Engel, A.; Fujiyoshi, Y. *Curr. Opin. Struct. Biol.* 2008, 18 (2), 229.
(20) Hiroaki, Y.; Tani, K.; Kamegawa, A.; Gyobu, N.; Nishikawa, K.; Suzuki, H.; Walz, T.; Sasaki, S.; Mitsuoka, K.; Kimura, K.; Mizoguchi, A.; Fujiyoshi, Y. *J. Mol. Biol.* 2006, 355 (4), 628.
(21) Schievano, E.; Pagano, K.; Mammi, S.; Peggion, E. *Biopolymers* 2005, 80 (2 and 3), 294.
(22) Curran, T. P.; Handy, E. L. *J. Organomet. Chem.* 2009, 694 (6), 902.
(23) Madden, M. M.; Rivera Vera, C. I.; Song, W.; Lin, Q. *Chem. Commun.* 2009, (37), 5588.
(24) Blackwell, H. E.; Sadowsky, J. D.; Howard, R. J.; Sampson, J. N.; Chao, J. A.; Steinmetz, W. E.; O'Leary, D. J.; Grubbs, R. H. *J. Org. Chem.* 2001, 66 (16), 5291.
(25) Boal, A. K.; Guryanov, I.; Moretto, A.; Crisma, M.; Lanni, E. L.; Toniolo, C.; Grubbs, R. H.; O'Leary, D. J. *J. Am. Chem. Soc.* 2007, 129, 6986.
(26) Ousaka, N.; Sato, T.; Kuroda, R. *J. Am. Chem. Soc.* 2008, 130 (2), 463.
(27) Bavoso, A.; Benedetti, E.; Di Blasio, B.; Pavone, V.; Pedone, C.; Toniolo, C.; Bonora, G. M. *Proc. Nat. Acad. Sci. U.S.A.* 1986, 83 (7), 1988.
(28) Kolb, H. C.; Finn, M. G.; Sharpless, K. B. *Angew. Chem. Int. Ed.* 2001, 40 (11), 2004.
(29) Tornøe, C. W.; Meldal, M. *Peptides 2001, Proc. Am. Pept. Symp.*; American Peptide Society and Kluwer Academic Publishers: San Diego, 2001, pp. 263-264.
(30) Tornøe, C. W.; Christensen, C.; Meldal, M. *J. Org. Chem.* 2002, 67 (9), 3057.
(31) Rostovtsev, V. V.; Green, L. G.; Fokin, V. V.; Sharpless, B. K. *Angew. Chem. Int. Ed.* 2002, 41 (14), 2596.
(32) Meldal, M.; Tornøe, C. W. *Chem. Rev.* 2008, 108 (8), 2952.
(33) Cantel, S.; Le Chevalier Isaad, A.; Scrima, M.; Levy, J. J.; DiMarchi, R. D.; Rovero, P.; Halperin, J. A.; D'Ursi, A. M.; Papini, A. M.; Chorev, M. *J. Org. Chem.* 2008, 73 (15), 5663.
(34) Scrima, M.; Le Chevalier-Isaad, A.; Rovero, P.; Papini, A. M.; Chorev, M.; D'Ursi, A. M. *Eur. J. Org. Chem.* 2010, (3), 446.
(35) Holub, J. M.; Jang, H.; Kirshenbaum, K. *Org. Lett.* 2007, 9 (17), 3275.
(36) Bourne, Y.; Kolb, H. C.; Radic, Z.; Sharpless, K. B.; Taylor, P.; Marchot, P. *Proc. Nat. Acad. Sci. U.S.A.* 2004, 101, 1449.
(37) Whiting, M.; Muldoon, J.; Lin, Y. C.; Silverman, S. M.; Lindstron, W.; Olson, A. J.; Kolb, H. C.; Finn, M. G.; Sharpless, K. B.; Elder, J. H.; Fokin, V. V. *Angew. Chem. Int. Ed.* 2006, 45, 1435.
(38) Tornøe, C. W.; Sanderson, S. J.; Mottram, J. C.; Coombs, G. H.; Meldal, M. *J. Comb. Chem.* 2004, 6, 312.
(39) Le Chevalier Isaad, A.; Barbetti, F.; Rovero, P.; D'Ursi, A. M.; Chelli, M.; Chorev, M.; Papini, A. M. *Eur. J. Org. Chem.* 2008, (31), 5308.
(40) Goddard-Borger, E. D.; Stick, R. V. *Org. Lett.* 2007, 9 (19), 3797.
(41) Ten Brink, H. T.; Rijkers, D. T. S.; Liskamp, R. M. J. *J. Org. Chem.* 2006, 71 (5), 1817.
(42) Sugano, H.; Miyoshi, M. *J. Org. Chem.* 1976, 41 (13), 2352.
(43) Maekawa, H.; Formaggio, F.; Toniolo, C.; Ge, N.-H. *J. Am. Chem. Soc.* 2008, 130 (20), 6556.
(44) Langille, N. F.; Jamison, T. F. *Org. Lett.* 2006, 8 (17), 3761.
(45) Nishizawa, Y. *Bull. Chem. Soc. Jpn.* 1961, 34, 1170.
(46) Jagasia, R.; Holub, J. M.; Bollinger, M.; Kirshenbaum, M.; Finn, M. G. *J. Org. Chem.* 2009, 74 (8), 2964.
(47) Roice, M.; Johannsen, I.; Meldal, M. *QSAR Comb. Sci.* 2004, 23, 662.
(48) Maekawa, H.; Toniolo, C.; Broxterman, Q. B.; Ge, N.-H. *J. Phys. Chem. B* 2007, 111, 3222.
(49) Maekawa, H.; Toniolo, C.; Moretto, A.; Broxterman, Q. B.; Ge, N.-H. *J. Phys. Chem. B* 2006, 110, 5834.
(50) Sengupta, N.; Maekawa, H.; Zhuang, W.; Toniolo, C.; Mukamel, S.; Tobias, D. J.; Ge, N.-H. *J. Phys. Chem. B* 2009, 113, 12037.
(51) Fillaux, F.; De Lozé, C. *Biopolymers* 1972, 11, 2063.
(52) Toniolo, C.; Benedetti, E. *Trends Biochem. Sci.* 1991, 16 (9), 350.
(53) Chou, P. Y.; Fasman, G. D. *J. Mol. Biol.* 1977, 115, 135.
(54) Venkatachalam, C. M. *Biopolymers* 1968, 6, 1425.
(55) Aravinda, S.; Shamala, N.; Balaram, P. *Chem. Biodivers.* 2008, 5, 1238.
(56) Taylor, R.; Kennard, O. *J. Am. Chem. Soc.* 1982, 104 (19), 5063.
(57) Sutor, D. J. *Nature* 1962, 195, 68.
(58) Rai, R.; Aravinda, S.; Kanagarajadurai, K.; Raghothama, S.; Shamala, N.; Balaram, P. *J. Am. Chem. Soc.* 2006, 128 (24), 7916.
(59) Williams, D. H.; Fleming, I. *Spectroscopic Methods in Organic Chemistry*, 5th Edition, McGraw-Hill, 1995, pp. 140.
(60) Wüthrich, K. *NMR of Proteins and Nucleic Acids*, John Wiley & Sons: New York, 1986.

(61) Krimm, S.; Bandekar, *J. Adv. Protein Chem.* 1986, 38, 181.
(62) Zhuang, W.; Hayashi, T.; Mukamel, S. *Angew. Chem. Int. Ed.* 2009, 48, 3750.
(63) Kim, Y. S.; Hochstrasser, R. M. *J. Phys. Chem. B* 2009, 113, 8231.
(64) Hunt, N. T. *Chem. Soc. Rev.* 2009, 38, 1837.

Abbreviations

PyBOP (Benzotriazol-1-yloxy)tripyrrolidinophosphonium hexafluorophosphate
DIPEA N,N-Diisopropylethylamine
EDC N-(3-Dimethylaminopropyl)-N'-ethylcarbodiimide
HOAt 1-Hydroxy-7-azabenzotriazole
HOBt Hydroxybenzotriazole
TFA Trifluoroacetic acid
TFE 2,2,2-Trifluoroethanol Synthesis Schemes

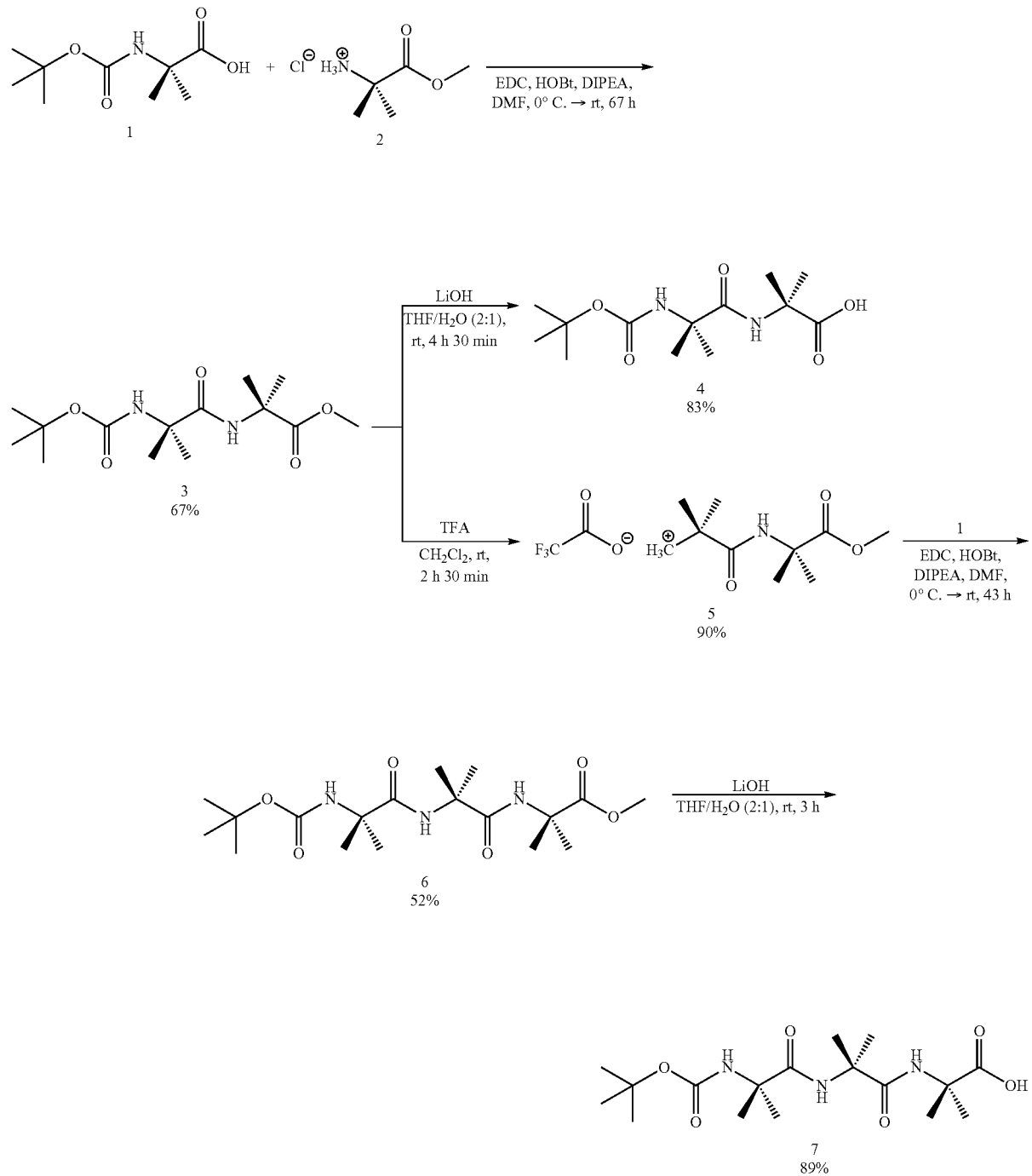

Scheme 2 Synthesis of the key building block $N^{\alpha}$-Boc-ε-azido-L-norvaline 11
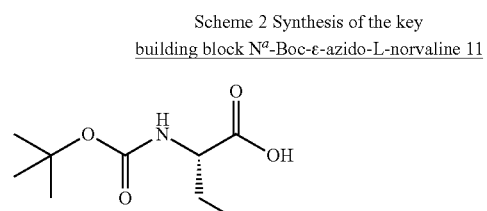
8
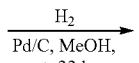
-continued
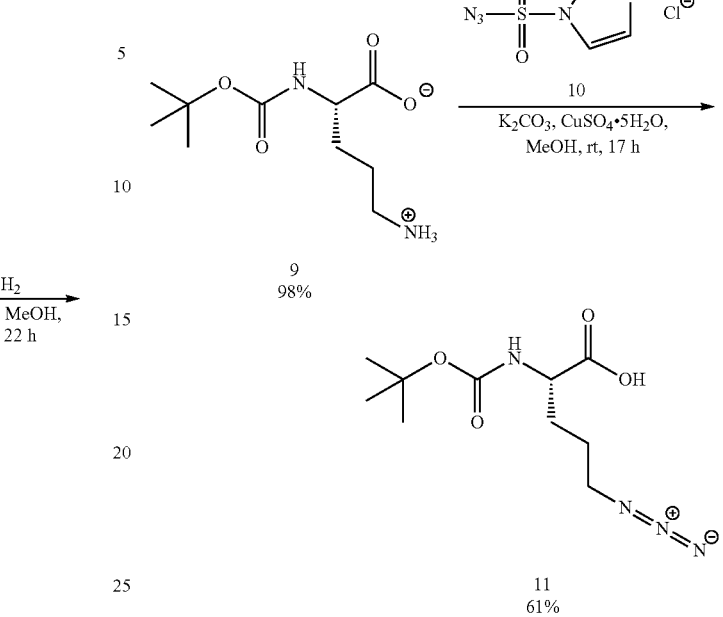

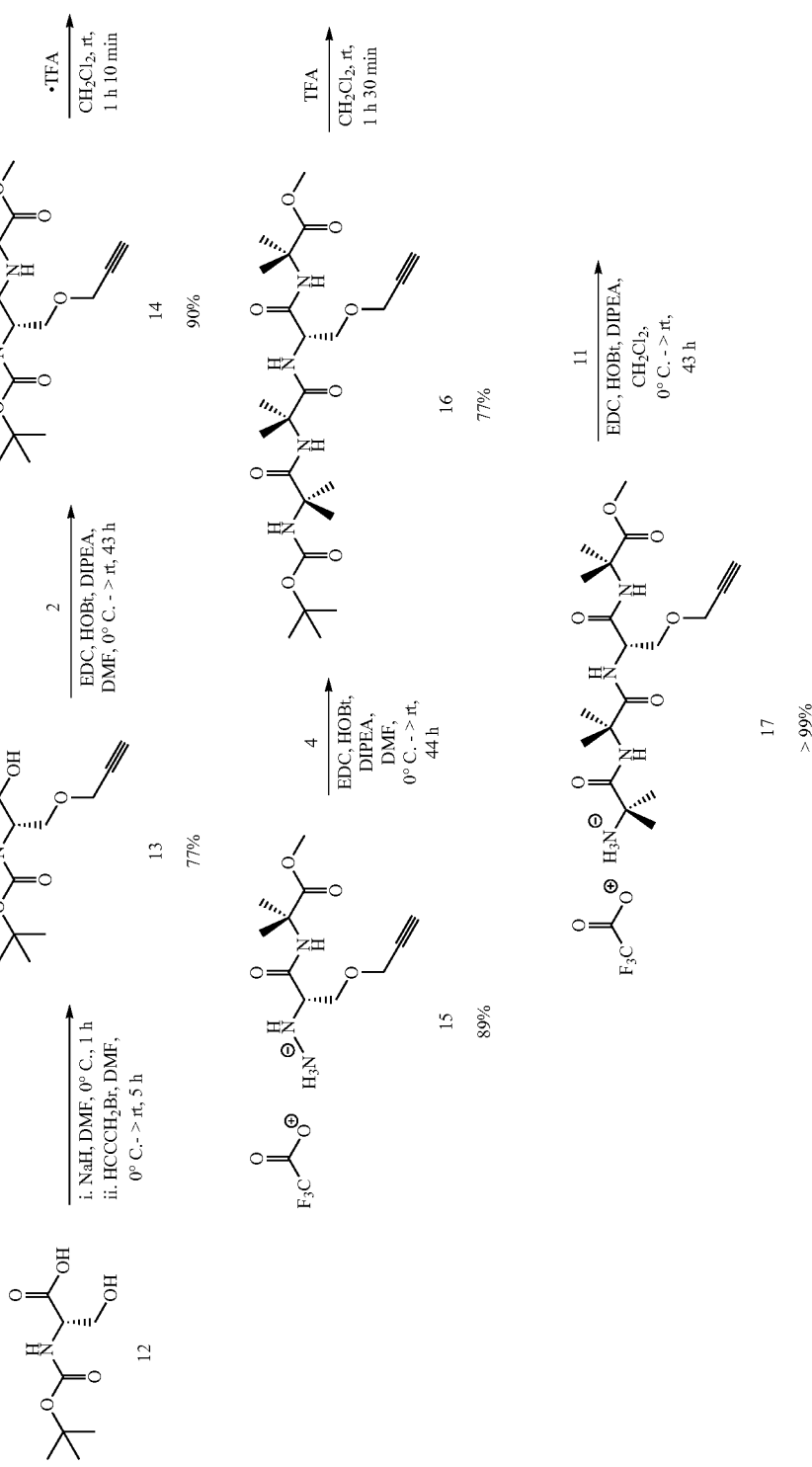
Scheme 3 Synthesis of the C-terminal pentapeptide fragments 19 and 22 and segment condensation with 7 to form 21 and 23

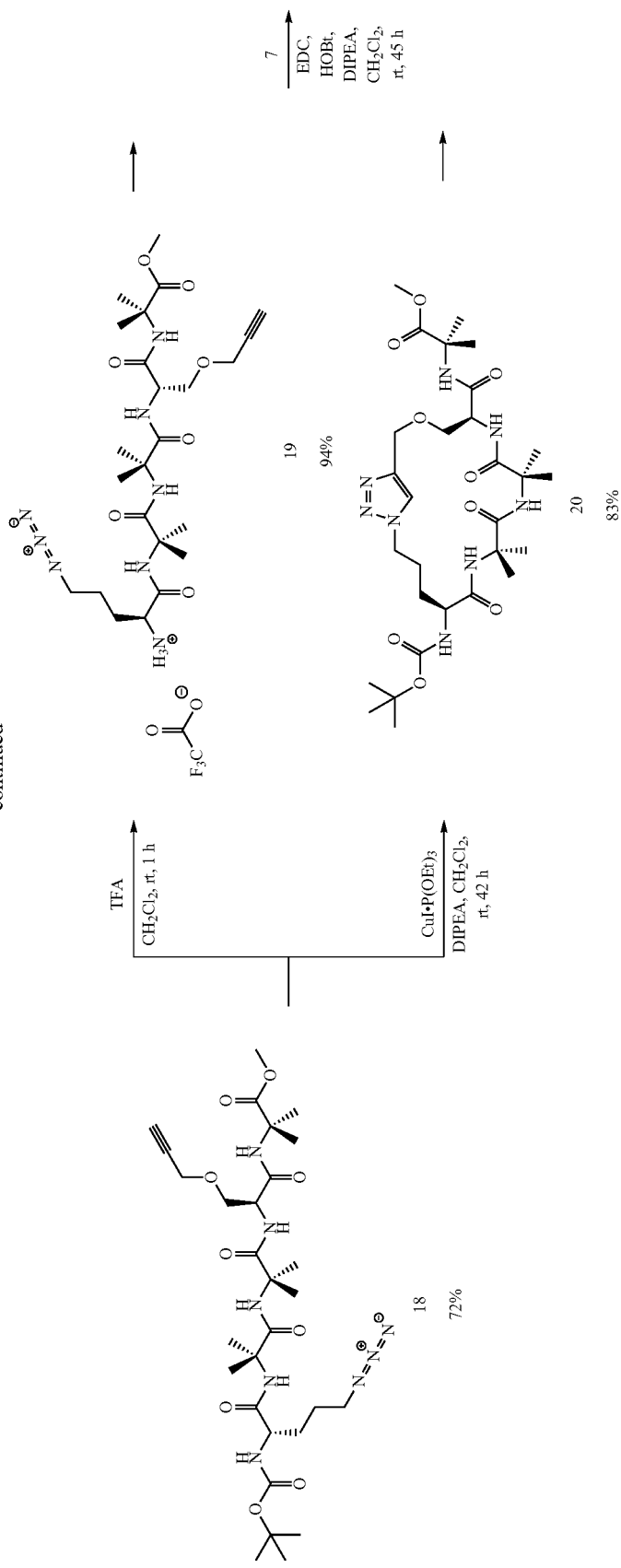

-continued
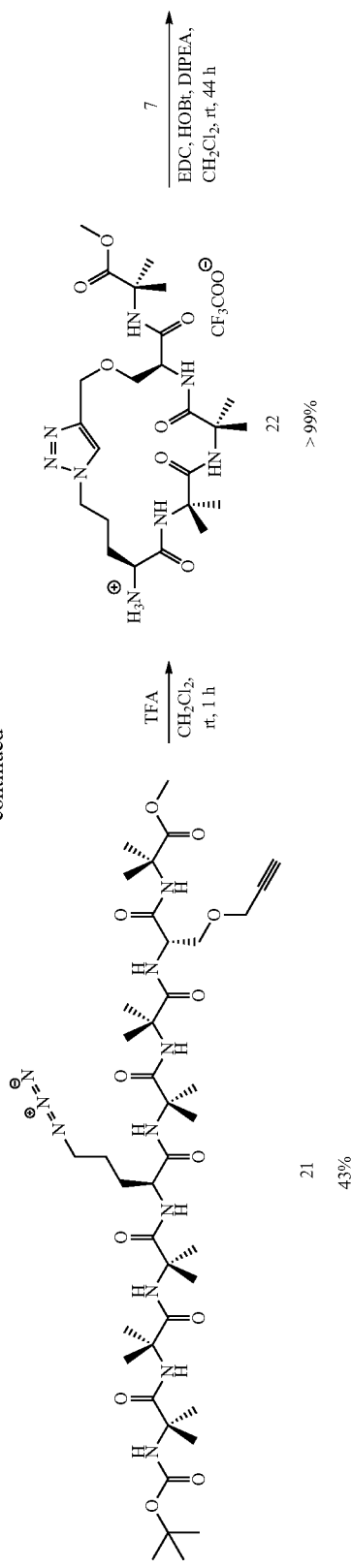
21
43%
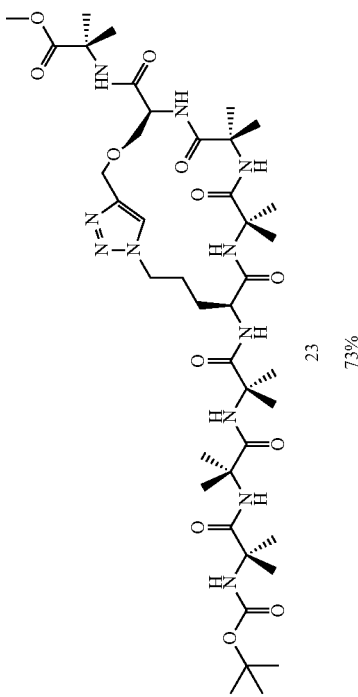
22
>99%
23
73%

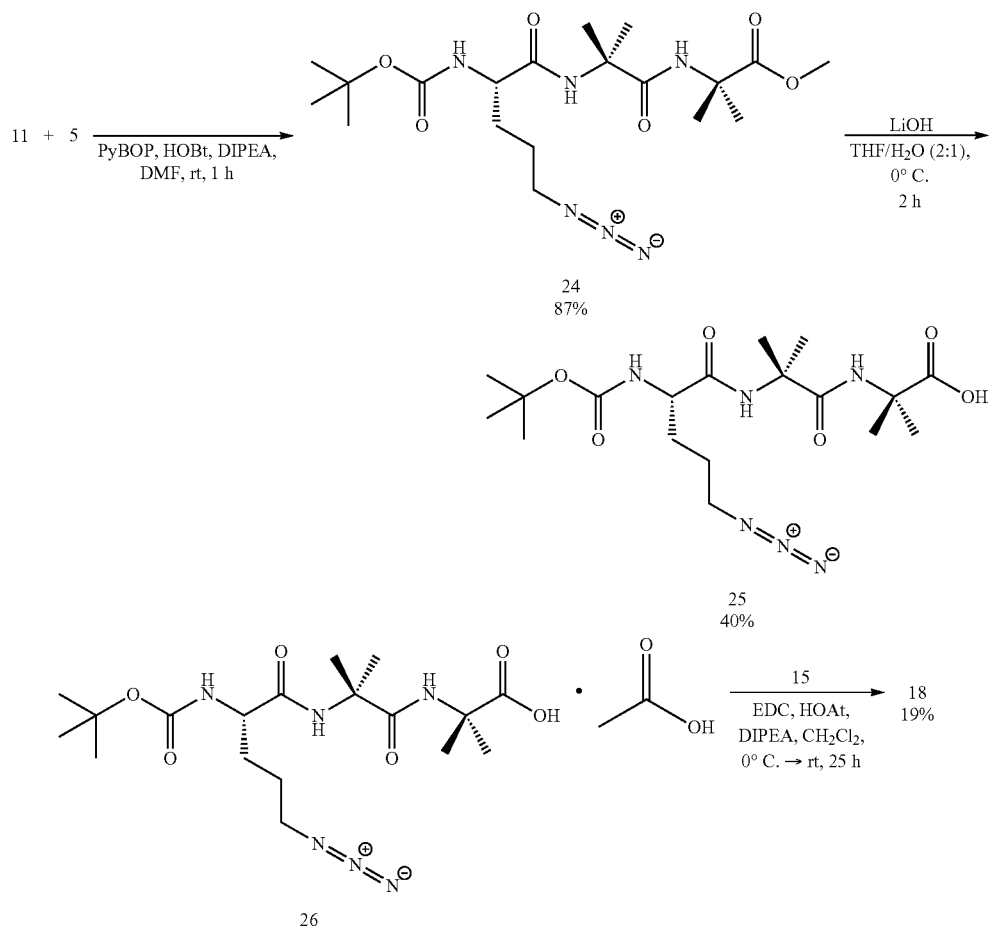
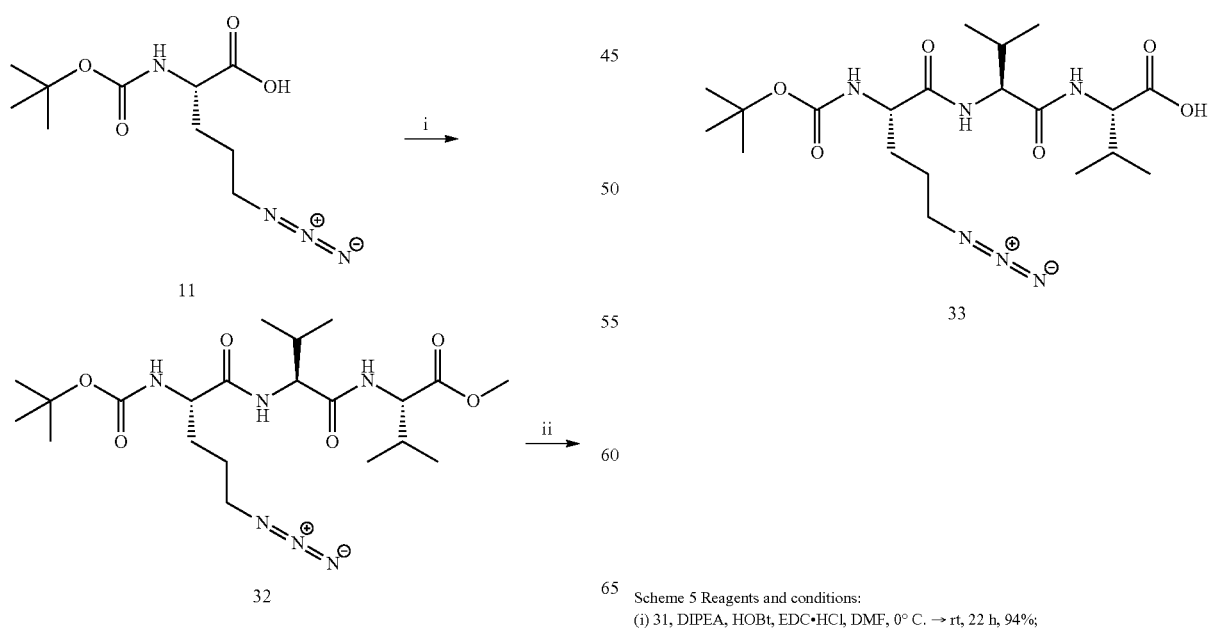
Scheme 5 Reagents and conditions:
(i) 31, DIPEA, HOBt, EDC·HCl, DMF, 0° C. → rt, 22 h, 94%;
(ii) LiOH, THF/H₂O (2:1), 0° C., 3 h, 62%.

Scheme 6 Synthesis of 34
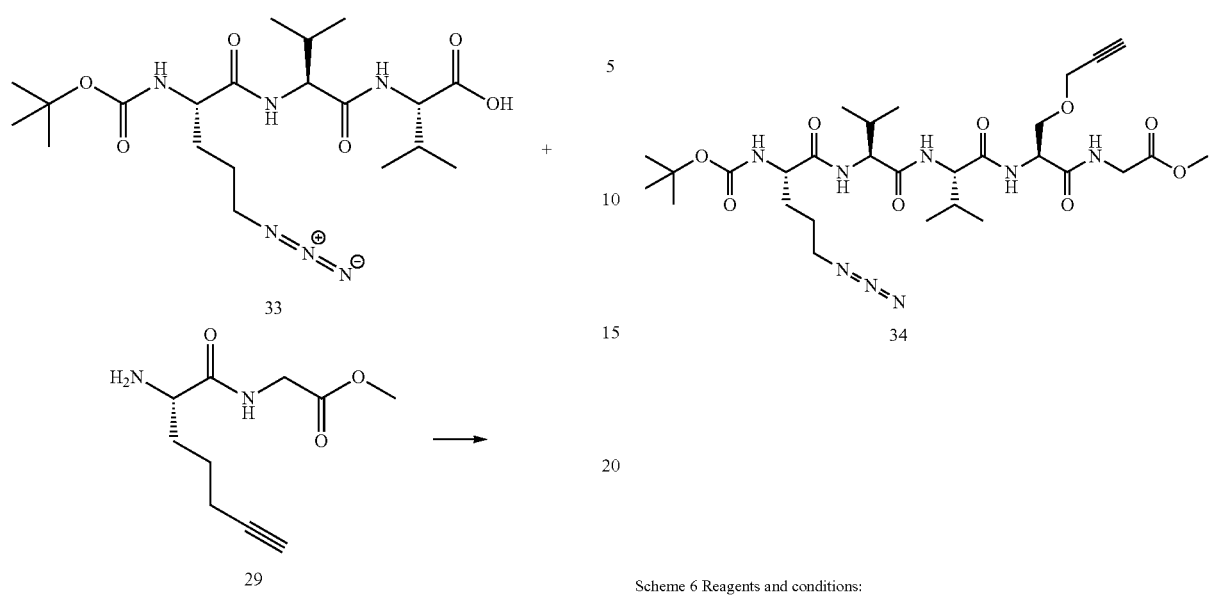
Scheme 6 Reagents and conditions:
(i) HOBt, EDC•HCl, CH$_2$Cl$_2$, rt, 21 h, 69%
Scheme 7 Synthesis of 35
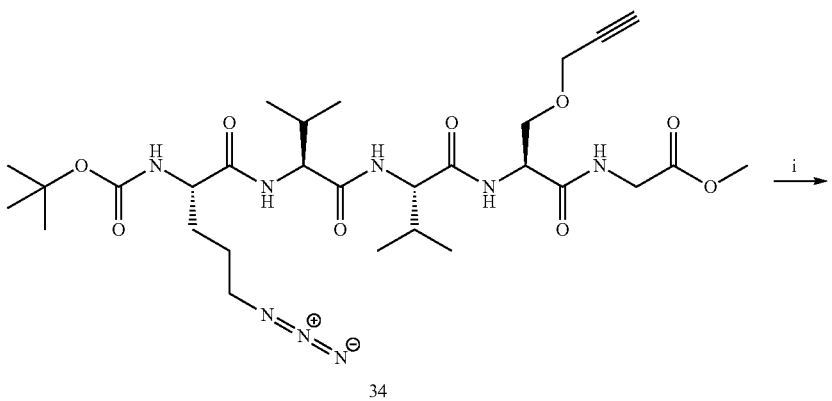
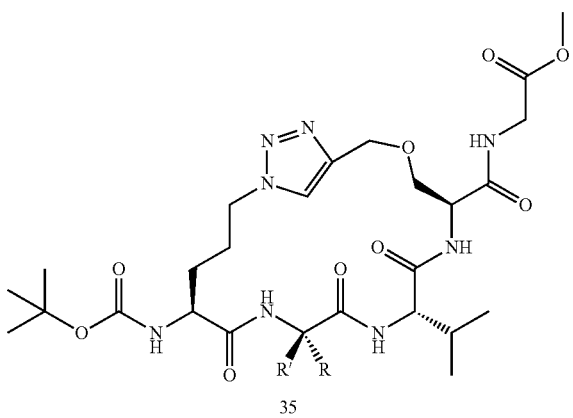
Scheme 7 Reagents and conditions:
(i) CuI•P(OEt)$_3$ (0.3 eq.), DIPEA, CH$_2$Cl$_2$, rt, 48 h

Synthesis

General

Chemicals were purchased from Sigma-Aldrich Co. and used as received unless otherwise stated. All solvents were of HPLC quality and all reagents were more than 98% pure. Flash chromatography was carried out using Silica Gel 60 (particle size: 0.04-0.063 mm/230-400 mesh) from Aldrich Co. NMR spectra were recorded in CDCl$_3$, DMSO-d$_6$, D$_2$O or CD$_2$Cl$_2$ on a Bruker Avance DPX200 or a Bruker Avance DPX300 instrument at 200 MHz and 300 MHz respectively. Except where otherwise indicated the NMR spectra were recorded at 25° C. All 2D spectra were recorded in phase sensitive mode using the TPPI (time proportional phase incrementation) method. The spectra were processed using the program MestReNova 6.0.2-5475 from Mestrelab Research S.L., Santiago de Compostela, Spain. The spectra were calibrated against residual CHCl$_3$ ($\delta_H$=7.26 ppm, $\delta_C$=77.16 ppm), CHD$_2$SOCD$_3$ ($\delta_H$=2.50 ppm, $\delta_C$=39.52 ppm), HDO ($\delta_H$=4.79 ppm) or CHDCl$_2$ ($\delta_H$=5.32 ppm, $\delta_C$=54.00 ppm). For the $^{13}$C spectra recorded in D$_2$O a small drop of MeOH was added and the spectra calibrated against the MeOH peak, which was defined to have a chemical shift of 49.50 ppm. For compounds with fewer than 5 residues only residue specific assignments were made. For the penta- and octapeptides signals were assigned using a combination of COSY, TOCSY and ROESY spectra. Amino acid abbreviations are given in parenthesis where the assignment of signals otherwise could be ambiguous. The residue O-propynyl-L-serine has been abbreviated propSer and the residue ε-azido-L-norvaline has been abbreviated azidonorVal. Identical residues, e.g. two Aibs, are numbered starting from the N-terminus. High-resolution mass spectrometric analyses were carried out on a Micromass Q-Tof-2 instrument with electrospray ionisation. Elemental (combustion) analyses were performed by Mikrokemi AB, Uppsala, Sweden. A small sample of each compound was dried under high vacuum at ambient temperature prior to analysis. Yields are uncorrected for residual solvent content in the isolated products.

Synthetic Procedures

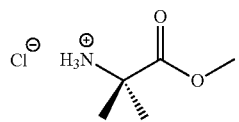

Aminoisobutyric Acid Methyl Ester Hydrochloride 2

Aminoisobutyric acid (29.80 g, 0.2890 mol) was suspended in MeOH (300 mL) and the suspension cooled to 0° C. (ice bath). Thionyl chloride (36.10 g, 0.3034 mol) was added dropwise over 15 min. The ice bath was removed and the reaction mixture stirred at 60° C. for 4 h. The oil bath was then removed and stirring continued at room temperature for another 22 h. The solvent and excess thionyl chloride were evaporated affording a white solid with a strong sulfur smell. Methanol (5×150 mL) was added and evaporated. The residue was dissolved in MeOH (120 mL), precipitated by addition of Et$_2$O (720 mL) and collected by filtration under suction affording the title compound as a white solid (35.12 g, 79%), with spectral characteristics in accordance with literature data'; $^1$H NMR (200 MHz, DMSO-d$_6$) δ 8.87 (br s, 3H, NH$_3^+$), 3.72 (s, 3H, OCH$_3$), 1.48 (s, 6H, CH$_3$); $^{13}$C NMR (75 MHz, DMSO-d$_6$) δ 172.0, 55.8, 53.1, 23.3; HRMS (m/z): M$^+$ calcd. for C$_{51}$H$_{12}$NO$_2$, 118.0868. found, 118.0871; Anal. Calcd. for C$_5$H$_{12}$ClNO$_2$: C, 39.10; H, 7.87; N, 9.12. Found: C, 38.9; H, 7.8; N, 9.0.

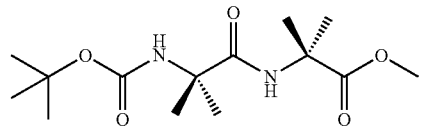

N-Tert-Butoxycarbonyl α,α-Dimethylglycyl α,α-Dimethylglycine Methyl Ester 3

Aminoisobutyric acid methyl ester hydrochloride 2 (11.44 g, 74.47 mmol) and N,N-diisopropylethylamine (9.63 g, 74.5 mmol) were dissolved in DMF (400 mL) and the solution added to solid N-tert-butoxycarbonyl α,α-dimethylglycine (15.14 g, 74.49 mmol). The solution/suspension was cooled to 0° C. (icebath) and HOBt hydrate (11.41 g, 74.51 mmol) and then EDC hydrochloride (15.71 g, 81.95 mmol) added together with more DMF (100 mL). The reaction mixture was stirred for 30 min at 0° C., after which the icebath was removed and stirring continued for 66 h at room temperature. The solvent was evaporated and the residue taken up in EtOAc (500 mL). The solution was washed with 2 M HCl (3×175 mL), 7.5% (w/w) K$_2$CO$_3$ solution (3×175 mL) and saturated brine (175 mL). The solution was dried with anhydrous MgSO$_4$ and the solvent evaporated affording a slightly yellowish solid (17.04 g). The solid (16.72 g) was washed with hexane (4×70 mL) affording an off-white solid (14.72 g, 67%), with spectral characteristics in accordance with literature data[2,3]; $^1$H NMR (200 MHz; DMSO-d$_6$) δ 7.57 (s, 1H, NH(Aib$_2$)), 6.63 (br s, 1H, NH(Aib$_1$)), 3.55 (s, 3H, OCH$_3$), 1.37 (s, 9H, (CH$_3$)$_3$), 1.34 (s, 6H, CH$_3$), 1.28 (s, 6H, CH$_3$); $^{13}$C NMR (75 MHz, DMSO-d$_6$) δ 174.5, 174.0, 154.1, 78.0, 55.5, 55.1, 51.7, 28.1, 24.8, 24.7; HRMS (m/z): [M+Na]$^+$ calcd. for C$_{14}$H$_{26}$N$_2$O$_5$Na, 325.1739. found, 325.1746; Anal. Calcd. for C$_{14}$H$_{26}$N$_2$O$_5$: C, 55.61; H, 8.67; N, 9.26. Found: C, 55.9; H, 8.7; N, 9.2.

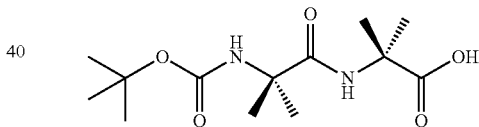

N-Tert-Butoxycarbonyl α,α-Dimethylglycyl α,α-Dimethylglycine 4

N-tert-butoxycarbonyl α,α-dimethylglycyl α,α-dimethylglycine methyl ester 3 (20.42 g, 67.53 mmol) was dissolved in THF (530 mL) and a solution of LiOH.H$_2$O (8.50 g, 0.203 mol) in de-ionized H$_2$O (270 mL) added in one portion. The reaction mixture was stirred for 4 h 30 min at room temperature. The solvents were evaporated and the residue redissolved in H$_2$O (800 mL). The solution was washed with Et$_2$O (2×500 mL) and acidified to pH 1-2 by addition of concentrated hydrochloric acid. This resulted in the precipitation of a white solid, which was collected by filtration, washed with H$_2$O (4×100 mL) and dried under vacuum overnight (16.18 g, 83%). The compound has been prepared before,[4] but as far as we have been able to establish has not been appropriately characterised; $^1$H NMR (200 MHz, DMSO-d$_6$) δ 12.33 (br s, 1H, COOH), 7.43 (s, 1H, NH(Aib$_2$)), 6.84 (br s, 1H, NH(Aib$_1$)), 1.36 (s, 15H, (CH$_3$)$_3$/CH$_3$), 1.27 (s, 6H, CH$_3$); $^{13}$C NMR (75 MHz, DMSO-d$_6$) δ 175.9, 173.7, 154.2, 78.2, 55.8, 55.1, 28.1, 25.0, 24.4; HRMS (m/z): [M+Na]$^+$ calcd. for C$_{13}$H$_{24}$N$_2$O$_5$Na, 311.1582. found, 311.1590; Anal. Calcd. for C$_{13}$H$_{24}$N$_2$O$_5$: C, 54.15; H, 8.39; N, 9.72. Found: C, 54.5; H, 8.4; N, 9.6.

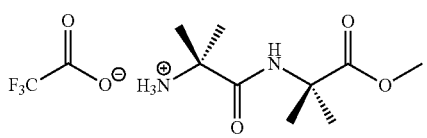

α,α-Dimethylglycyl α,α-Dimethylglycine Methyl Ester Trifluoroacetate 5

N-tert-butoxycarbonyl α,α-dimethylglycyl α,α-dimethylglycine methyl ester 3 (10.79 g, 35.69 mmol) was dissolved in 50% (v/v) TFA in $CH_2Cl_2$ (100 mL). The reaction mixture was stirred for 2 h 30 min at room temperature before the solvent and bulk of excess TFA were evaporated at 50° C. over 1 h 30 min. The residue was left standing overnight, dissolved in $CH_2Cl_2$ (100 mL) and the bulk of solvent evaporated. More $CH_2Cl_2$ (2×100 mL) was added and evaporated. The residue was washed with $Et_2O$ (3×60 mL) and the $Et_2O$ decanted off. The residue was dissolved in $CH_2Cl_2$ (30 mL). Upon standing a solid precipitated and was collected by filtration. The residue was washed with $Et_2O$ (3×60 mL) under suction and dried under vacuum affording the title compound as a white solid (10.17 g, 90%), with spectral characteristics in accordance with literature data[5,6]; $^1$H NMR (300 MHz, DMSO-$d_6$) δ 8.45 (s, 1H, NH), 8.20 (br s, 3H, $NH_3^+$), 3.57 (s, 3H, $OCH_3$), 1.47 (s, 6H, $CH_3$), 1.39 (s, 6H, $CH_3$); $^{13}$C NMR (75 MHz, DMSO-$d_6$) δ 174.1, 171.4, 158.3 (q, $J_{CF}$=33 Hz), 116.7 (q, $J_{CF}$=295 Hz), 56.4, 55.9, 52.1, 24.8, 23.3; HRMS (m/z): $M^+$ calcd. for $C_9H_{19}N_2O_3$, 203.1395. found, 203.1396; Anal. Calcd. for $C_{11}H_{19}F_3N_2O_5$: C, 41.77; H, 6.06; N, 8.86. Found: C, 41.8; H, 6.1; N, 8.7.

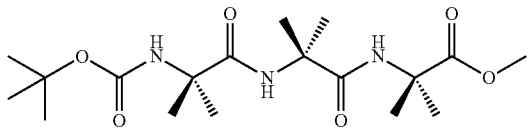

N-Tert-Butoxycarbonyl α,α-Dimethylglycyl α,α-Dimethylglycyl α,α-Dimethylglycine Methyl Ester 6

N-tert-butoxycarbonyl α,α-dimethylglycine 1 (3.20 g, 15.7 mmol) and α,α-dimethylglycyl α,α-dimethylglycine methyl ester trifluoroacetate 5 (4.98 g, 15.7 mmol) were dissolved in DMF (40 mL). N,N-Diisopropylethylamine (2.06 g, 15.9 mmol) and HOBt hydrate (2.41 g, 15.7 mmol) were added together with more DMF (10 mL). The solution was cooled to 0° C. (ice bath) and EDC hydrochloride (3.32 g, 17.3 mmol) added in portions together with additional DMF (10 mL). The reaction mixture was stirred for 15 min at 0° C., after which the ice bath was removed and stirring continued for 43 h at room temperature. The solvent was evaporated and the residue taken up in EtOAc (150 mL). The solution was washed with 1 M aqueous $H_2SO_4$ (3×50 mL), 7.5% (w/w) $K_2CO_3$ solution (3×50 mL) and saturated brine (50 mL). After dilution with EtOAc (100 mL) the solution was dried with anhydrous $MgSO_4$ and the solvent evaporated affording an off-white solid (3.20 g, 52%), with spectral characteristics in accordance with literature data[6]; $^1$H NMR (200 MHz, DMSO-$d_6$) δ 7.59 (s, 2H, NH($Aib_2$)/NH($Aib_3$)), 7.21 (s, 1H, NH($Aib_1$)), 3.53 (s, 3H, $OCH_3$), 1.41 (s, 9H, $(CH_3)_3$), 1.33 (s, 6H, $CH_3$), 1.28 (s, 6H, $CH_3$), 1.25 (s, 6H, $CH_3$); $^{13}$C NMR (75 MHz, DMSO-$d_6$) δ 174.4, 173.8, 173.2, 155.1, 78.7, 55.8, 55.4, 54.9, 51.6, 28.1, 24.8, 24.6, 24.6; HRMS (m/z): $[M+Na]^+$ calcd. for $C_{18}H_{33}N_3O_6Na$, 410.2267. found, 410.2269; Anal. Calcd. for $C_{18}H_{33}N_3O_6$: C, 55.80; H, 8.58; N, 10.84. Found: C, 55.9; H, 8.7; N, 11.0.

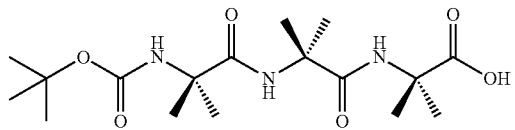

N-Tert-Butoxycarbonyl α,α-Dimethylglycyl α,α-Dimethylglycyl α,α-Dimethylglycine 7

N-tert-butoxycarbonyl α,α-dimethylglycyl α,α-dimethylglycyl α,α-dimethylglycine methyl ester 6 (2.14 g, 5.52 mmol) was dissolved in THF (60 mL) and a solution of $LiOH.H_2O$ (0.695 g, 16.6 mmol) in de-ionized $H_2O$ (30 mL) added. The reaction mixture was stirred for 3 h at room temperature before the bulk of solvent was evaporated and the solution diluted with $H_2O$ (100 mL). The solution was washed with $Et_2O$ (2×40 mL) and acidified to pH 2 by addition of 5 M HCl. A white solid precipitated and was collected by filtration. The residue was washed with icecold $H_2O$ (30 mL) and dried under high vacuum affording the title compound as a white solid (1.84 g, 89%). The compound has been prepared before,[6] but as far as we have been able to establish has not been appropriately characterised; $^1$H NMR (200 MHz, DMSO-$d_6$) δ 11.84 (br s, 1H, COOH), 7.59 (s, 1H, NH(Aib)), 7.48 (s, 1H, NH(Aib)), 7.18 (s, 1H, NH($Aib_1$)), 1.40 (s, 9H, $(CH_3)_3$), 1.32 (s, 6H, $CH_3$), 1.28 (s, 6H, $CH_3$), 1.25 (s, 6H, $CH_3$); $^{13}$C NMR (75 MHz, DMSO-$d_6$) δ 175.5, 173.5, 173.4, 155.1, 78.7, 55.8, 55.5, 54.8, 28.1, 24.8, 24.7, 24.6; HRMS (m/z): $[M+Na]^+$ calcd. for $C_{17}H_{31}N_3O_6Na$, 396.2110. found, 396.2115; Anal. Calcd. for $C_{17}H_{31}N_3O_6$: C, 54.68; H, 8.37; N, 11.25. Found: C, 55.0; H, 8.4; N, 11.1.

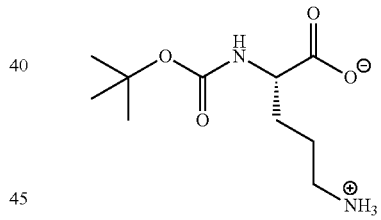

$N^\alpha$-Tert-Butoxycarbonyl L-Ornithine 9

$N^\alpha$-tert-butoxycarbonyl ε-benzoyl-L-ornithine 8 (10.73 g, 29.28 mmol) was dissolved in MeOH (200 mL). Palladium on activated carbon (10% (w/w) Pd (dry basis), wetted (50% (w/w) $H_2O$)) (6.24 g, 2.93 mmol Pd) was added in small portions and the bottle purged with hydrogen. A balloon with hydrogen was mounted on the bottle and the mixture stirred for 22 h at room temperature. Water (200 mL) was added and the reaction mixture filtered through Celite (16.5 g) to remove the catalyst. The Celite was washed with $H_2O$ (2×100 mL) and the solvents evaporated overnight at 55° C. affording the title compound as an off-white solid (6.66 g, 98%). The compound is commercially available; $^1$H NMR (200 MHz, $D_2O$) δ 3.99-3.79 (m, 1H, $C^\alpha$H), 3.10-2.93 (m, 2H, $CH_2NH_3^+$), 1.93-1.57 (m, 4H, $CH_2CH_2$), 1.43 (s, 9H, $(CH_3)_3$); $^{13}$C NMR (75 MHz, $D_2O$) δ 179.8, 158.2, 81.7, 56.0, 39.7, 29.5, 28.3, 24.0; HRMS (m/z): $[M+H]^+$ calcd. for $C_{10}H_{21}N_2O_4$, 233.1501. found, 233.1500; Anal. Calcd. for $C_{10}H_{20}N_2O_4$: C, 51.71; H, 8.68; N, 12.06. Found: C, 51.8; H, 8.7; N, 11.9.

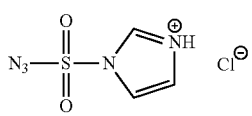 [SMILES: [N-]=[N+]=NS(=O)(=O)n1cc[nH+]c1 ; [Cl-]]

Imidazole-1-Sulfonyl Azide Hydrochloride 10

Sodium azide (13.12 g, 0.2018 mol) was suspended in CH$_3$CN (200 mL) and the suspension cooled to 0° C. (ice bath). Sulfuryl chloride (27.24 g, 0.2018 mol) was added dropwise over 20 min. The ice bath was removed and stirring continued for 20 h at room temperature (a septum and balloon were mounted on the reaction flask). The reaction mixture was cooled to 0° C. (ice bath) and imidazole (26.11 g, 0.3835 mol) added over 20 min. After stirring for 3 h 15 min at room temperature the suspension was diluted with EtOAc (400 mL) and washed with H$_2$O (2×400 mL) and saturated NaHCO$_3$ solution (2×400 mL). The solution was dried with anhydrous MgSO$_4$ and cooled to 0° C. (ice bath). Acetyl chloride (23.76 g, 0.3027 mol) was added dropwise to icecold EtOH (75 mL) over 10-15 min. After stirring for 10 min at 0° C. the solution was added to the EtOAc solution over 20 min. After stirring for 10 min the resulting suspension was filtered and the precipitate washed with EtOAc (4×100 mL) and dried under suction for 30 min affording the title compound as a white solid (31.81 g, 75%) with spectral characteristics in accordance with literature data[7]; $^1$H NMR (200 MHz, D$_2$O) δ 9.43 (t, J=1.4 Hz, 1H), 8.05 (dd, J=2.1, 1.8 Hz, 1H), 7.64 (dd, J=2.1, 1.2 Hz, 1H); $^{13}$C NMR (75 MHz, D$_2$O) δ 138.0, 123.1, 120.6; HRMS (m/z): M$^+$ calcd. for C$_3$H$_4$N$_5$O$_2$S, 174.0085. found, 174.0085; Anal. Calcd. for C$_3$H$_4$ClN$_5$O$_2$S: C, 17.19; H, 1.92; N, 33.41. Found: C, 17.4; H, 2.1; N, 33.5.

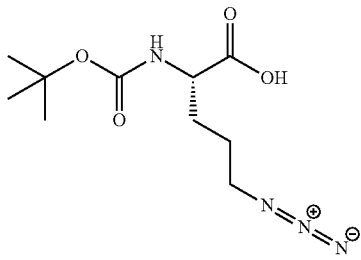 [SMILES: CC(C)(C)OC(=O)N[C@@H](CCCN=[N+]=[N-])C(=O)O]

N$^α$-Tert-Butoxycarbonyl ε-Azido-L-Norvaline 11

N$^α$-tert-butoxycarbonyl L-ornithine 9 (6.55 g, 28.2 mmol), potassium carbonate (9.75 g, 70.5 mmol) and copper sulfate pentahydrate (0.070 g, 0.28 mmol) were dissolved/suspended in MeOH (140 mL). Imidazole-1-sulfonyl azide hydrochloride 10 (7.09 g, 33.8 mmol) was added in small portions at room temperature together with additional MeOH (10 mL). The reaction mixture was stirred for 17 hours at room temperature before the solvent was evaporated and the residue dissolved in H$_2$O (400 mL). The solution was acidified to pH 2 by addition of concentrated hydrochloric acid. The resulting mixture was extracted with EtOAc (3×250 mL) and the combined organic extracts washed with saturated brine (200 mL). The solution was dried with anhydrous MgSO$_4$ and the solvent evaporated affording a yellow oil (7.19 g). The oil (7.00 g) was purified by flash column chromatography (eluent: hexane/EtOAc/AcOH (30:20:1)). The fractions containing reasonably pure material by TLC were combined (total volume: 750 mL) and washed with 0.5 M HCl (3×250 mL). The solution was dried with anhydrous MgSO$_4$ and the solvent evaporated affording a pale yellow oil (4.36 g, corresponds to 4.48 g from the given amounts of starting materials, 61%), with spectral characteristics in accordance with literature data[8,9]; $^1$H NMR (300 MHz, DMSO-d$_6$) δ; 12.44 (br s, 1H, COOH), 7.09 (d, J=8.1 Hz, 1H, NH), 3.96-3.83 (m, 1H, C$^α$H), 3.31 (t, J=6.6 Hz, 2H, CH$_2$N$_3$), 1.83-1.50 (m, 4H, CH$_2$CH$_2$CH$_2$N$_3$), 1.38 (s, 9H, (CH$_3$)$_3$); $^{13}$C NMR (75 MHz, DMSO-d$_6$) δ 173.9, 155.6, 78.0, 53.0, 50.3, 28.2, 28.0, 25.1; FIRMS (m/z): [M+Na]$^+$ calcd. for C$_{10}$H$_{18}$N$_4$O$_4$Na, 281.1225. found, 281.1219; Anal. Calcd for C$_{10}$H$_{18}$N$_4$O$_4$: C, 46.50; H, 7.02; N, 21.69. Found: C, 46.5; H, 7.1; N, 21.5.

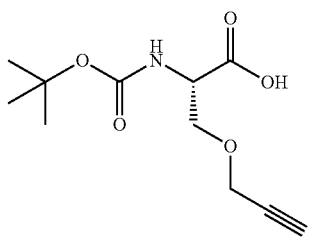 [SMILES: C#CCOC[C@H](NC(=O)OC(C)(C)C)C(=O)O]

N-Tert-Butoxycarbonyl O-Propynyl-L-Serine 13

N-tert-butoxycarbonyl L-serine 12 (25.42 g, 0.1239 mol) was dissolved in DMF (190 mL) and the solution cooled to 0° C. (ice bath). Sodium hydride (60% (w/w) dispersion in mineral oil, 10.90 g, 0.2725 mol) was added over 15 min and the reaction mixture stirred for 1 h at 0° C. 3-Bromopropyne (80% (w/w) solution in toluene, 20.25 g, 0.1362 mol) was added dropwise over 15 min. The reaction mixture was stirred for 1 h at 0° C., after which the ice bath was removed and stirring continued for 3 h 40 min at room temperature. The solvent was evaporated and the residue dissolved in H$_2$O (800 mL). The solution was washed with Et$_2$O (3×350 mL) and acidified to pH 2 by addition of 3 M HCl. The resulting mixture was extracted with EtOAc (5×350 mL). The combined organic extracts were dried with anhydrous MgSO$_4$ and the solvent evaporated affording a yellow/orange viscous oil (30.51 g). A portion of the oil (8.70 g) was purified by flash column chromatography (eluent: EtOAc/hexane/AcOH (23:27:1)). The fractions containing reasonably pure compound by TLC (total volume: 950 mL) were washed with 0.5 M HCl (3×500 mL). The solution was dried with anhydrous MgSO$_4$ and the solvent evaporated affording a pale yellow, viscous oil (6.58 g, corresponds to 23.03 g from the given amounts of starting materials, 77%), with spectral characteristics in accordance with literature data[10]; $^1$H NMR (200 MHz, DMSO-d$_6$) δ 12.62 (br s, 1H, COOH), 6.88 (d, J=8.2 Hz, 1H, NH (rotomer 1)), 6.53 (d, J=6.4 Hz, 1H, NH (rotomer 2)), 4.21-4.06 (m, 1H, C$^α$H), 4.13 (d, J=2.4 Hz, 2H, CH$_2$CCH), 3.66 (d, J=5.4 Hz, 2H, CH$_2$), 3.40 (t, J=2.4 Hz, 1H, CCH), 1.38 (s, 9H, (CH$_3$)$_3$); $^{13}$C NMR (75 MHz, DMSO-d$_6$) δ 171.8, 155.4, 79.9, 78.3, 77.4, 68.8, 57.7, 53.6, 28.2; HRMS (m/z): [M+Na]$^+$ calcd. for C$_{11}$H$_{17}$NO$_5$Na, 266.1004. found, 266.1010; Anal. Calcd. for C$_{11}$H$_{17}$NO$_5$: C, 54.31; H, 7.04; N, 5.76. Found: C, 54.7; H, 7.1; N, 5.5.

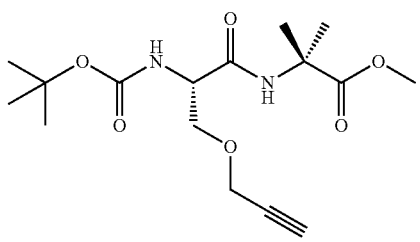

N-Tert-Butoxycarbonyl O-Propynyl-L-Seryl α,α-Dimethylglycine Methyl Ester 14

N-tert-butoxycarbonyl O-propynyl-L-serine 13 (6.26 g, 25.7 mmol) was dissolved in DMF (50 mL). Aminoisobutyric acid methyl ester hydrochloride 2 (3.95 g, 25.7 mmol) was dissolved in DMF (50 mL) and N,N-diisopropylethylamine (3.32 g, 25.7 mmol) added. The resulting solution was added to the solution of 13 in one portion and the mixture cooled to 0° C. (ice bath). HOBt hydrate (3.94 g, 25.7 mmol) and then EDC hydrochloride (5.43 g, 28.3 mmol) were added in portions together with additional DMF (50 mL). The reaction mixture was stirred for 1 h at 0° C., after which the ice bath was removed and stirring continued for 42 h at room temperature. The solvent was evaporated and the residue taken up in EtOAc (300 mL). The solution was washed with 2 M HCl (3×100 mL), 7.5% (w/w) $K_2CO_3$ solution (3×100 mL) and brine (100 mL). The solution was dried with anhydrous $MgSO_4$ and the solvent evaporated affording a yellow/orange, viscous oil which was deemed to be of satisfactory purity to be used in subsequent steps without further purification (7.94 g, 90%); $^1$H NMR (300 MHz, DMSO-$d_6$) δ 8.23 (s, 1H, NH(Aib)), 6.69 (d, J=8.5 Hz, 1H, NH(propSer), rotamer 1), 6.32 (d, 1H, NH(propSer), rotamer 2), 4.21-4.08 (m, 1H, $C^αH$), 4.13 (d, J=2.1 Hz, 2H, $CH_2CCH$), 3.57 (dd, J=9.9, 4.8 Hz, 1H, CHH), 3.54 (s, 3H, $OCH_3$), 3.47 (dd, J=9.6, 7.4 Hz, 1H, CHH) 3.42 (t, J=2.3 Hz, 1H, CCH), 1.38 (s, 9H, $(CH_3)_3$), 1.35 (s, 3H, $CH_3$), 1.33 (s, 3H, $CH_3$); $^{13}$C NMR (75 MHz, $d_6$-DMSO) δ 174.0, 169.0, 154.9, 79.9, 78.1, 77.1, 69.3, 57.5, 54.9, 53.7, 51.7, 28.0, 24.6; HRMS (m/z): $[M+Na]^+$ calcd. for $C_{16}H_{26}N_2O_6Na$, 365.1688. found, 365.1695; Anal. Calcd. for $C_{16}H_{26}N_2O_6$: C, 56.13; H, 7.65; N, 8.18. Found: C, 56.1; H, 7.7; N, 8.0.

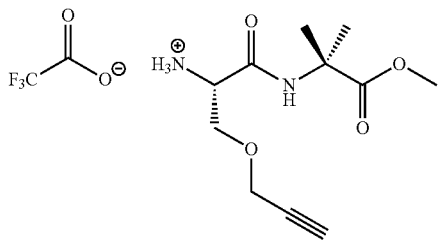

O-Propynyl L-Seryl α,α-Dimethylglycine Methyl Ester Trifluoroacetate 15

Purified N-tert-butoxycarbonyl O-propynyl-L-seryl α,α-dimethylglycine methyl ester 14 (2.27 g, 6.63 mmol) was dissolved in 50% (v/v) TFA in $CH_2Cl_2$ and the reaction mixture stirred for 1 h 10 min at room temperature. The solvent and bulk of excess TFA were evaporated and $CH_2Cl_2$ (3×20 mL) added and evaporated. Diethyl ether (25 mL) was added causing a white solid to precipitate on standing. The $Et_2O$ was decanted off and the residue washed with more $Et_2O$ (2×25 mL). After decantation of the $Et_2O$ the residue was dried under high vacuum affording the title compound as a white solid (2.10 g, 89%); $^1$H NMR (200 MHz, DMSO-$d_6$) δ 8.95 (s, 1H, NH), 8.31 (br s, 3H, $NH_3^+$), 4.20 (d, J=2.4 Hz, 2H, $CH_2CCH$), 4.02 (dd, J=5.8, 3.8 Hz, 1H, $C^αH$ or CHH), 3.88-3.67 (m, 2H, $CH_2$ or $C^αH$/CHH), 3.57 (s, 3H, $OCH_3$), 3.52 (t, J=2.3 Hz, 1H, CCH), 1.39 (s, 3H, $CH_3$), 1.36 (s, 3H, $CH_3$); $^{13}$C NMR (75 MHz, DMSO-$d_6$) δ 173.9, 165.7, 158.3 (q, $J_{CF}$=31 Hz), 117.2 (q, $J_{CF}$=298 Hz), 79.5, 78.0, 68.0, 58.1, 55.5, 52.1, 52.0, 24.7; HRMS (m/z): $M^+$ calcd. for $C_{11}H_{19}N_2O_4$, 243.1344. found, 243.1335; Anal. Calcd. for $C_{13}H_{19}F_3N_2O_6$: C, 43.82; H, 5.38; N, 7.86. Found: C, 43.8; H, 5.4; N, 7.8.

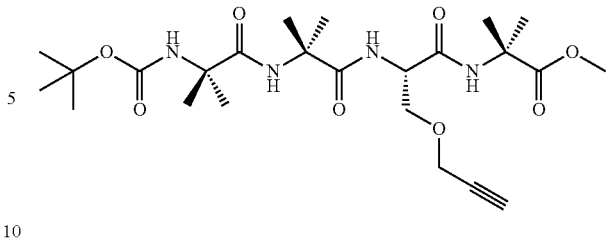

N-Tert-Butoxycarbonyl α,α-Dimethylglycyl α,α-Dimethylglycyl O-Propynyl-L-Seryl α,α-Dimethylglycine Methyl Ester 16

N-tert-butoxycarbonyl α,α-dimethylglycyl α,α-dimethylglycine 4 (3.37 g, 11.7 mmol) and O-propynyl L-seryl α,α-dimethylglycine methyl ester trifluoroacetate 15 (4.16 g, 11.7 mmol) were dissolved in DMF (30 mL). A solution of N,N-diisopropylethylamine (1.51 g, 11.7 mmol) in DMF (20 mL) was added and the solution cooled to 0° C. (ice bath). HOBt hydrate (1.79 g, 11.7 mmol) and then EDC hydrochloride (2.46 g, 12.8 mmol) were added in portions together with more DMF (10 mL). The reaction mixture was stirred for 5 min at 0° C. after which the ice bath was removed and stirring continued for 44 h at room temperature. The solvent was evaporated and the residue taken up in EtOAc (300 mL). The solution was washed with 1 M HCl (3×120 mL), 7.5% (w/w) $K_2CO_3$ solution (3×120 mL) and saturated brine (120 mL). The solution was dried with anhydrous $MgSO_4$ and the solvent evaporated affording a slightly yellowish solid (5.18 g). The solid was purified by flash column chromatography (eluent: $CH_2Cl_2$/acetone (4:1)) affording the title compound as a white solid (4.58 g, 77%); $^1$H NMR (300 MHz, DMSO-$d_6$) δ 8.11 (s, 1H, NH(Aib)), 7.73 (s, 1H, NH(Aib)), 7.66 (d, J=8.1 Hz, 1H, NH(propSer)), 7.31 (s, 1H, NH($Aib_1$)), 4.33 (td, J=8.6, 3.8 Hz, 1H, $C^αH$), 4.03 (t, J=2.8 Hz, 1H, $CH_2CCH$), 3.81 (dd, J=9.9, 3.6 Hz, 1H, CHH), 3.59 (dd, J=9.3, 9.3 Hz, 1H, CHH), 3.54 (s, 3H, $OCH_3$), 3.41 (t, J=2.3 Hz, 1H, CCH), 1.41 (s, 9H, $(CH_3)_3$), 1.37 (s, 3H, $CH_3$), 1.34 (s, 3H, $CH_3$), 1.33 (s, 3H, $CH_3$), 1.29 (s, 3H, $CH_3$), 1.28 (s, 6H, $CH_3$); $^{13}$C NMR (75 MHz, DMSO-$d_6$) δ 175.2, 174.2, 174.0, 168.7, 155.5, 79.8, 79.0, 77.2, 68.5, 57.3, 55.9, 55.8, 55.0, 52.9, 51.7, 28.1, 26.7, 25.4, 24.6, 24.6, 24.1, 23.2; HRMS (m/z): $[M+Na]^+$ calcd. for $C_{24}H_{40}N_4O_8Na$, 535.2743. found, 535.2728; Anal. Calcd. for $C_{24}H_{40}N_4O_8$: C, 56.23; H, 7.87; N, 10.93. Found: C, 56.0; H, 7.8; N, 10.8.

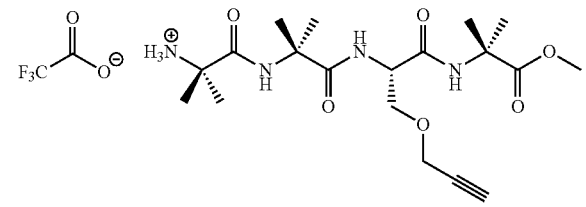

α,α-Dimethylglycyl α,α-Dimethylglycyl O-Propynyl-L-Seryl α,α-Dimethylglycine Methyl Ester Trifluoroacetate 17

N-tert-butoxycarbonyl α,α-dimethylglycyl α,α-dimethylglycyl O-propynyl-L-seryl α,α-dimethylglycine methyl ester 16 (4.79 g, 9.35 mmol) was dissolved in 50% (v/v) TFA in $CH_2Cl_2$ (70 mL) and the reaction mixture stirred for 1 h 30 min at room temperature. The solvent and bulk of excess TFA were evaporated and $CH_2Cl_2$ (2×70 mL) added and evaporated. The residue was washed with $Et_2O$ (3×35 mL), redissolved in $CH_2Cl_2$ (100 mL), the solvent evaporated and the residue washed with Et$_2$O (70 mL). Finally, CH$_2$Cl$_2$ (3×120 mL) was added and evaporated and the residue dried under high vacuum affording a white solid (4.93 g, 100%); $^1$H NMR (200 MHz, DMSO-d$_6$) δ 8.38-8.00 (m, 5H, NH$_3^+$/NH(Aib$_2$)/NH(Aib$_4$)), 7.25 (d, J=7.8 Hz, 1H, NH(propSer)), 4.33 (q, J=5.4 Hz, 1H, C$^\alpha$H), 4.11 (d, J=2.4 Hz, 2H, CH$_2$CCH), 3.62 (d, J=5.4 Hz, 2H, CH$_2$), 3.54 (s, 3H, OCH$_3$), 3.43 (t, J=2.3 Hz, 1H, CCH), 1.49 (s, 6H, CH$_3$), 1.40 (s, 6H, CH$_3$), 1.35 (s, 6H, CH$_3$); $^{13}$C NMR (75 MHz, DMSO-d$_6$) δ 174.2, 173.2, 171.3, 168.6, 158.4 (q, J$_{CF}$=32 Hz), 117.1 (q, J=297 Hz), 80.1, 77.3, 69.0, 57.7, 56.7, 56.6, 55.1, 52.4, 51.9, 25.0, 24.8, 24.7, 24.6, 23.3, 23.3; HRMS (m/z): M$^+$ calcd. for C$_{19}$H$_{33}$N$_4$O$_6$, 413.2400. found, 413.2391; Anal. Calcd. for C$_{21}$H$_{33}$F$_3$N$_4$O$_8$: C, 47.91; H, 6.32; N, 10.64. Found: C, 47.2; H, 6.2; N, 10.5.

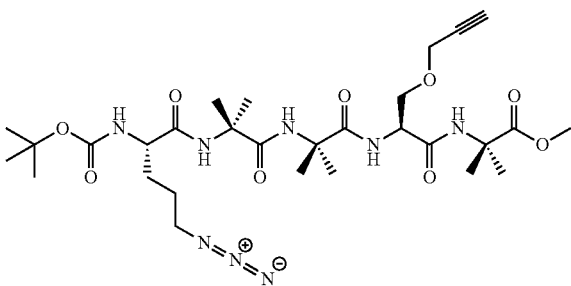

N$^\alpha$-Tert-Butoxycarbonyl ε-Azido-L-Norvalyl α,α-Dimethylglycyl α,α-Dimethylglycyl O-Propynyl-L-Seryl α,α-Dimethylglycine Methyl Ester 18

A solution of N$^\alpha$-tert-butoxycarbonyl ε-azido-L-norvaline 11 (0.565 g, 98.7% pure by $^1$H-NMR, 2.16 mmol) in CH$_2$Cl$_2$ (8 mL) and a solution of N,N-diisopropylethylamine (0.278 g, 2.15 mmol) in CH$_2$Cl$_2$ (6 mL) was added to solid α,α-dimethylglycyl α,α-dimethylglycyl O-propynyl-L-seryl α,α-dimethylglycine methyl ester trifluoroacetate 17 (1.136 g, 2.158 mmol) and the resulting solution cooled to 0° C. (ice bath). HOBt hydrate (0.331 g, 2.16 mmol) and then EDC hydrochloride (0.455 g, 2.37 mmol) were added together with more CH$_2$Cl$_2$ (6 mL). The reaction mixture was stirred for 2 h at 0° C. after which the ice bath was removed and stirring continued for another 41 h at room temperature. The reaction mixture was diluted with CH$_2$Cl$_2$ (80 mL) and the solution washed with 1 M HCl (3×40 mL), 7.5% (w/w) K$_2$CO$_3$ solution (3×40 mL) and saturated brine (40 mL). The solution was dried with anhydrous MgSO$_4$ and the solvent evaporated at room temperature affording the title compound as an off-white solid, which was deemed to be pure enough to be used in subsequent reactions without further purification (1.008 g, 72%); $^1$H NMR (300 MHz, DMSO-d$_6$) δ 8.43 (s, 1H, NH(Aib$_2$)), 7.70 (s, 1H, NH(Aib$_3$)), 7.68 (s, 1H, NH(Aib$_5$)), 7.51 (d, J=8.0 Hz, 1H, NH(propSer)), 7.01 (d, J=6.3 Hz, 1H, NH(azidonorVal)), 4.22 (td, J=8.1, 3.6 Hz, 1H, C$^\alpha$H (propSer)), 4.14 (dd, J=7.2, 2.4 Hz, 2H, CH$_2$CCH), 3.95-3.84 (m, 1H, C$^\alpha$H(azidonorVal)), 3.79 (dd, J=9.9, 3.8 Hz, 1H, C$^\alpha$H-CHHO), 3.66 (dd, J=9.2, 9.2 Hz, 1H, C$^\alpha$HCHHO), 3.54 (s, 3H, OCH$_3$), 3.41 (t, J=2.3 Hz, 1H, CCH), 3.37-3.21 (m, 2H, CH$_2$N$_3$), 1.81-1.49 (m, 4H, CH$_2$CH$_2$), 1.39 (s, 9H, (CH$_3$)$_3$), 1.37 (s, 3H, CH$_3$), 1.36-1.31 (m, 12H, CH$_3$), 1.29 (s, 3H, CH$_3$); $^{13}$C NMR (50 MHz, DMSO-d$_6$) δ 174.8, 174.0, 174.0, 172.7, 168.7, 155.7, 80.1, 78.5, 77.1, 68.8, 57.6, 56.0, 56.0, 55.0, 54.2, 53.3, 51.7, 50.5, 28.1, 28.1, 26.6, 25.2, 24.8, 24.6, 24.6, 23.9, 23.1; HRMS (m/z): [M+Na]$^+$ calcd. for C$_{29}$H$_{48}$N$_8$O$_9$Na, 675.3441. found, 675.3448; Anal. Calcd. for C$_{29}$H$_{48}$N$_8$O$_9$: C, 53.36; H, 7.41; N, 17.17. Found: C, 53.1; H, 7.4; N, 17.0.

Alternative Synthesis of 18 (Scheme 4):

Crude N$^\alpha$-tert-butoxycarbonyl ε-azido-L-norvalyl α,α-dimethylglycyl α,α-dimethylglycine 25 was purified by flash column chromatography (eluent: EtOAc/hexane/AcOH (35:15:1). The fractions containing pure compound (total volume: 1.5 L) were washed with 0.5 M HCl (3×500 mL), dried with anhydrous MgSO$_4$ and the solvent evaporated affording a 1:1 complex 26 between N$^\alpha$-tert-butoxycarbonyl ε-azido-L-norvalyl α,α-dimethylglycyl α,α-dimethylglycine and acetic acid. O-propynyl-L-seryl α,α-dimethylglycine methyl ester trifluoroacetate 15 (0.791 g, 2.22 mmol) was suspended in CH$_2$Cl$_2$ (5 mL) and N,N-diisopropylethylamine (0.286 g, 2.21 mmol) dissolved in CH$_2$Cl$_2$ (5 mL) added. The resulting solution was added to a solution of 26 (0.951 g, 2.22 mmol) in CH$_2$Cl$_2$ (20 mL) together with more CH$_2$Cl$_2$ (5 mL). The solution was cooled to 0° C. (ice bath) and HOAt (0.302 g, 2.22 mmol) and then EDC hydrochloride (0.468 g, 2.44 mmol) added. The reaction mixture was stirred at 0° C. for 1 h, after which the ice bath was removed and stirring continued for 24 h at room temperature. The reaction mixture was diluted with CH$_2$Cl$_2$ (60 mL) and washed with 1 M aqueous H$_2$SO$_4$ (3×30 mL), 7.5% (w/w) K$_2$CO$_3$ solution (3×30 mL) and saturated brine (30 mL). The solution was dried with anhydrous MgSO$_4$ and the solvent evaporated affording a white solid (1.307 g). The crude product (1.294 g) was purified twice by flash column chromatography (eluent: CH$_2$Cl$_2$/acetone (4:1) and then CH$_2$Cl$_2$/acetone (3:1)). The eluent was evaporated at room temperature affording the title compound as a white solid (0.282 g, 19%).

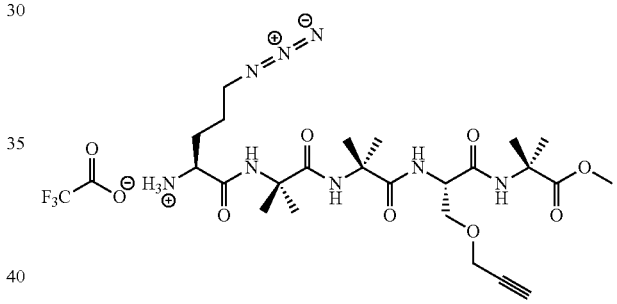

ε-Azido-L-Norvalyl α,α-Dimethylglycyl α,α-Dimethylglycyl O-Propynyl-L-Seryl α,α-Dimethylglycine Methyl Ester Trifluoroacetate 19

N$^\alpha$-tert-butoxycarbonyl ε-azido-L-norvalyl α,α-dimethylglycyl α,α-dimethylglycyl O-propynyl-L-seryl α,α-dimethylglycine methyl ester 18 (0.690 g, 1.06 mmol) was dissolved in 50% TFA in CH$_2$Cl$_2$ (18 mL). The reaction mixture was stirred for 1 h at room temperature before the solvent and bulk of excess TFA were evaporated affording a clear, very viscous oil. The residue was washed with Et$_2$O (3×18 mL). The bulk of Et$_2$O was decanted off between each washing and the last traces evaporated. The residue was dried under high vacuum affording a slightly off-white solid (0.663 g, 94%); $^1$H NMR (300 MHz, DMSO-d$_6$) δ 8.99 (s, 1H, NH(Aib$_2$)), 8.25 (br s, 3H, NH$_3^+$), 7.91 (s, 1H, NH(Aib$_3$)), 7.82 (s, 1H, NH(Aib$_5$)), 7.23 (d, J=8.1 Hz, 1H, NH(propSer)), 4.29 (td, J=7.7, 4.4 Hz, 1H, C$^\alpha$H(propSer)), 4.12 (d, J=2.0 Hz, 2H, CH$_2$CCH), 3.89-3.79 (m, 1H, C$^\alpha$H(azidonorVal)), 3.79-3.64 (m, 2H, C$^\alpha$HCH$_2$O), 3.55 (s, 3H, OCH$_3$), 3.42 (t, J=2.2 Hz, 1H, CCH), 3.36 (t, J=6.8 Hz, 2H, CH$_2$N$_3$), 1.94-1.70 (m, 2H, CH$_2$CH$_2$CH$_2$N$_3$), 1.66-1.40 (m, 2H, CH$_2$CH$_2$CH$_2$N$_3$), 1.45-1.25 (m, 18H, CH$_3$); $^{13}$C NMR (50 MHz, DMSO-d$_6$) δ 174.1, 174.0, 173.9, 168.8, 168.4, 158.2, 80.1, 77.3, 68.7, 57.4, 56.4, 56.2, 55.0, 52.6, 51.8, 50.2, 27.9, 25.9, 24.8, 24.7, 24.2, 23.8, 23.5; HRMS (m/z): M$^+$ calcd. for C$_{24}$H$_{41}$N$_8$O$_7$, 553.3098.

found, 553.3106; Anal. Calcd. for $C_{26}H_{41}F_3N_8O_9$: C, 46.84; H, 6.20; N, 16.81. Found: C, 46.5; H, 6.3; N, 16.4.

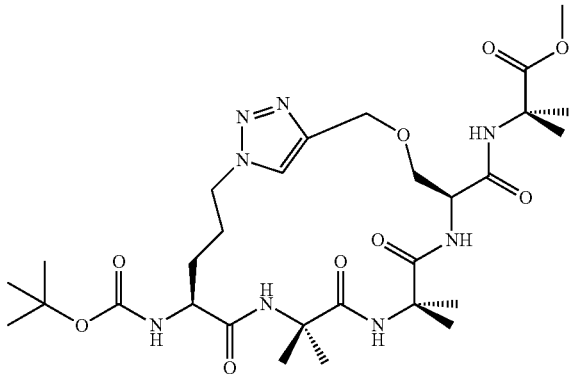

Methyl 2-((5S,14S)-5-(tert-butoxycarbonylamino)-8, 8,11,11-tetramethyl-6,9,12-trioxo-16-oxa-1,7,10,13, 19,20-hexaazabicyclo[16.2.1]henicosa-18 (21),19-dienecarboxamido)-2-methylpropanoate 20

Freshly prepared $N^\alpha$-tert-butoxycarbonyl-ε-azido-L-norvalyl α,α-dimethylglycyl α,α-dimethylglycyl O-propynyl-L-seryl α,α-dimethylglycine methyl ester 18 (0.489 g, 0.750 mmol, 1.00 eq.) was dissolved in $CH_2Cl_2$ (100 mL) and the solution divided equally between two 3 L round bottomed flasks each containing $CH_2Cl_2$ (2.3 L). N,N-Diisopropylethylamine (0.291 g, 2.25 mmol, 3.00 eq.) was dissolved in $CH_2Cl_2$ (20 mL) and 10 mL of the solution added to each of the round bottomed flasks. Copper(I) iodide triethylphosphite (0.258 g, 1.12 mmol, 1.50 eq.) was dissolved in $CH_2Cl_2$ (100 mL) and 10 mL of the solution added to each round bottomed flask. The reaction mixtures were stirred protected from light for 42 hours at room temperature. The solvent was evaporated at 30° C. over 2-3 hours. The residue was redissolved in $CH_2Cl_2$ and purified by flash column chromatography (eluent: $CH_2Cl_2$/MeOH/acetone (14:1:1)) affording the title compound as a white solid (0.404 g, 83%); $^1$H NMR (300 MHz, $CDCl_3$) δ 7.80 (s, 1H, $C_2HN_3$), 7.42 (s, 1H, NH(Aib$_5$)), 7.28 (d, J=9.0 Hz, 1H, NH(propSer)), 6.95 (s, 1H, NH(Aib$_3$)), 6.78 (s, 1H, NH(Aib$_2$)), 5.47 (d, J=4.9 Hz, 1H, NH(azidonorVal)), 4.80 (d, J=12.7 Hz, 1H, OCHHC$_2$HN$_3$), 4.70 (ddd, J=8.5, 7.1, 3.6 Hz, 1H, CH(propSer)), 4.59-4.49 (m, 1H, CHHN$_3$C$_2$H), 4.58 (d, J=12.9 Hz, 1H, OCHHC$_2$HN$_3$), 4.46-4.34 (m, 1H, CHHN$_3$C$_2$H), 3.92 (dd, J=8.9, 7.2 Hz, 1H, C$^\alpha$HCHHO), 3.68 (s, 3H, OCH$_3$), 3.67 (dd, J=8.4, 3.6 Hz, 1H, C$^\alpha$HCHHO), 3.22 (dd, J=12.4, 7.2 Hz, 1H, C$^\alpha$H(azidonorVal)), 2.14-1.87 (m, 2H, CH$_2$CH$_2$CH$_2$), 1.76-1.58 (m, 2H, C$^\alpha$HCH$_2$CH$_2$CH$_2$), 1.53 (s, 3H, CH$_3$), 1.52 (s, 3H, CH$_3$), 1.48 (s, 3H, CH$_3$), 1.43 (s, 9H, (CH$_3$)$_3$), 1.43-1.38 (m, 9H, CH$_3$); $^{13}$C NMR (75 MHz, CDCl$_3$) δ 175.3, 174.5, 173.9, 171.8, 169.5, 156.5, 145.4, 124.2, 81.4, 69.0, 65.0, 57.2, 56.6, 56.2, 54.4, 54.1, 52.4, 50.0, 31.1, 28.4, 27.9, 26.8, 25.5, 25.1, 24.7, 24.1, 23.5; HRMS (m/z): [M+Na]$^+$ calcd. for $C_{29}H_{48}N_8O_9$Na, 675.3441. found, 675.3438; Anal. Calcd. for $C_{29}H_{48}N_8O_9$: C, 53.36; H, 7.41; N, 17.17. Found: C, 52.9; H, 7.4; N, 16.8.

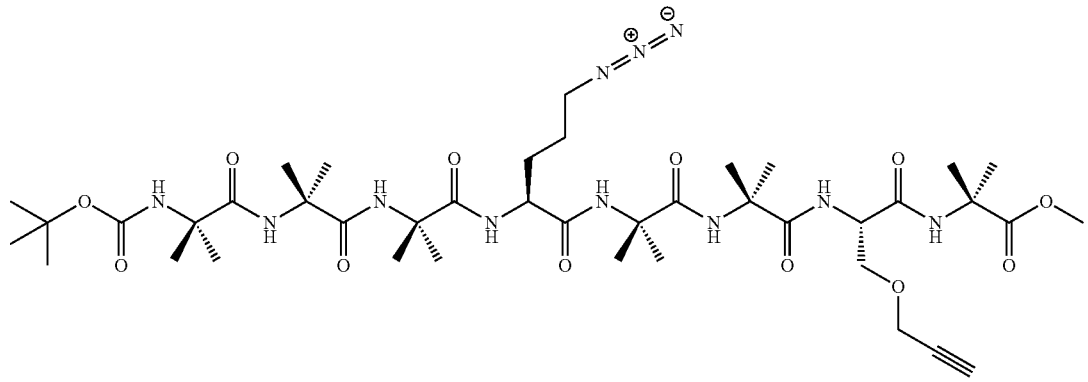

N-tert-butoxycarbonyl α,α-dimethylglycyl α,α-dimethylglycyl α,α-dimethylglycyl ε-azido-L-norvalyl α,α-dimethylglycyl α,α-dimethylglycyl O-propynyl-L-seryl α,α-dimethylglycyl methyl ester 21

ε-azido-L-norvalyl α,α-dimethylglycyl α,α-dimethylglycyl O-propynyl-L-seryl α,α-dimethylglycyl methyl ester trifluoroacetate 19 (0.551 g, 0.827 mmol) and N-tert-butoxycarbonyl α,α-dimethylglycyl α,α-dimethylglycyl α,α-dimethylglycine 7 (0.309 g, 0.827 mmol) were suspended in $CH_2Cl_2$ (5 mL) and a solution of N,N-diisopropylethylamine (0.107 g, 0.828 mmol) in $CH_2Cl_2$ (7 mL) added. HOBt hydrate (0.127 g, 0.829 mmol) and then EDC hydrochloride (0.174 g, 0.908 mmol) were added together with more $CH_2Cl_2$ (5 mL) at room temperature. The reaction mixture was stirred for 45 h at room temperature before being diluted with $CH_2Cl_2$ (65 mL). The solution was washed with 5% (w/w) citric acid monohydrate solution (3×35 mL), 7.5% (w/w) $K_2CO_3$ solution (3×35 mL) and saturated brine (35 mL). The solution was dried with anhydrous MgSO$_4$ and the solvent evaporated affording a white solid (0.595 g). The solid (0.573 g) was purified by flash column chromatography (eluent: $CH_2Cl_2$/acetone (3:1)) affording the title compound as a white solid (0.323 g, 43%); $^1$H NMR (300 MHz, CD$_2$Cl$_2$) δ 7.95 (s, 1H, NH(Aib$_3$)), 7.87 (s, 1H, NH(Aib$_5$)), 7.86 (d, J=4.2 Hz, 1H, NH(azidonorVal)), 7.60 (d, J=7.2 Hz, 1H, NH(propSer)), 7.59 (s, 1H, NH(Aib$_8$)), 7.30 (s, 1H, NH(Aib$_6$)), 6.88 (s, 1H, NH(Aib$_2$)), 5.63 (s, 1H, NH(Aib$_1$)), 4.44 (td, J=8.3, 3.6 Hz, 1H, C$^\alpha$H(propSer)), 4.21 (dd, J=4.1, 2.4 Hz, 1H, CH$_2$CCH), 4.01-3.79 (m, 3H, C$^\alpha$H(azidonorVal)/CH$_2$O), 3.65 (s, 3H, OCH$_3$), 3.33 (t, J=6.6 Hz, 2H, CH$_2$N$_3$), 2.48 (t, J=2.3 Hz, 1H, CCH), 2.04-1.65 (m, 4H, CH$_2$CH$_2$CH$_2$N$_3$), 1.52 (s, 3H, CH$_3$), 1.51 (s, 3H, CH$_3$), 1.50-1.44 (m, 34H, CH$_3$/(CH$_3$)$_3$), 1.39 (s, 6H, CH$_3$); $^{13}$C NMR (50 MHz, CD$_2$Cl$_2$) δ 177.4, 176.2, 175.9, 175.6, 175.5, 175.4, 174.0, 170.1, 156.3, 81.8, 80.6, 74.7, 70.0, 58.8, 57.4, 57.4, 57.0, 57.0, 56.4, 54.9, 52.5, 51.7, 28.6, 28.5, 27.9, 27.7, 27.4, 27.3, 26.5, 25.5, 25.2, 23.7, 23.5, 23.4, 23.3, 23.1; HRMS (m/z): [M+Na]$^+$ calcd. for C$_{41}$H$_{69}$N$_{11}$O$_{12}$Na, 930.5024. found, 930.5017; Anal. Calcd. for C$_{41}$H$_{69}$N$_{11}$O$_{12}$: C, 54.23; H, 7.66; N, 16.97. Found: C, 54.2; H, 7.6; N, 16.6.

3.76 (m, 1H, C$^\alpha$H(azidonorVal)), 3.72 (dd, J=9.4, 3.1 Hz, 1H, C$^\alpha$HCHHO), 3.54 (s, 3H, OCH$_3$), 3.20 (t, J=9.2 Hz, 1H, C$^\alpha$HCHHO), 1.97-1.78 (m, 1H, CH$_2$CHHCH$_2$), 1.78-1.62 (m, 1H, CH$_2$CHHCH$_2$), 1.61-1.42 (m, 1H, C$^\alpha$HCHHCH$_2$CH$_2$), 1.38 (s, 3H, CH$_3$), 1.36 (s, 6H, CH$_3$), 1.34 (s, 3H, CH$_3$), 1.32 (s, 3H, CH$_3$), 1.31 (s, 3H, CH$_3$), 1.31-1.20 (m, 1H, C$^\alpha$HCHHCH$_2$CH$_2$); $^{13}$C NMR (75 MHz, DMSO-d$_6$) δ 174.1, 174.0, 173.8, 168.4, 168.2, 158.4 (q, J$_{CF}$=33 Hz), 144.5, 123.3, 68.9, 63.3, 56.5, 56.2, 55.1, 52.8, 51.8, 51.6, 48.6, 27.1, 26.2, 25.4, 25.2, 25.0, 24.3, 23.6, 23.3; HRMS (m/z): M$^+$ calcd. for C$_{24}$H$_{41}$N$_8$O$_7$, 553.3098. found, 553.3082; Anal. Calcd. for C$_{26}$H$_{41}$F$_3$N$_8$O$_9$: C, 46.84; H, 6.20; N, 16.81. Found: C, 45.8; H, 6.1; N, 16.1.

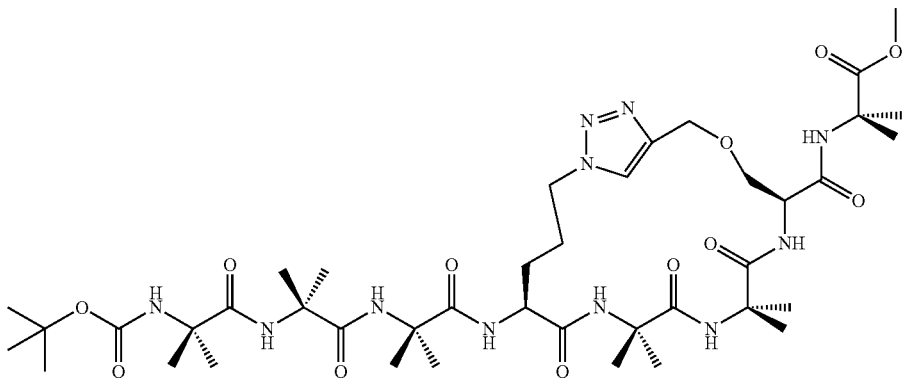

Methyl 2-methyl-2-((5S,14S)-8,8,11,11-tetramethyl-5-(2,2,6,6,9,9,12,12-octamethyl-4,7,10-trioxo-3-oxa-5,8,11-triazamidecanamido)-6,9,12-trioxo-16-oxa-1,7,10,13,19,20-hexaazabicyclo[16.2.1]henicosa-18 (21),19-dienecarboxamido)propanoate 23

(5S,14S)-14-(1-methoxy-2-methyl-1-oxopropan-2-ylcarbamoyl)-8,8,11,11-tetramethyl-6,9,12-trioxo-16-oxa-1,7,10,13,19,20-hexaazabicyclo[16.2.1]henicosa-18 (21),19-dien-5-aminium 2,2,2-trifluoroacetate 22 (0.332 g, 0.498 mmol) and N-tert-butoxycarbonyl α,α-dimethylglycyl α,α-dimethylglycyl α,α-dimethylglycine 7 (0.186 g, 0.498 mmol) were suspended in CH$_2$Cl$_2$ (3 mL) and a solution of N,N-diisopropylethylamine (0.065 g, 0.50 mmol) in CH$_2$Cl$_2$ (4 mL) added. HOBt hydrate (0.076 g, 0.50 mmol) and then EDC hydrochloride (0.105 g, 0.548 mmol) were added at room temperature together with additional CH$_2$Cl$_2$ (3 mL). The reaction mixture was stirred for 44 h at room temperature before being diluted with CH$_2$Cl$_2$ (40 mL). The solution was washed with 5% (w/w) citric acid monohydrate solution (3×20 mL), 7.5% (w/w) K$_2$CO$_3$ solution (3×20 mL) and saturated brine (20 mL). The solution was dried with anhydrous MgSO$_4$ and the solvent evaporated affording the title compound as a white solid (0.331 g, 73%); $^1$H NMR (300 MHz, CD$_2$Cl$_2$) δ 7.93 (s, 1H, NH(Aib$_3$)), 7.89 (s, 1H, NH(Aib$_5$)), 7.81 (d, J=6.1 Hz, 1H, NH(azidonorVal)), 7.75 (s, 1H, C$_2$HN$_3$), 7.54 (s, 1H, NH(Aib$_8$)), 7.43 (d, J=8.6 Hz, 1H, NH(propSer)), 7.03 (s, 1H, NH(Aib$_6$)), 6.86 (s, 1H, NH(Aib$_2$)), 5.51 (s, 1H, NH(Aib$_1$)), 4.83 (d, J=13.0 Hz, 1H, OCHHC$_2$HN$_3$), 4.56 (td, J=8.3, 2.9 Hz, 1H, C$^\alpha$H(propSer)), 4.51 (d, J=13.0 Hz, 1H, OCHHC$_2$HN$_3$), 4.39 (t, J=5.8 Hz, 2H, CH$_2$N$_3$C$_2$H), 3.89 (t, J=8.5 Hz, 1H, C$^\alpha$HCHHO), 3.72 (dd, J=9.0, 2.9 Hz, 1H, C$^\alpha$HCHHO), 3.65 (s, 3H, OCH$_3$), 3.25 (ddd, J=11.7, 5.9, 3.8 Hz, 1H, C$^\alpha$H(azidonorVal)), 2.33-2.16 (m, 1H, CH$_2$CHHCH$_2$), 2.16-1.93 (m, 2H, C$^\alpha$HCHHCH$_2$CH$_2$/CH$_2$CHHCH$_2$), 1.81-1.65 (m, 1H, C$^\alpha$HCHHCH$_2$CH$_2$), 1.51 (s, 3H, CH$_3$), 1.50-1.36 (m, 42H,

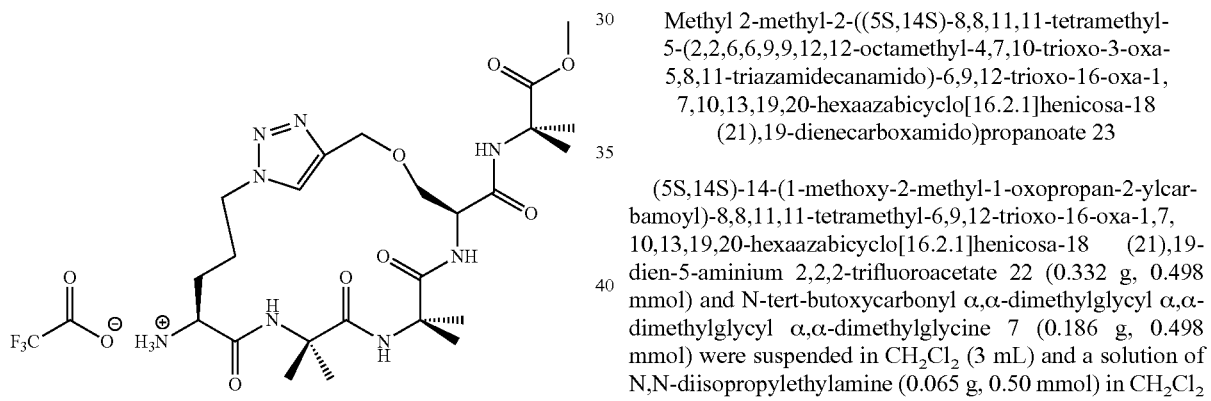

(5S,14S)-14-(1-methoxy-2-methyl-1-oxopropan-2-ylcarbamoyl)-8,8,11,11-tetramethyl-6,9,12-trioxo-16-oxa-1,7,10,13,19,20-hexaazabicyclo[16.2.1]henicosa-18 (21),19-dien-5-aminium 2,2,2-trifluoroacetate 22

A 50% (v/v) solution of TFA in CH$_2$Cl$_2$ (10 mL) was added to methyl 2-((5S,14S)-5-(tert-butoxycarbonylamino)-8,8,11,11-tetramethyl-6,9,12-trioxo-16-oxa-1,7,10,13,19,20-hexaazabicyclo[16.2.1]henicosa-18 (21),19-dienecarboxamido)-2-methylpropanoate 20 (0.390 g, 0.598 mmol) and the reaction mixture stirred for 1 h at room temperature. The solvent and bulk of excess TFA were evaporated and the residue washed with Et$_2$O (3×10 mL). The Et$_2$O was decanted off between each washing. The residue was dried under reduced pressure affording a fine white powder (0.400 g, 100%); $^1$H NMR (300 MHz, DMSO-d$_6$) δ 8.89 (s, 1H, NH(Aib$_2$)), 8.28 (br s, 3H, NH$_3^+$), 8.10 (s, 1H, NH(Aib$_3$)), 7.82 (s, 1H, C$_2$HN$_3$), 7.75 (s, 1H, NH(Aib$_5$)), 6.88 (d, J=9.2 Hz, 1H, NH(propSer)), 4.72 (d, J=13.4 Hz, 1H, OCHHC$_2$HN$_3$), 4.55-4.43 (m, 3H, C$^\alpha$H(propSer)/CH$_2$N$_3$C$_2$H), 4.38 (d, J=13.4 Hz, 1H, OCHHC$_2$HN$_3$), 3.87-

CH$_3$/(CH$_3$)$_3$); $^{13}$C NMR (75 MHz, CD$_2$Cl$_2$) δ 177.4, 175.9, 175.9, 175.6, 175.5, 175.5, 173.7, 170.0, 156.4, 145.3, 125.1, 81.8, 70.0, 65.3, 57.5, 57.5, 57.4, 57.3, 57.1, 56.4, 55.2, 54.5, 52.5, 49.7, 28.6, 28.3, 27.9, 27.9, 27.3, 27.2, 27.0, 25.4, 25.3, 24.8, 23.7, 23.4, 23.3, 23.2, 23.0; HRMS (m/z): [M+H]$^+$ calcd for C$_{41}$H$_{70}$N$_{11}$O$_{12}$, 908.5205. found, 908.5194; Anal. Calcd for C$_{41}$H$_{69}$N$_{11}$O$_{12}$: C, 54.23; H, 7.66; N, 16.97. Found: C, 54.0; H, 7.6; N, 16.5.

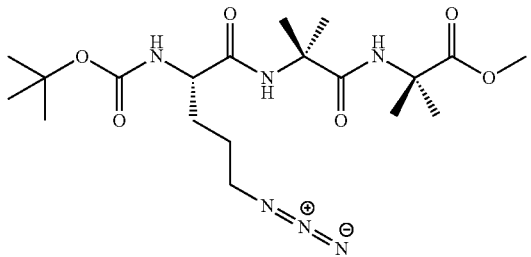

N$^α$-Tert-Butoxycarbonyl ε-Azido-L-Norvalyl α,α-Dimethylglycyl α,α-Dimethylglycine Methyl Ester 24

α,α-Dimethylglycyl α,α-dimethylglycine methyl ester trifluoroacetate 5 (5.29 g, 16.7 mmol) was dissolved in DMF (20 mL) and N,N-diisopropylethylamine (5.90 g, 45.6 mmol) added. The resulting solution was added to a solution of N$^α$-tert-butoxycarbonyl ε-azido-L-norvaline 11 (3.93 g, 15.2 mmol) in DMF (25 mL) in one portion followed by additional DMF (20 mL). PyBOP (8.71 g, 16.7 mmol) and HOBt hydrate (2.56 g, 16.7 mmol) were added at room temperature together with more DMF (25 mL). The reaction mixture was stirred for 1 h at room temperature before the solvent was evaporated at 65° C. over 30 min. The residue was taken up in EtOAc (225 mL) and washed with 1 M aqueous H$_2$SO$_4$ (3×70 mL), 7.5% (w/w) K$_2$CO$_3$ solution (3×70 mL) and saturated brine (70 mL). The solution was dried with anhydrous MgSO$_4$ and the solvent evaporated affording a slightly yellowish oil (8.94 g). The oil (8.78 g) was purified by flash column chromatography (eluent:EtOAc/hexane (7:3)) affording the title compound as a white solid (5.76 g, corresponds to 5.87 g for the given amounts of starting materials, 87%); $^1$H NMR (200 MHz, DMSO-d$_6$, 40° C.) 7.84 (s, 1H, NH(Aib)), 7.38 (s, 1H, NH(Aib)), 7.00 (d, J=6.9 Hz, 1H, NH(azidonorVal)), 3.90-3.73 (m, 1H, C$^α$H), 3.55 (s, 3H, OCH$_3$), 3.31 (t, J=6.0 Hz, 2H, CH$_2$N$_3$), 1.75-1.47 (m, 4H, CH$_2$CH$_2$), 1.39 (s, 9H, (CH$_3$)$_3$) 1.37 (s, 3H, CH$_3$), 1.35 (s, 6H, CH$_3$), 1.33 (s, 3H, CH$_3$); $^{13}$C NMR (50 MHz, DMSO-d$_6$) δ 174.3, 173.5, 171.3, 155.7, 78.3, 55.8, 55.1, 54.4, 51.7, 50.4, 28.3, 28.2, 25.3, 24.9, 24.8, 24.3, 23.9; HRMS (m/z): [M+Na]$^+$ calcd. for C$_{19}$H$_{34}$N$_6$O$_6$Na, 465.2437. found, 465.2447; Anal. Calcd. for C$_{19}$H$_{34}$N$_6$O$_6$: C, 51.57; H, 7.74; N, 18.99. Found: C, 51.7; H, 7.8; N, 19.4.

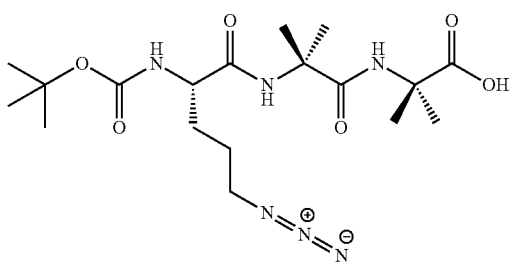

N$^α$-Tert-Butoxycarbonyl ε-Azido-L-Norvalyl α,α-Dimethylglycyl α,α-Dimethylglycine 25

N$^α$-tert-butoxycarbonyl ε-azido-L-norvalyl α,α-dimethylglycyl α,α-dimethylglycine methyl ester 24 (0.640 g, 1.45 mmol) was dissolved in THF (12 mL) and the solution cooled to 0° C. (ice bath). An icecold solution of LiOH.H$_2$O (0.038 g, 1.59 mmol) in de-ionized H$_2$O (6 mL) was added dropwise over 10 min. The reaction mixture was stirred for an additional 1 h 50 min at 0° C. before solid NaHCO$_3$ (0.243 g, 2.89 mmol) was added. The mixture was stirred for 10 min at 0° C. and the bulk of THF evaporated (remaining volume: 4.5 mL). The solution/suspension was diluted with H$_2$O (12 mL), washed with Et$_2$O (4×12 mL) and acidified to pH 1-2 by addition of 3M HCl. The Et$_2$O phases were dried with anhydrous MgSO$_4$ and the solvent evaporated affording unreacted starting material (0.330 g). The aqueous suspension was extracted with EtOAc (2×24 mL+36 mL). The combined organic extracts were dried with anhydrous MgSO$_4$ and the solvent evaporated affording the title compound as a white solid (0.249 g, 40%).; $^1$H NMR (300 MHz, DMSO-d$_6$) δ 12.01 (br s, 1H, COOH), 7.95 (s, 1H, NH(Aib)), 7.27 (s, 1H, NH(Aib)), 7.06 (d, J=6.5 Hz, 1H, NH(azidonorVal)), 3.90-3.70 (m, 1H, C$^α$H), 3.30 (t, J=6.2 Hz, 2H, CH$_2$N$_3$), 1.71-1.46 (m, 4H, CH$_2$CH$_2$), 1.39 (s, 9H, (CH$_3$)$_3$), 1.35 (s, 3H, CH$_3$), 1.34 (s, 3H, CH$_3$), 1.32 (s, 3H, CH$_3$), 1.32 (s, 3H, CH$_3$); $^{13}$C NMR (75 MHz, DMSO-d$_6$) δ 175.5, 173.2, 171.4, 155.7, 78.3, 55.9, 55.0, 54.4, 50.4, 28.4, 28.2, 25.3, 24.9, 24.8, 24.3, 24.1; HRMS (m/z): [M+Na]$^+$ calcd. for C$_{18}$H$_{32}$N$_6$O$_6$Na, 451.2281. found, 451.2293; Anal. Calcd. for C$_{18}$H$_{32}$N$_6$O$_6$: C, 50.46; H, 7.53; N, 19.61. Found: C, 50.5; H, 7.6; N, 19.9.

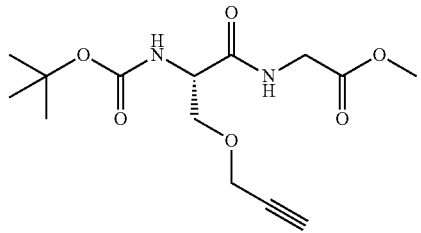 [SMILES: C#CCOC[C@H](NC(=O)OC(C)(C)C)C(=O)NCC(=O)OC]

N-Tert-Butoxycarbonyl O-Propynyl L-Seryl Glycine Methyl Ester 27

N-tert-butoxycarbonyl O-propynyl L-serine (14.55 g, 59.82 mmol) was dissolved in DMF (60 mL) and the solution cooled to 0° C. (icebath). Glycine methyl ester hydrochloride (7.51 g, 59.8 mmol) was suspended in DMF (40 mL) and N,N-diisopropylethylamine (7.73 g, 59.8 mmol) added. The resulting suspension was added to the solution of N-tert-butoxycarbonyl O-propynyl L-serine in one portion. HOBt hydrate (9.16 g, 59.8 mmol) dissolved in DMF (20 mL) was added. Finally, EDC hydrochloride (12.61 g, 65.8 mmol) was added in small portions. The reaction mixture was stirred for 1 h at 0° C. after which the icebath was removed and stirring continued for 25 h at room temperature before the solvent was evaporated. The residue was taken up in EtOAc (400 mL) and the solution washed with 1 M aqueous H$_2$SO$_4$ (3×200 mL), 7.5% (w/w) K$_2$CO$_3$ solution (3×200 mL) and saturated brine (200 mL). The solution was dried with anhydrous MgSO$_4$ and the solvent evaporated affording a yellow/orange oil (17.23 g, 92%); δ$_H$ (300 MHz; d$_6$-DMSO) 8.31 (1H, t, J 6, NH(Gly)), 6.85 (1H, d, J 8, NH(propSer)), 4.26-4.15 (1H, m, C$^α$H (propSer)), 4.13 (2H, t, J 2, CH$_2$CCH), 3.88 (1H, dd, J 17 and 6, C$^α$HH(Gly)), 3.81 (1H, dd, J 17 and 6, C$^α$HH(Gly)), 3.65 (1H, dd, J 10 and 5, CHH), 3.62 (3H, s, OCH$_3$), 3.52 (1H, dd, J 10 and 8, CHH), 3.41 (1H, t, J 2, CCH), 1.39 (9H, s, (CH$_3$)$_3$); δ$_C$ (75 MHz; d$_6$-DMSO) 170.2, 170.0, 155.1, 79.9, 78.3, 77.2, 69.2, 59.7, 57.6, 54.0, 51.6, 40.6, 28.1, 20.7, 14.0

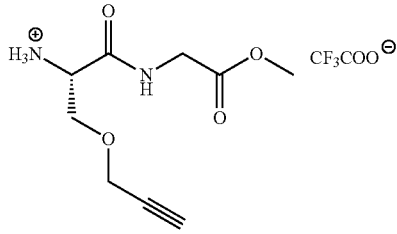

O-Propynyl L-Seryl Glycine Methyl Ester Trifluoroacetate 28

N-tert-butoxycarbonyl O-propynyl L-seryl glycine methyl ester (2.52 g, 8.02 mmol) was dissolved in CH$_2$Cl$_2$ (15 mL). Trifluoroacetic acid (15 mL) was added and the reaction mixture stirred for 2 h at room temperature. The solvent and bulk of excess TFA were removed and the residue washed with Et$_2$O (2×15 mL). The diethyl ether was decanted off and the residue dried under vacuum before being redissolved in CH$_2$Cl$_2$ (70 mL). The solvent was evaporated and the residue dried under high vacuum overnight affording a brown, viscous oil (2.32 g, 88%); δ$_H$ (200 MHz; d$_6$-DMSO) 8.97 (1H, t, J 6, NH), 8.31 (3H, br s, NH$_3^+$), 4.21 (2H, d, J 2, CH$_2$CCH), 4.16-4.05 (1H, m, C$^α$H(propSer)), 3.96 (2H, d, J 6, C$^α$H$_2$(Gly)), 3.83 (1H, dd, J 11 and 4, CHH), 3.74 (1H, dd, J 11 and 6, CHH), 3.65 (3H, s, OCH$_3$), 3.55 (1H, t, J 2, CCH).

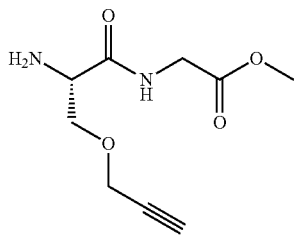

O-Propynyl L-Seryl Glycine Methyl Ester 29

N-tert-butoxycarbonyl-O-propargyl L-seryl glycine methyl ester (6.17 g, 19.6 mmol) was treated with a 50% (v/v) solution of TFA in CH$_2$Cl$_2$ (50 mL). The reaction mixture was stirred for 1 h 20 min before the solvent and bulk of excess TFA was evaporated. The residue was dissolved in H$_2$O (50 mL) and the solution washed with Et$_2$O (3×25 mL). The pH was regulated to pH 10-11 and the solution extracted with CH$_2$Cl$_2$ (3×100 mL). The combined organic extracts were dried with anhydrous MgSO$_4$ and the solvent evaporated affording a yellowish liquid (2.75 g, 65%); δ$_H$ (300 MHz; d$_6$-DMSO) 8.33 (1H, t/dd, J difficult to measure, NH), 4.14 (2H, d, J 2, CH$_2$CCH), 3.87 (1H, s, C$^α$HH(Gly)), 3.85 (1H, s, C$^α$HH(Gly)), 3.63 (3H, s, OCH$_3$), 3.58 (1H, dd, J 9 and 5, CHH), 3.49 (1H, dd, J 9 and 6, CHH), 3.41 (1H, dd, J 6 and 5, C$^α$H(propSer)), 3.30 (1H, t, J 2, CCH), 1.86 (2H, br s, NH$_2$); δ$_C$ (75 MHz; d$_6$-DMSO) 173.1, 170.2, 80.1, 77.1, 72.1, 57.6, 54.8, 54.3, 51.6, 40.5

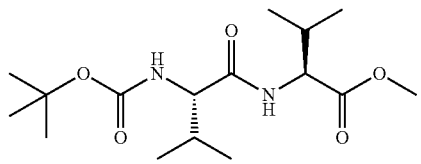 [SMILES: COC(=O)[C@@H](NC(=O)[C@@H](NC(=O)OC(C)(C)C)C(C)C)C(C)C]

N-Tert-Butoxycarbonyl L-Valyl L-Valine Methyl Ester 30

N-tert-butoxycarbonyl L-valine (11.67 g, 53.71 mmol) was dissolved in DMF (50 mL) and the solution cooled to 0° C. (icebath). L-valine methyl ester hydrochloride (9.01 g, 53.7 mmol) was suspended in DMF (25 mL) and N,N-diisopropylethylamine (6.94 g, 53.7 mmol) added. The resulting solution was added to the solution of N-tert-butoxycarbonyl L-valine together with DMF (5 mL). HOBt hydrate (8.23 g, 53.7 mmol) and then EDC hydrochloride (11.33 g, 59.10 mmol) were added in portions together with an additional 30 mL DMF. The reaction mixture was stirred at 0° C. for 2 h 30 min after which the icebath was removed and stirring continued for 22 h 30 min at room temperature. The solvent was evaporated and the residue taken up in EtOAc (250 mL). The solution/suspension was washed with 1 M aqueous H$_2$SO$_4$ (3×100 mL), 7.5% (w/w) K$_2$CO$_3$ solution (3×100 mL) and saturated brine (100 mL). The solution was dried with anhydrous MgSO$_4$ and the solvent evaporated affording a white solid (16.92 g, 95%); δ$_H$ (200 MHz; d$_6$-DMSO) 7.97 (1H, dd, J 8, NH(Val$_2$)), 6.68 (1H, dd, J 9, NH(Val$_1$)), 4.18 (1H, dd, J 8 and 6, C$^α$H(Val$_2$)), 3.86 (1H, dd, J 9 and 8, C$^α$H(Val$_1$)), 3.61 (3H, s, OCH$_3$), 2.15-1.79 (2H, m, CH(CH$_3$)), 1.37 (9H, s, (CH$_3$)$_3$), 0.91-0.80 (12H, m, CH$_3$); δ$_C$ (50 MHz, d$_6$-DMSO): 171.7, 171.7, 155.3, 77.9, 59.4, 57.2, 51.5, 30.2, 29.8, 28.0, 19.0, 18.8, 18.1, 18.1

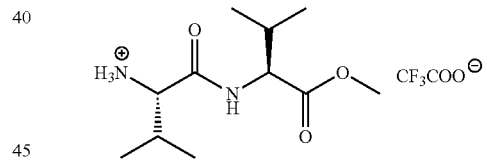

L-Valyl L-Valine Methyl Ester Trifluoroacetate 31

N-tert-butoxycarbonyl L-valyl L-valine methyl ester (16.47 g, 49.85 mmol) was treated with a 50% (v/v) solution of TFA in CH$_2$Cl$_2$ (130 mL). The reaction mixture was stirred for 2 h at room temperature before the solvent and bulk of excess TFA were evaporated. Portions of CH$_2$Cl$_2$ (3×100 mL) and purified CHCl$_3$ (6×200 mL) were added and evaporated. The residue (19.17 g) was washed with Et$_2$O (2×80 mL) and the Et$_2$O decanted off. An additional 80 mL Et$_2$O was added and the suspension filtered. The collected solid was washed with Et$_2$O (80 mL) and dried; δ$_H$ (300 MHz; d$_6$-DMSO) 8.62 (1H, d, J 7, NH), 8.17 (3H, br s, NH$_3^+$), 4.19 (1H, dd, J 7 and 6, C$^α$H(Val$_2$)), 3.75 (1H, br d, J 5, C$^α$H(Val$_1$)), 3.64 (3H, s, OCH$_3$), 2.16-2.01 (2H, m, CH(CH$_3$)$_2$), 0.96-0.90 (12H, m, CH(CH$_3$)$_2$); δ$_C$ (75 MHz; d$_6$-DMSO) 171.4, 168.4, 158.4 (q, J$_{CF}$ 31), 117.1 (q, J$_{CF}$ 297) 57.7, 56.9, 51.7, 29.9, 29.6, 18.8, 18.1, 18.1, 17.4

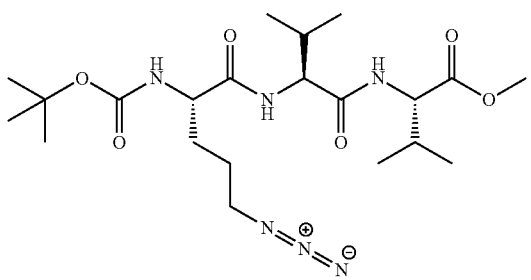 [SMILES: COC(=O)[C@@H](NC(=O)[C@@H](NC(=O)[C@H](CCCN=[N+]=[N-])NC(=O)OC(C)(C)C)C(C)C)C(C)C]

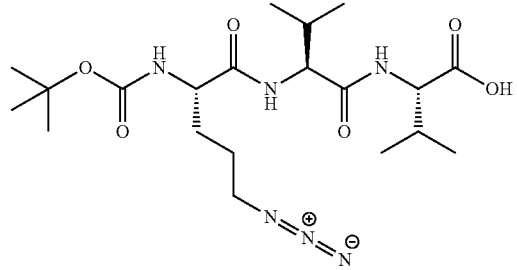 [SMILES: CC(C)[C@H](NC(=O)[C@@H](NC(=O)[C@H](CCCN=[N+]=[N-])NC(=O)OC(C)(C)C)C(C)C)C(=O)O]

N-Tert-Butoxycarbonyl ε-Azido-L-Norvalyl L-Valyl L-Valine Methyl Ester 32

$N^\alpha$-tert-butoxycarbonyl-$N^\epsilon$-azido-L-norvaline (3.06 g, 11.8 mmol) was dissolved in DMF (10 mL). A solution of L-valyl L-valine methyl ester trifluoroacetate (4.08 g, 11.8 mmol) and N,N-diisopropylethylamine (1.53 g, 11.8 mmol) in DMF (10 mL) was added. HOBt hydrate (1.81 g, 11.8 mmol) and EDC hydrochloride (2.52 g, 13.1 mmol) were added together with additional DMF (5 mL). The reaction mixture was stirred for 22 h before the solvent was evaporated. The residue was taken up in EtOAc (100 mL) and the solution washed with 1 M aqueous $H_2SO_4$ (3×30 mL), 7.5% (w/w) $K_2CO_3$ solution (3×30 mL) and saturated brine (30 mL). The solution was dried with anhydrous $MgSO_4$ and the solvent evaporated affording the title compound as a white solid (5.24 g, 94%); $\delta_H$ (200 MHz; $d_6$-DMSO) 8.18 (1H, d, J 8, NH(Val$_x$)), 7.62 (1H, d, J 9, NH(Val$_y$)), 7.04 (1H, d, J 8, NH(anorVal)), 4.31 (1H, dd, J 9 and 7, C$^\alpha$H(Val$_y$)), 4.13 (1H, dd, J 8 and 6, C$^\alpha$H(Val$_x$)), 4.05-3.83 (1H, m, C$^\alpha$H(anorVal)), 3.61 (3H, s, OCH$_3$), 3.29 (2H, t, J 6, CH$_2$N$_3$) 2.15-1.82 (2H, m, CH(CH$_3$)$_2$), 1.71-1.44 (4H, m, CH$_2$), 1.37 (9H, s, (CH$_3$)$_3$), 0.90-0.81 (12H, m, CH$_3$); $\delta_C$ (75 MHz; CDCl$_3$) 172.2, 172.0, 171.1, 155.7, 79.9, 58.6, 57.0, 53.9, 53.9, 52.0, 51.1, 31.0, 30.9, 29.7, 28.3, 25.1, 19.0, 18.9, 18.3, 17.8.

$N^\alpha$-Tert-Butoxycarbonyl-$N^\epsilon$-Azido-L-Norvalyl L-Valyl L-Valine 33

$N^\alpha$-tert-butoxycarbonyl-$N^\epsilon$-azido-L-norvalyl L-valyl L-valine methyl ester (4.11 g, 8.73 mmol) was dissolved in THF (70 mL) and the solution cooled to 0° C. (icebath). LiOH monohydrate (0.403 g, 9.60 mmol) was dissolved in de-ionized water (35 mL) and the solution cooled to 0° C. The ice-cold solution of LiOH was added dropwise to the solution of $N^\alpha$-tert-butoxycarbonyl-$N^\epsilon$-azido-L-norvalyl L-valyl L-valine methyl ester over 20 min. The reaction mixture was stirred for an additional 2 h 40 min at 0° C. The bulk of THF was evaporated and the remaining solution diluted with $H_2O$ (70 mL) and washed with $Et_2O$ (2×70 mL). The solution was acidified to pH 2 by addition of 2 M aqueous $H_2SO_4$ and extracted with EtOAc (3×100 mL). The combined organic extracts were dried with anhydrous $MgSO_4$ and the solvent evaporated affording a white solid (2.46 g, 62%). The ether washings were dried with anhydrous $MgSO_4$ and the solvent evaporated affording 1.38 g of unreacted starting material; $\delta_H$ (300 MHz; $d_6$-DMSO) 12.52 (1H, br s, COOH), 7.99 (1H, d, J 8, NH(Val$_x$)), 7.62 (1H, d, J 9, NH(Val$_y$)), 7.04 (1H, d, J 8, NH(anorVal)), 4.32 (1H, dd, J 9 and 7, C$^\alpha$H(Val$_y$)), 4.11 (1H, dd, J 8 and 6, C$^\alpha$H(Val$_x$)), 4.03-3.86 (1H, m, C$^\alpha$H(anorVal)), 3.28 (2H, t, J 6, CH$_2$N$_3$), 2.12-1.88 (2H, m, CH(CH$_3$)$_2$), 1.70-1.47 (4H, m, CH$_2$), 1.37 (9H, s, (CH$_3$)$_3$), 0.89-0.82 (12H, m, CH$_3$); $\delta_C$ (75 MHz; $d_6$-DMSO) 172.6, 171.5, 171.0, 155.2, 78.0, 57.1, 56.8, 53.9, 50.3, 31.0, 29.6, 29.0, 28.1, 24.9, 19.0, 18.9, 17.9, 17.8.

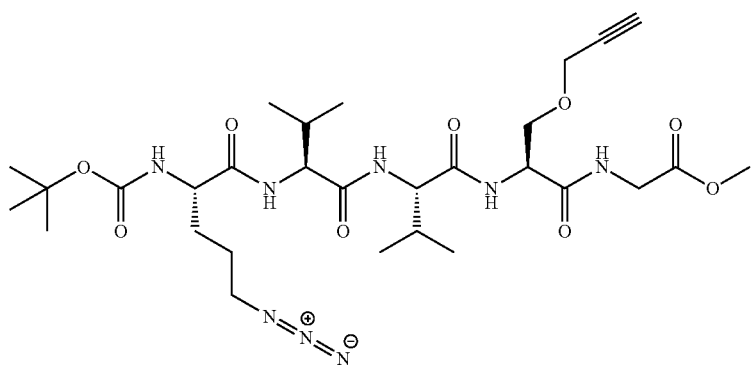 [SMILES: C#CCOC[C@H](NC(=O)[C@@H](NC(=O)[C@@H](NC(=O)[C@H](CCCN=[N+]=[N-])NC(=O)OC(C)(C)C)C(C)C)C(C)C)C(=O)NCC(=O)OC]

N$^\alpha$-Tert-Butoxycarbonyl-N$^\epsilon$-Azido-L-Norvalyl L-Valyl L-Valyl O-Propynyl L-Seryl Glycine Methyl Ester 34

N$^\alpha$-tert-butoxycarbonyl-N$^\epsilon$-azido-L-norvalyl L-valyl L-valine (0.290 g, 0.635 mmol), O-propargyl L-seryl glycine methyl ester (0.136 g, 0.635 mmol) and HOBt hydrate (0.098 g, 0.64 mmol) were dissolved in CH$_2$Cl$_2$ (10 mL) and EDC hydrochloride (0.135 g, 0.704 mmol) added slowly. The reaction mixture was stirred for 21 h. The solution was diluted by addition of CH$_2$Cl$_2$ (65 mL) and the solution washed with 2 M aqueous H$_2$SO$_4$ (3×20 mL) (50 mL water was added after each washing—significant problems with emulsion formation!), 7.5% (w/w) K$_2$CO$_3$ solution (3×20 mL) (50 mL water was added after each washing) and saturated brine (80 mL). The solution was dried over 3 Å molecular sieves and the solvent evaporated affording the title compound as a white solid (0.287 g, 69%); $\delta_H$ (300 MHz; d$_6$-DMSO) 8.38 (1H, t, J 6, NH(Gly)), 7.99 (1H, d, J 8, NH (propSer)), 7.88 (1H, d, J 9, NH(Val$_x$)), 7.68 (1H, d, J 9, NH(Val$_y$)), 7.03 (1H, d, J 8, NH(anorVal)), 4.51 (1H, m, J 8, C$^\alpha$H(propSer)), 4.28-4.19 (2H, m, C$^\alpha$H(Val$_x$)/C$^\alpha$H(Val$_y$)), 4.13 (2H, d, J 2, CH$_2$CCH), 3.96 (1H, m, C$^\alpha$H(anorVal)), 3.86 (1H, s, C$^\alpha$HH(Gly)), 3.84 (1H, s, C$^\alpha$HH(Gly)), 3.64-3.54 (2H, m, CH$_2$ (propSer)), 3.61 (3H, s, OCH$_3$), 3.43 (1H, t, J 2, CCH), 2.03-1.89 (2H, m, CH(CH$_3$)$_2$), 1.67-1.52 (4H, m, CH$_2$ (anorVal)), 1.37 (9H, s, (CH$_3$)$_3$), 0.84-0.80 (12H, m, CH(CH$_3$)$_2$) (Note: CH$_2$N$_3$ overlapped with water peak); $\delta_C$ (75 MHz; d$_6$-DMSO) 171.6, 170.6, 169.9, 169.5, 145.6, 98.1 (CH$_2$Cl$_2$?), 79.8, 77.4, 57.6, 51.6, 50.3, 30.7, 30.3, 28.1, 19.1, 19.0, 17.8 (Note: sample was quite thin, so some carbon signals are missing)

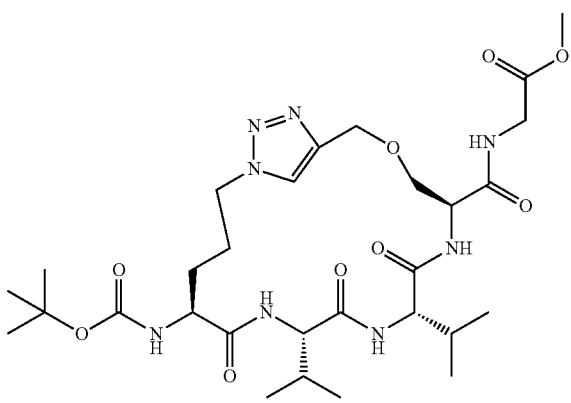 [SMILES: COC(=O)CNC(=O)[C@@H]1COCc2cn(nn2)CCC[C@H](NC(=O)OC(C)(C)C)C(=O)N[C@@H](C(C)C)C(=O)N[C@@H](C(C)C)C(=O)N1]

Methyl 2-((5S,8S,11S,14S)-5-(tert-butoxycarbonylamino)-8,11-diisopropyl-6,9,12-trioxo-16-oxa-1,7,10,13,19,20-hexaazabicyclo[16.2.1]henicosa-18(21),19-dienecarboxamido)acetate 35

N$^\alpha$-tert-butoxycarbonyl-N$^\epsilon$-azido-L-norvalyl L-valyl L-valyl O-propynyl L-seryl glycine methyl ester (0.172 g, 0.264 mmol) was dissolved in CH$_2$Cl$_2$ (1750 mL) by vigorous stirring overnight. The solution was very slightly turbid, but no macroscopic particles were visible. Next, N,N-diisopropylethylamine (0.5112 g, 3.955 mmol) was dissolved in CH$_2$Cl$_2$ (50 mL) and 10 mL added to the solution of N$^\alpha$-tert-butoxycarbonyl-N$^\epsilon$-azido-L-norvalyl L-valyl L-valyl O-propynyl L-seryl glycine methyl ester over 10 min and protected from sunlight. Copper(I) iodide triethylphosphite complex (0.3755 g, 1.635 mmol) was dissolved in CH$_2$Cl$_2$ (100 mL) and 5 mL solution added to the solution of N$^\alpha$-tert-butoxycarbonyl-N$^\epsilon$-azido-L-norvalyl L-valyl L-valyl O-propynyl L-seryl glycine methyl ester. The reaction mixture was stirred for 48 h at room temperature protected from sunlight before the solution was concentrated and the residue purified by flash column chromatography (CH$_2$Cl$_2$/MeOH (9:1)), affording the title compound as a slightly greenish solid HRMS (m/z): [M+H]+ calcd. for C29H49N8O9, 653.3622. found, 653.3611.

The invention claimed is:

1. A peptide which adopts 3$_{10}$-helical conformation in which the side chains of two amino acid residues in the peptide backbone are linked by a group comprising an aromatic 5-membered ring, wherein said two amino acids are 3 units apart (residues i to i+3) and wherein the mean intramolecular hydrogen bond length is shorter as compared to an analogous peptide lacking side chains linked by said group.

2. A peptide as claimed in claim 1 having 4 to 15 amino acid residues.

3. A peptide as claimed in claim 1 where the aromatic 5-membered ring is a triazole.

4. A peptide as claimed in claim 1 in which one of said two amino acids is a serine residue.

5. A peptide as claimed in claim 1 in which one of said two amino acids is a ornithine or norvaline residue.

6. A peptide as claimed in claim 1 wherein the peptide backbone is linked by a group of formula (I)

wherein L$_1$ is a C$_{2-5}$-alkyl chain optionally interrupted by at least one heteroatom, especially one O atom and L$_2$ is a C$_{2-5}$ alkyl chain optionally interrupted by at least one heteroatom, especially one O atom.

7. A peptide as claimed in claim 1 wherein L$_2$ is CH$_2$—O—CH$_2$.

8. A peptide as claimed in claim 1 wherein L$_1$ is (CH$_2$)$_3$.

9. A peptide as claimed in claim 1 wherein there are 18-20 atoms in the ring formed by the linker and the peptide backbone.

10. A peptide as claimed in claim 1 wherein the peptide comprises a residue of valine.

11. A peptide as claimed in claim 1 wherein the peptide comprises a residue of Aib.

12. A peptide as claimed in claim 1 wherein a valine residue and/or Aib residue form parts of the peptide backbone between the linked amino acid residues.

13. A peptide as claimed in claim 1 wherein the linker group binds to the peptide backbone at carbon atoms in said backbone.

14. A peptide as claimed in claim 1 wherein any amino acid is in its L chiral form.

15. A peptide as claimed in claim 1 being crystalline.

16. A peptide as claimed in claim 1 having a water solubility of at least 1 mM.

17. A peptide as claimed in claim 1 whose 3$_{10}$-helical conformation is enthalpically and/or entropically stabilised with respect to unfolding relative to a comparable peptide without the linker.

18. A pharmaceutical composition comprising a peptide as claimed in claim 1.

19. A process for preparation of a peptide in 3$_{10}$-helical conformation in which the side chains of two amino acid residues in the peptide backbone are linked by a group comprising an aromatic 5-membered ring, wherein said two amino acids are 3 units apart (residues i to i+3 residues) and wherein the mean intramolecular hydrogen bond length is shorter as compared to an analogous peptide lacking side chains linked by said group; said process comprising:

reacting an azide functionalised side chain of an amino acid with an alkyne functionalised side chain of an amino acid positioned 3 residues away from each other in the presence of a Cu(I) catalyst.

20. A method for stabilising a short peptide of between 4 and 15 units in a conformationally rigid $3_{10}$-helical conformation by cyclising the side chains of two separate amino acid residues using a linker comprising a triazole group.

21. A method for treating an AQP4 related condition comprising administering to a patient in need thereof an effective amount of a peptide as claimed in claim 1.

22. A method as claimed in claim 20 wherein the short peptide is between 5 to 12 units.

* * * * *